United States Patent
Islam et al.

(10) Patent No.: US 10,344,020 B2
(45) Date of Patent: Jul. 9, 2019

(54) SELECTIVE NR2B ANTAGONISTS

(71) Applicant: BRISTOL-MYERS SQUIBB COMPANY, Princeton, NJ (US)

(72) Inventors: Imadul Islam, Richmond, CA (US); Srinivasan Thangathirupathy, Hosur (IN); Jayakumar Sankara Warrier, Bangalore (IN); Srinivas Cheruku, Bangalore (IN); Poornima Shetty, Bangalore (IN); Grandhi Venkat Ram Krishna Mohan Gupta, Bangalore (IN); John E. Macor, Washington Crossing, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/767,386

(22) PCT Filed: Oct. 13, 2016

(86) PCT No.: PCT/US2016/056714
§ 371 (c)(1),
(2) Date: Apr. 11, 2018

(87) PCT Pub. No.: WO2017/066366
PCT Pub. Date: Apr. 20, 2017

(65) Prior Publication Data
US 2018/0312491 A1 Nov. 1, 2018

(30) Foreign Application Priority Data
Oct. 14, 2015 (IN) .......................... 3308/DEL/2015

(51) Int. Cl.
| C07D 403/14 | (2006.01) |
|---|---|
| C07D 401/12 | (2006.01) |
| C07D 471/08 | (2006.01) |
| A61P 25/28 | (2006.01) |
| A61P 25/02 | (2006.01) |
| A61P 25/24 | (2006.01) |
| A61P 25/16 | (2006.01) |
| C07D 401/14 | (2006.01) |
| C07D 487/08 | (2006.01) |

(52) U.S. Cl.
CPC ............ *C07D 403/14* (2013.01); *A61P 25/02* (2018.01); *A61P 25/16* (2018.01); *A61P 25/24* (2018.01); *A61P 25/28* (2018.01); *C07D 401/12* (2013.01); *C07D 401/14* (2013.01); *C07D 471/08* (2013.01); *C07D 487/08* (2013.01)

(58) Field of Classification Search
USPC ......... 544/243, 295, 337, 364; 540/542, 575
See application file for complete search history.

(56) References Cited

U.S. PATENT DOCUMENTS

| 7,022,728 B2 | 4/2006 | Cowart et al. |
|---|---|---|
| 9,187,506 B2 | 11/2015 | Thompson, III et al. |
| 9,221,796 B2 | 12/2015 | King et al. |
| 2015/0191452 A1* | 7/2015 | King .................... C07D 403/04 514/210.2 |
| 2015/0191496 A1* | 7/2015 | Thompson, III .... C07F 9/65583 514/89 |
| 2018/0312495 A1* | 11/2018 | Islam ................... C07D 413/14 |

FOREIGN PATENT DOCUMENTS

WO    WO 2011/100585 A1    8/2011

* cited by examiner

*Primary Examiner* — Nyeemah A Grazier
(74) *Attorney, Agent, or Firm* — Mintz Levin Cohn Ferris Glovsky and Popeo, P.C.

(57) ABSTRACT

The disclosure generally relates to compounds of formula I, including their salts, as well as compositions and methods of using the compounds. The compounds are ligands of the NR2B receptor and may be useful for the treatment of various disorders of the central nervous system.

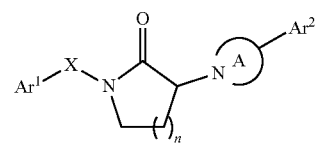

13 Claims, No Drawings

SELECTIVE NR2B ANTAGONISTS

CROSS REFERENCE TO RELATED APPLICATION

This application claims the benefit of Indian Provisional Patent Application serial number 3308/DEL/2015 filed Oct. 14, 2015 hereby incorporated by reference in its entirety.

TECHNICAL FIELD

The disclosure generally relates to compounds of formula I, including their salts, as well as compositions and methods of using the compounds. The compounds are ligands for the NR2B NMDA receptor and may be useful for the treatment of various disorders of the central nervous system.

BACKGROUND

N-Methyl-D-aspartate (NMDA) receptors are ion channels which are gated by the binding of glutamate, an excitatory neurotransmitter in the central nervous system. They are thought to play a key role in the development of a number of neurological diseases, including depression, neuropathic pain, Alzheimer's disease, and Parkinson's disease. Functional NMDA receptors are tetrameric structures primarily composed of two NR1 and two NR2 subunits. The NR2 subunit is further subdivided into four individual subtypes: NR2A, NR2B, NR2C, and NR2D, which are differentially distributed throughout the brain. Antagonists or allosteric modulators of NMDA receptors, in particular NR2B subunit-containing channels, have been investigated as therapeutic agents for the treatment of major depressive disorder (G. Sanacora, 2008, Nature Rev. Drug Disc. 7: 426-437).

The NR2B receptor contains additional ligand binding sites in addition to that for glutamate. Non-selective NMDA antagonists such as Ketamine are pore blockers, interfering with the transport of $Ca^{++}$ through the channel. Ketamine has demonstrated rapid and enduring antidepressant properties in human clinical trials as an i.v. drug. Additionally, efficacy was maintained with repeated, intermittent infusions of Ketamine (Zarate et al., 2006, Arch. Gen. Psychiatry 63: 856-864). This class of drugs, though, has limited therapeutic value because of its CNS side effects, including dissociative effects.

An allosteric, non-competitive binding site has also been identified in the N-terminal domain of NR2B. Agents which bind selectively at this site, such as Traxoprodil, exhibited a sustained antidepressant response and improved side effect profile in human clinical trials as an i.v. drug (Preskorn et al., 2008, J. Clin. Psychopharmacol., 28: 631-637, and F. S. Menniti, et al., 1998, CNS Drug Reviews, 4, 4, 307-322). However, development of drugs from this class has been hindered by low bioavailability, poor pharmacokinetics, and lack of selectivity against other pharmacological targets including the hERG ion channel. Blockade of the hERG ion channel can lead to cardiac arrythmias, including the potentially fatal Torsades de pointe, thus selectivity against this channel is critical. Thus, in the treatment of major depressive disorder, there remains an unmet clinical need for the development of effective NR2B-selective negative allosteric modulators which have a favorable tolerability profile.

NR2B receptor antagonists have been disclosed in PCT publication WO 2009/006437.

The invention provides technical advantages, for example, the compounds are novel and are ligands for the NR2B receptor and may be useful for the treatment of various disorders of the central nervous system. Additionally, the compounds provide advantages for pharmaceutical uses, for example, with regard to one or more of their mechanism of action, binding, inhibition efficacy, target selectivity, solubility, safety profiles, or bioavailability.

SUMMARY

In a first embodiment, the disclosure provides a compound of the formula I

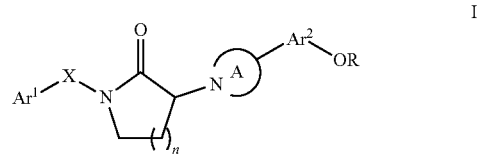

where:
$Ar^1$ is phenyl and is substituted with 0-3 substituents selected from cyano, halo, alkyl, haloalkyl, and haloalkoxy;
$Ar^2$ is pyridinyl or pyrimdinyl, and is substituted with 1 OR substituent and with 0-2 halo or alkyl substituents;
R is hydrogen or a prodrug moiety selected from the group consisting of alkyl esters, amino acid esters, alkoxy esters, phosphonic acids, phosphonic alkyl esters, alkoxyphosphonate acid, alkoxyphosphonate alkyl esters, alkyl carabamates, amino acid carbamates, alkyl phosporamidates, aryl phosphoramidates, and sulfamates;
X is a bond or $C_1$-$C_3$ alkylene;
n is 1 or 2;
ring A is piperazinyl, homopiperazinyl, or 2,5-diazabicyclo[2.2.1]heptanes, piperazin-2-one and is substituted with 0-4 substituents selected from halo, alkyl, hydroxy, or alkoxy;
or a pharmaceutically acceptable salt thereof.

DESCRIPTION

It will be understood that any given exemplary embodiment can be combined with one or more additional exemplary embodiments.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. Terms with a hydrocarbon moiety (e.g. alkoxy) include straight and branched isomers for the hydrocarbon portion. "Halo" includes fluoro, chloro, bromo, and iodo. "Haloalkyl" and "haloalkoxy" include all halogenated isomers from monohalo to perhalo. "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R. The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc. Some Formula I compounds contain at least one asymmetric carbon atom, an example of which is shown below. The invention includes all stereoisomeric forms of the compounds, both mixtures and separated isomers. Mixtures of stereoisomers can be separated into individual isomers by methods known in the art. The compounds include all tautomeric forms.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The abbreviations used in the present application are well-known to those skilled in the art.

One aspect of the invention is a compound of formula I

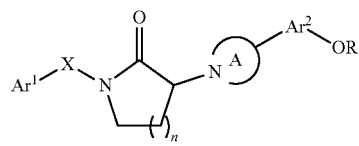

where:
Ar$^1$ is phenyl and is substituted with 0-3 substituents selected from cyano, halo, alkyl, haloalkyl, and haloalkoxy;
Ar$^2$ is pyridinyl or pyrimdinyl, and is substituted with 1 OR substituent and with 0-2 halo or alkyl substituents;
R is hydrogen or a prodrug moiety selected from the group consisting of alkyl esters, amino acid esters, alkoxy esters, phosphonic acids, phosphonic alkyl esters, alkoxyphosphononate acid, alkoxyphosphonate alkyl esters, alkyl carabamates, amino acid carbamates, alkyl phosporamidates, aryl phosphoramidates, and sulfamates;
X is a bond or C$_1$-C$_3$ alkylene;
n is 1 or 2;
ring A is piperazinyl, homopiperazinyl, or 2,5-diazabicyclo[2.2.1]heptanes, piperazin-2-one and is substituted with 0-4 substituents selected from halo, alkyl, hydroxy, or alkoxy;
or a pharmaceutically acceptable salt thereof.

Another aspect of the invention is a compound of formula I where n is 1 and ring A is piperazinyl substituted with 0-2 alkyl substituents.

Another aspect of the invention is a compound of formula I where Ar$^1$ is phenyl substituted with 0-3 substituents selected from cyano, halo, alkyl, haloalkyl, and haloalkoxy.

Another aspect of the invention is a compound of formula I where Ar$^2$ is selected from

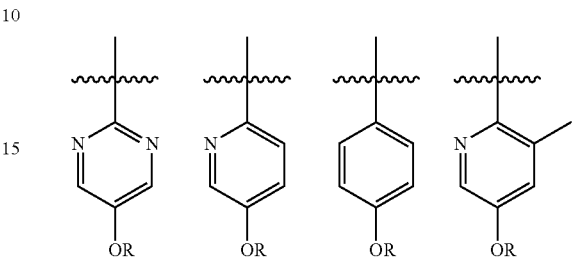

and R is selected from hydrogen, amino acid esters, phosphonic acids, alkoxyphosphononate acid, alkyl carabamates, amino acid carbamates, alkyl phosporamidates, aryl phosphoramidates, and sulfamates.

Another aspect of the invention is a compound of formula I where X is methylene.

Another aspect of the invention is a compound of formula I where R is hydrogen.

Another aspect of the invention is a compound of formula I where R is P(=O)(OH)$_2$.

Another aspect of the invention is a compound of formula I selected from the group consisting of:

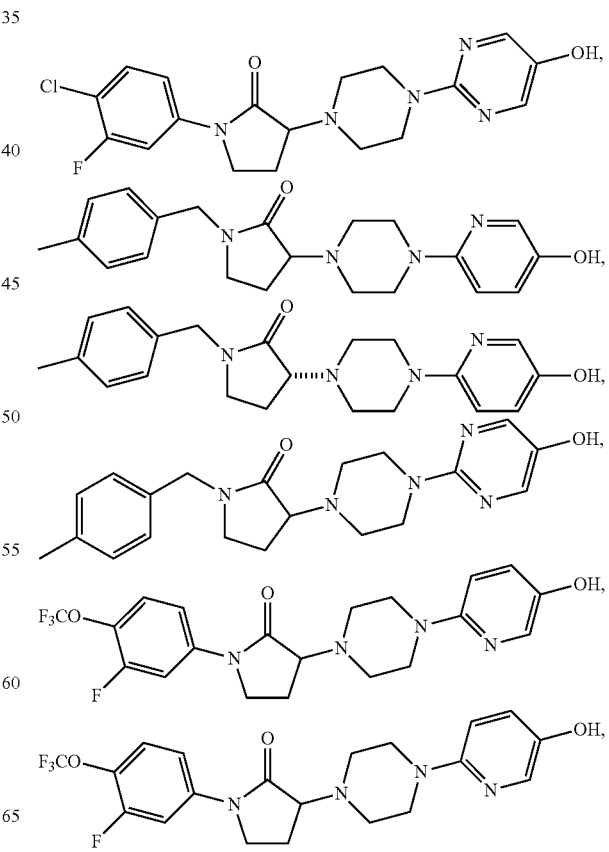

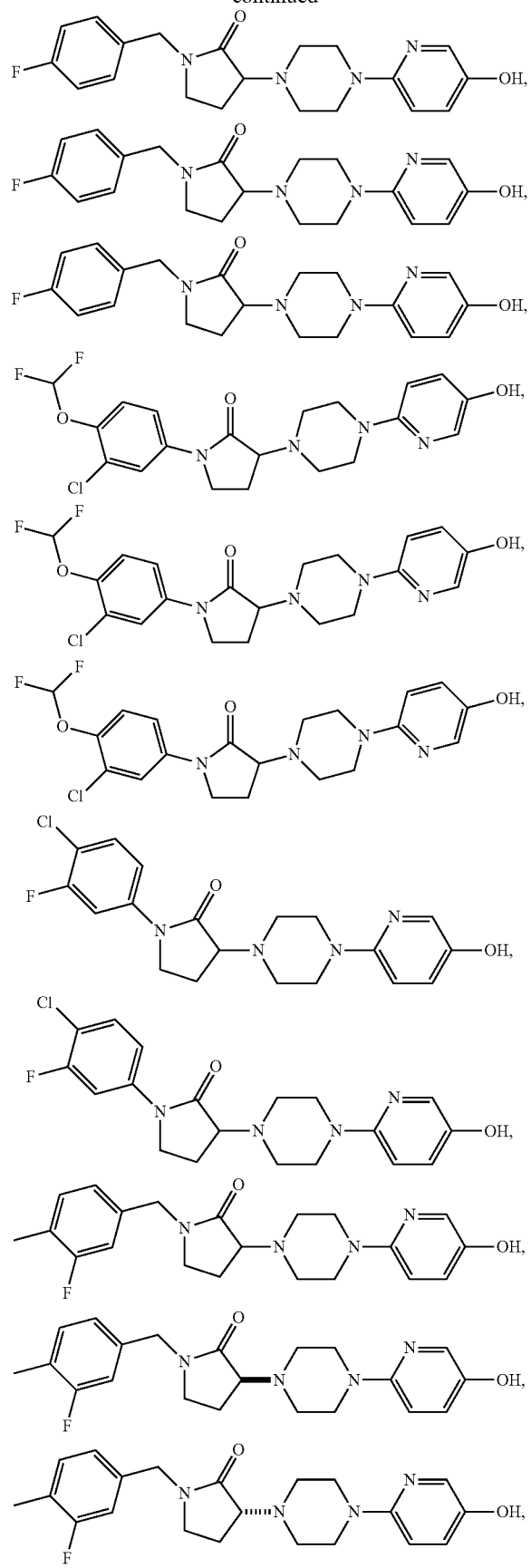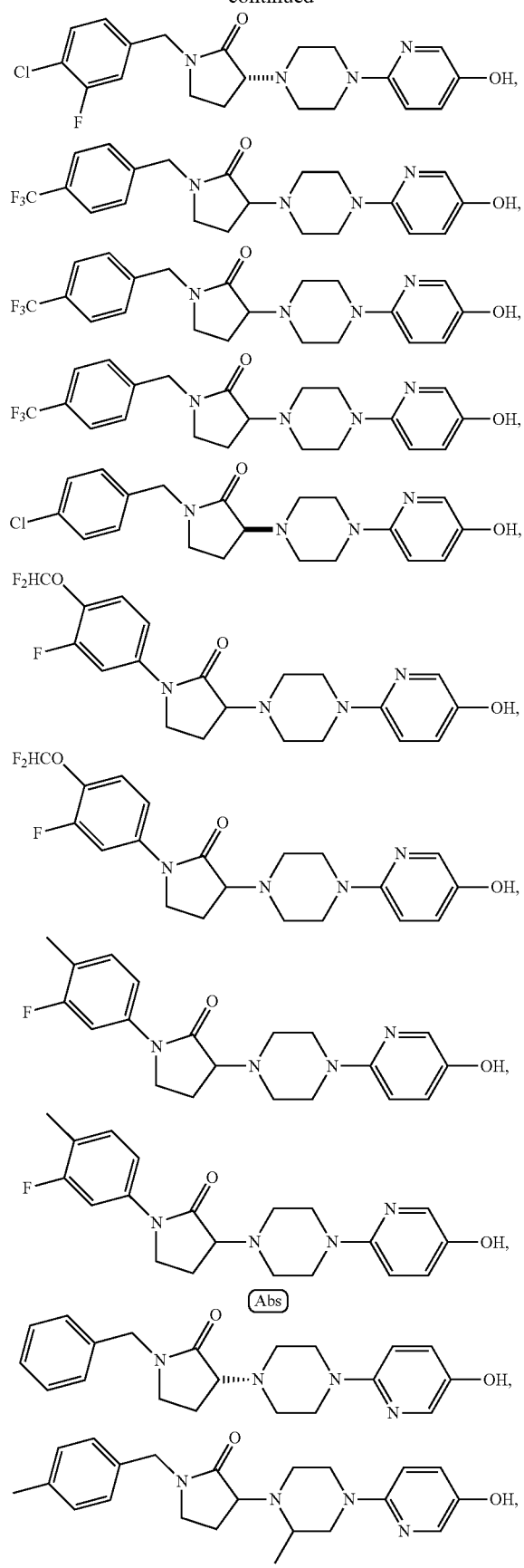

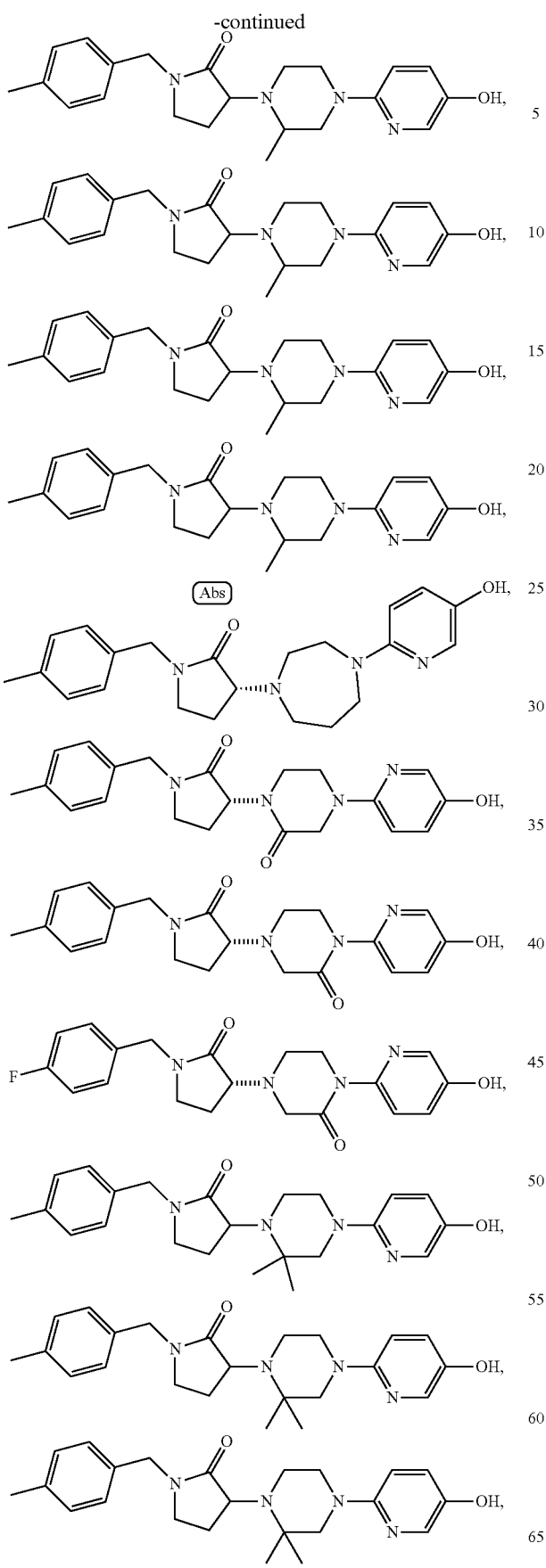
or a pharmaceutically acceptable salt thereof.

In a second aspect, a pharmaceutical composition comprising a compound of formula I or a pharmaceutically acceptable salt thereof and a pharmaceutically acceptable carrier.

In a third aspect, a method for the treatment of depression, Alzheimer's disease, neuropathic pain, or Parkinson's disease, which comprises administering to a patient a therapeutically affective amount of a compound of formula I.

In a second embodiment of the third aspect, the compound of formula I, directed to the treatment of depression.

In a third embodiment of the third aspect, the compound of formula I is directed to the treatment of Alzheimer's disease.

In a fourth embodiment of the third aspect, the compound of formula I is directed to the treatment of neuropathic pain.

EXAMPLES

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The compounds of the present disclosure may be prepared using the reactions and techniques described in this section, as well as, other synthetic methods known to those of ordinary skill in the art. The reactions are performed in solvents appropriate to the reagents and materials employed and suitable for the transformation being affected. Also, in the description of the synthetic methods described below, it is to be understood that all proposed reaction conditions, including choice of solvents, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

In a preferred embodiment of the invention, the synthesis of the compounds of instant disclosure can be set forth in the following schematic representations.

Scheme 1:

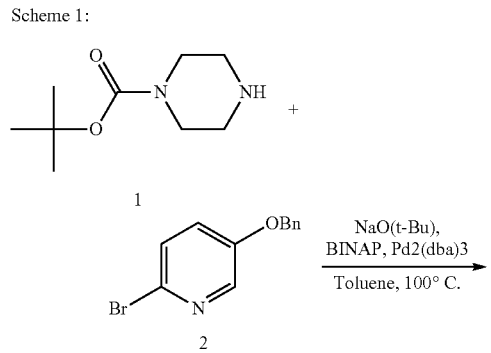

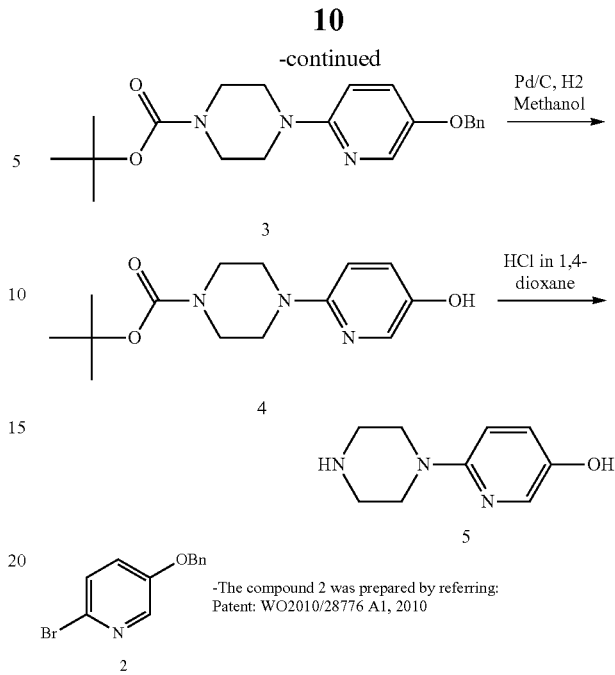

-The compound 2 was prepared by referring:
Patent: WO2010/28776 A1, 2010

Step 1: tert-butyl 4-(5-(benzyloxy)pyridin-2-yl)piperazine-1-carboxylate

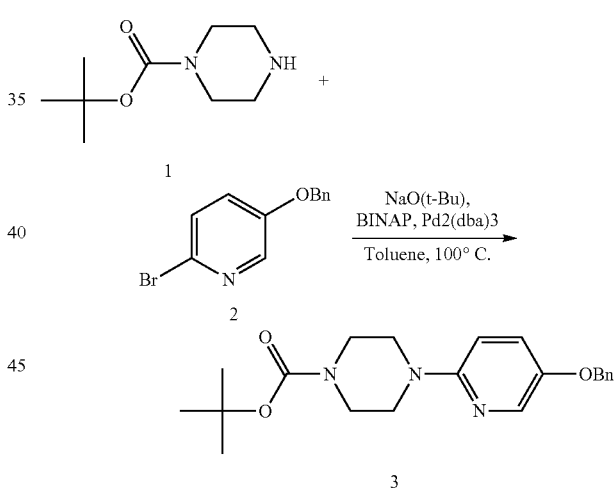

To a stirred solution of tert-butyl piperazine-1-carboxylate (5.99 g, 32.2 mmol) in Toluene (100 mL) was added 5-(benzyloxy)-2-bromopyridine (8.5 g, 32.2 mmol), SODIUM TERT-BUTOXIDE (7.73 g, 80 mmol) and BINAP (4.01 g, 6.44 mmol) at RT and the reaction mixture was purged with N2 for 15 min, followed by the addition of Pd$_2$(dba)$_3$ (2.95 g, 3.22 mmol). The reaction mixture was heated at 100° C. for 18 h. The completion of the reaction was monitored by LCMS. The reaction mixture was filtered through celeite and was washed with ethyl acetate (200 ml); the filtrate was concentrated to remove ethyl acetate and toluene. The residue was added water (250 ml) and the product was extracted with ethyl acetate (3*100 mL), the combined organic layer was dried over anhydrous sodium sulphate, filtered and concentrated to get crude 20 g. The crude product was purified by ISCO using 120 g silica gel column, the product was eluted with 40% ethyl acetate in pet ether to get tert-butyl 4-(5-(benzyloxy)pyridin-2-yl)piperazine-1-carboxylate (5 g, 12.99 mmol, 40.4% yield) as yellow solid.

LCMS: Buffer:10 mM Ammonium Acetate pH −5 adjusted with HCOOH, Mobile phase A:Buffer:ACN (95:5), Mobile phase B:Buffer:ACN (5:95), Method:% B: O min-5%:1.1 min-95%:1.7 min-95% Column Name: Acquity BEH C18 (2.1×50 mm) 1.7 u Method:C:\MassLynx, Flow: 0.8 ml/min, RT–1.28 min, M(+1)–370.

Step 2: tert-butyl 4-(5-hydroxypyridin-2-yl)piperazine-1-carboxylate

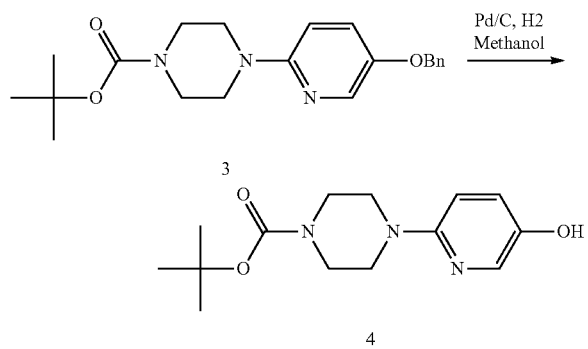

To a stirred solution of tert-butyl 4-(5-(benzyloxy)pyridin-2-yl)piperazine-1-carboxylate (2.00 g, 5.41 mmol) in Methanol (10 mL) was added Pd/C (0.576 g, 5.41 mmol), stirred under hydrogen bladder pressure through vaccume bend and was stirred at RT for 18 h. The completion of the reaction was monitored by LCMS. The reaction mixture was filtered through celeite and filtrate was concentrated to get tert-butyl 4-(5-hydroxypyridin-2-yl)piperazine-1-carboxylate (1.4 g, 5.01 mmol, 93% yield) as brown gummy material.

LCMS: % B: O min-2%:1.0 min-98%:1.6 min-98%, Mobile phase B: Acetonitrile, Mobile phase A:0.1% TFA in water, Method:C:\MassLynx, RT–0.64 min, M(+1)–280.

Step 3: 6-(piperazin-1-yl)pyridin-3-ol, HCl

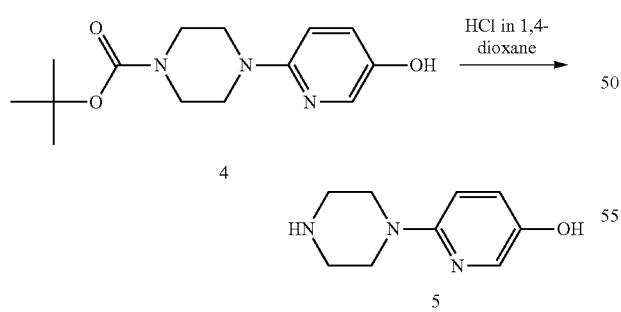

To a stirred solution of tert-butyl 4-(5-hydroxypyridin-2-yl) piperazine-1-carboxylate (1.5 g, 5.37 mmol) in 1,4-Dioxane (15 mL) was added 4M HCl in 1,4-dioxane (5 mL, 5.37 mmol) at RT. The reaction mixture was stirred at RT for 12 hrs. The completion of the reaction was monitored by LCMS. The reaction mixture was concentrated to get 6-(piperazin-1-yl) pyridin-3-ol, HCl (1 g, 4.08 mmol, 76% yield) as off white solid.

LCMS: Buffer:10 mM Ammonium Acetate pH −5 adjusted with HCOOH, Mobile phase A:Buffer:ACN (95:5), Mobile phase B:Buffer:ACN (5:95), Method:% B: O min-5%:1.1 min-95%:1.7 min-95% Column Name: Acquity BEH C18 (2.1×50 mm) 1.7 u Method:C:\MassLynx, Flow: 0.8 ml/min, RT–0.35 min, M(+1)–180.

Scheme 2:

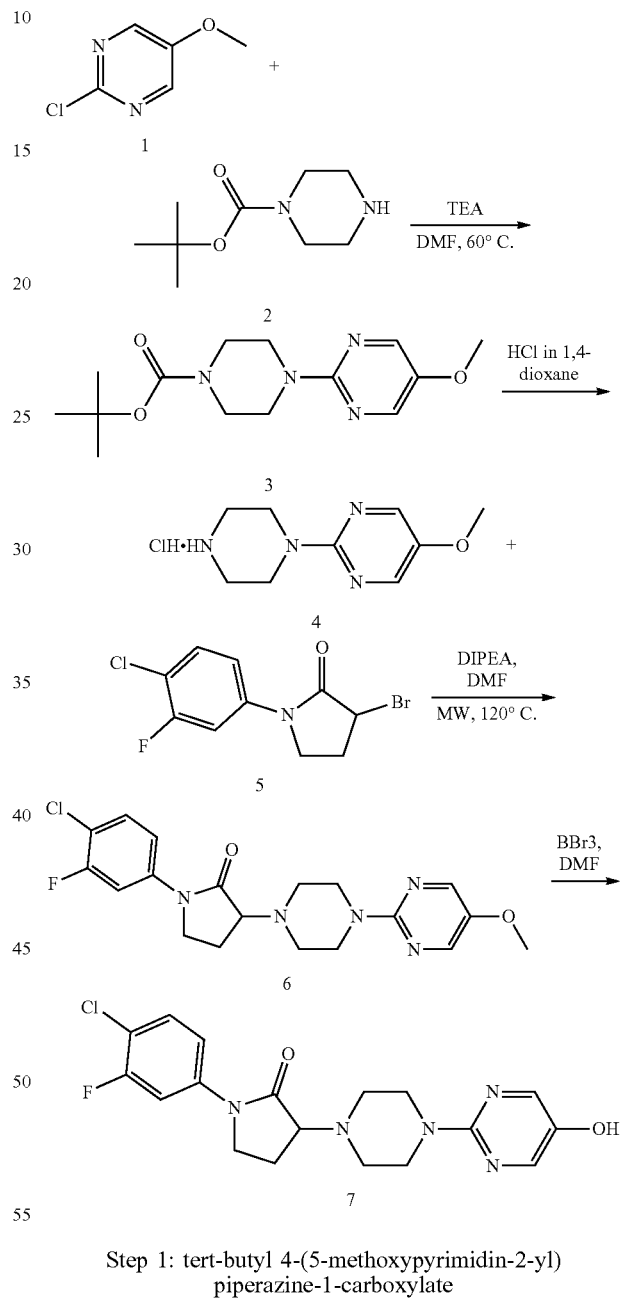

Step 1: tert-butyl 4-(5-methoxypyrimidin-2-yl) piperazine-1-carboxylate

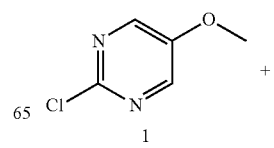

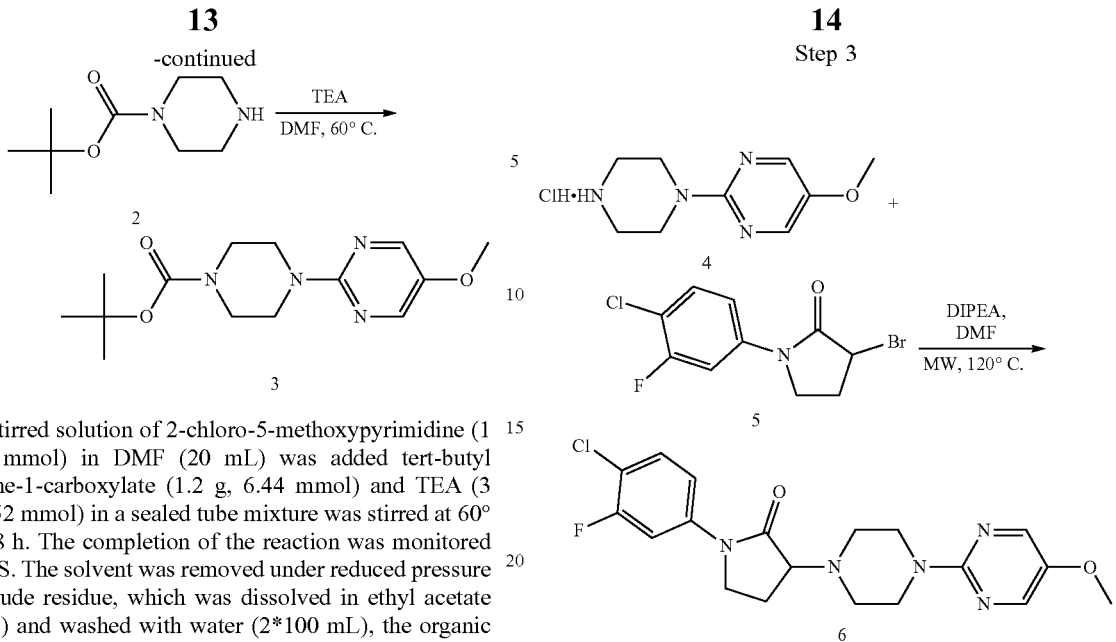

To a stirred solution of 2-chloro-5-methoxypyrimidine (1 g, 6.92 mmol) in DMF (20 mL) was added tert-butyl piperazine-1-carboxylate (1.2 g, 6.44 mmol) and TEA (3 mL, 21.52 mmol) in a sealed tube mixture was stirred at 60° C. for 48 h. The completion of the reaction was monitored by LCMS. The solvent was removed under reduced pressure to get crude residue, which was dissolved in ethyl acetate (100 mL) and washed with water (2*100 mL), the organic layer was dried over anhydrous sodium sulphate, filtered and evaporated under reduced pressure to get crude (1.5 g) as brown liquid. The crude compound was purified by combi (24 g silica gel column, eluted with 15% ethyl acetate/Pet ether) to get tert-butyl 4-(5-methoxypyrimidin-2-yl)piperazine-1-carboxylate (550 mg, 1.738 mmol, 25.1% yield) as off white solid.

LCMS: Column-Ascentis Express C18 (50×2.1 mm-2.7 μm), Mphase A: 10 mM NH4COOH IN WATER:ACN (98:02), Mphase B: 10 mM NH4COOH IN WATER:ACN(02:98), Flow=1 ML/MIN, Time: % B::0.0:0.0::1.7:100.0::3.0:100.0::3.2:0.0, LCMS RT=2.2 min M(+1)–295.

Step 2

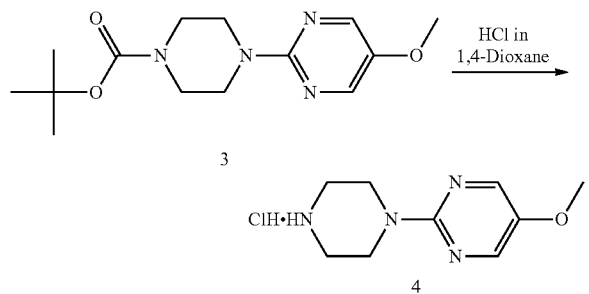

To a stirred solution of tert-butyl 4-(5-methoxypyrimidin-2-yl)piperazine-1-carboxylate (330 mg, 1.121 mmol) in 1,4-Dioxane (10 mL) at 0° C. was added HCl in 1,4 dioxane (1.121 mL, 1.121 mmol). The reaction mixture was stirred at RT for 12 h. The completion of the reaction was monitored through LCMS. The solvent was removed under reduced pressure to get crude compound which was triturated with ethyl acetate (2*10 mL) and the solid obtained was filtered to get 5-methoxy-2-(piperazin-1-yl)pyrimidine hydrochloride (200 mg, 0.607 mmol, 54.1% yield) as off white solid.

LCMS: Column-Ascentis Express C18 (50×2.1 mm-2.7 μm), Mphase A: 10 mM NH4COOH IN WATER:ACN(98:02), Mphase B: 10 mM NH4COOH IN WATER:ACN(02:98), Flow=1 ML/MIN, Time: % B::0.0:0.0::1.7:100.0::3.0:100.0::3.2:0.0, RT=0.946 min, M (+1)–195.

Step 3

To a stirred solution of 5-methoxy-2-(piperazin-1-yl)pyrimidine hydrochloride (50 mg, 0.217 mmol) was added DIPEA (0.114 mL, 0.650 mmol) and 3-bromo-1-(4-chloro-3-fluorophenyl)pyrrolidin-2-one (95 mg, 0.325 mmol) in dry DMF (1.5 mL). The reaction mixture was heated under MW at 120° C. for 90 minutes. The completion of the reaction was monitored by LCMS. The reaction mixture was concentrated under reduced pressure to get 1-(4-chloro-3-fluorophenyl)-3-(4-(5-methoxypyrimidin-2-yl)piperazin-1-yl)pyrrolidin-2-one (60 mg, 0.093 mmol, 43% yield) crude compound with 63% purity by LCMS, which was used to next step without purification.

LCMS: Column-Ascentis Express C18 (50×2.1 mm-2.7 μm), Mphase A: 10 mM NH4COOH IN WATER:ACN(98:02), Mphase B: 10 mM NH4COOH IN WATER:ACN(02:98), Flow=1 ML/MIN, Time: % B::0.0:0.0::1.7:100.0::3.0:100.0::3.2:0.0, RT–2.2 min, M (+1)–406.

Scheme 3:

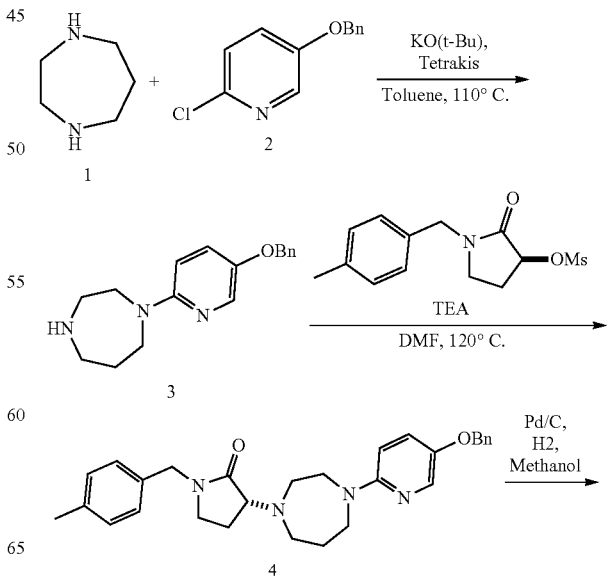

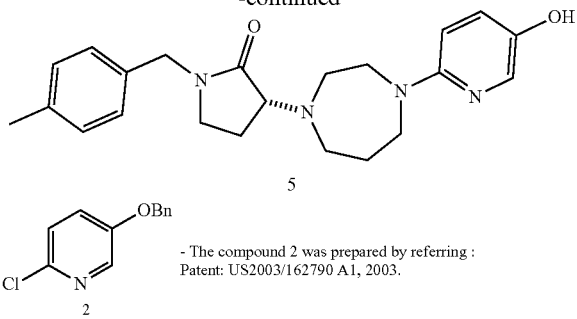

5

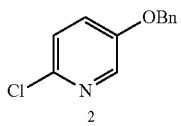

- The compound 2 was prepared by referring: Patent: US2003/162790 A1, 2003.

Step 1: 1-(5-(benzyloxy)pyridin-2-yl)-1,4-diazepane

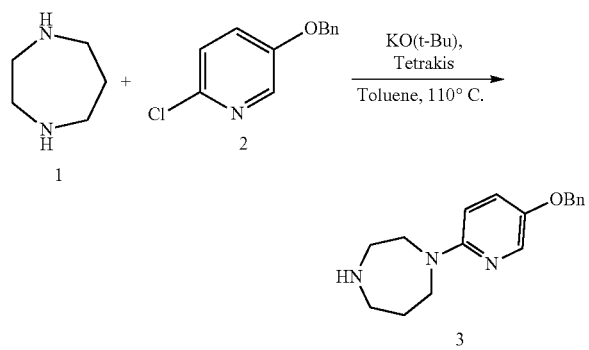

To stirred solution of 1,4-diazepane (4.10 g, 41.0 mmol) in Toluene (10 mL) was added 5-(benzyloxy)-2-chloropyridine (3.00 g, 13.66 mmol) and POTASSIUM TERT-BUTOXIDE (3.06 g, 27.3 mmol) at RT. The reaction mixture was purged with N2 for 15 minutes followed by the addition of Tetrakis (1.578 g, 1.366 mmol) at RT. The reaction mixture was heated at 110° C. for 4 h. The completion of the reaction was monitored by LCMS. The reaction mixture was filtered through celeite and the filtrate was concentrated to get crude 9 g. The crude product was purified by ISCO using 40 g basic alumina column, the product was eluted with 75% ethyl acetate in pet ether to get 1-(5-(benzyloxy)pyridin-2-yl)-1,4-diazepane (1.5 g, 4.29 mmol, 31.4% yield) as brown gummy material.

LCMS: % B: O min-2%:1.0 min-98%:1.6 min-98%, Mobile phase B: Acetonitrile, Mobile phase A:0.1% TFA in water, Method:C:\MassLynx, RT–0.66 min, M(+1)–284.

Step 2a

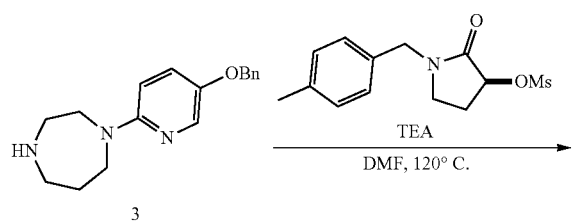

To a stirred solution of 1-(5-(benzyloxy)pyridin-2-yl)-1,4-diazepane (0.200 g, 0.169 mmol) in DMF (3 mL) was added TEA (0.071 mL, 0.508 mmol) and (S)-1-(4-methylbenzyl)-2-oxopyrrolidin-3-yl methanesulfonate (0.096 g, 0.339 mmol) at RT. The reaction mixture was stirred at 120° C. for 2 h in microwave. The completion of the reaction was monitored by LCMS. The reaction mixture was concentrated to get crude 0.45 g. The crude was purified by prep TLC; the plate was developed with ethyl acetate to get (R)-3-(4-(5-(benzyloxy)pyridin-2-yl)-1,4-diazepan-1-yl)-1-(4-methylbenzyl)pyrrolidin-2-one (0.04 g, 0.085 mmol, 50.2% yield) as off white solid.

LCMS: Buffer:10 mM Ammonium Acetate pH –5 adjusted with HCOOH, Mobile phase A:Buffer:ACN (95:5), Mobile phase B:Buffer:ACN (5:95), Method:% B: O min-5%:1.1 min-95%:1.7 min-95% Column Name: Acquity BEH C18 (2.1×50 mm) 1.7 u Method:C:\MassLynx, Flow: 0.8 ml/min, RT–1.3 min, M(+1)–471.

Step 2b

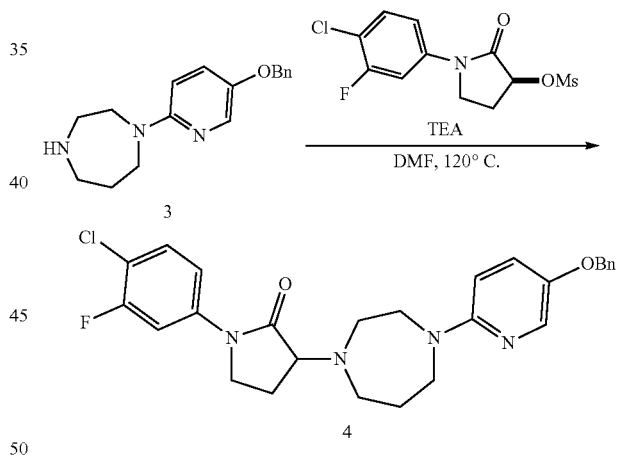

To a stirred solution of 1-(5-(benzyloxy)pyridin-2-yl)-1,4-diazepane (0.05 g, 0.176 mmol) in DMF (3 mL) was added TEA (0.074 mL, 0.529 mmol) and 1-(4-chloro-3-fluorophenyl)-2-oxopyrrolidin-3-yl methanesulfonate (0.081 g, 0.265 mmol) at RT. The reaction mixture was stirred at 120° C. for 2 h in microwave. 28% desired product mass by LCMS. The reaction mixture was concentrated under high vacuum to get crude 3-(4-(5-(benzyloxy)pyridin-2-yl)-1,4-diazepan-1-yl)-1-(4-chloro-3-fluorophenyl)pyrrolidin-2-one (0.2 g, 0.113 mmol, 64.1% yield) as brown gummy and the crude as such was taken for next step without further purification.

LCMS: Buffer:10 mM AmmoniumAcetate pH –5 adjusted with HCOOH, Mobile phase A:Buffer:ACN (95:5), Mobile phase B:Buffer:ACN (5:95), Method:% B: O min-5%:1.1 min-95%:1.7 min-95% Column Name: Acquity BEH C18 (2.1×50 mm) 1.7 u Method:C:\MassLynx, Flow: 0.8 ml/min, rt–1.25 min, M(+1)–495.

Scheme 4:

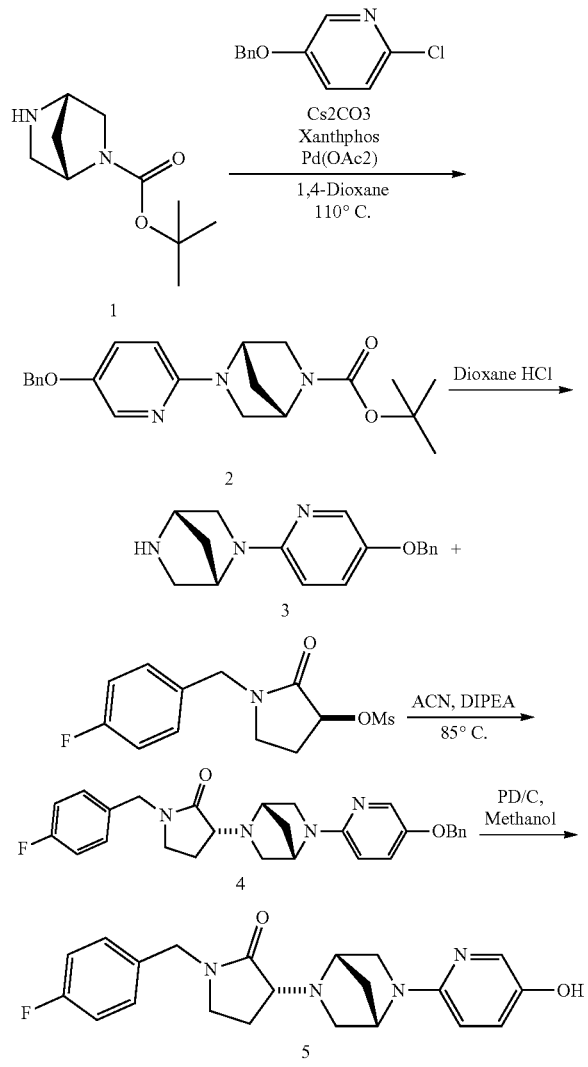

Step 1: (1S,4S)-tert-butyl 5-(5-(benzyloxy)pyridin-2-yl)-2,5-diazabicyclo[2.2.1]heptane-2-carboxylate

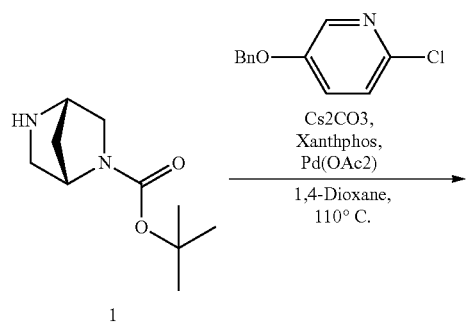

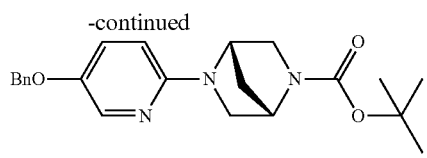

To a solution of (1S,4S)-tert-butyl 2,5-diazabicyclo[2.2.1]heptane-2-carboxylate (2.5 g, 12.61 mmol) in 1,4-Dioxane (50 mL) was added 5-(benzyloxy)-2-chloropyridine (3.05 g, 13.87 mmol) and CESIUM CARBONATE (8.22 g, 25.2 mmol). The reaction mixture was degassed with nitrogen for 15 minutes then was added XANTPHOS (1.094 g, 1.891 mmol) followed by PdOAc$_2$ (0.283 g, 1.261 mmol) and heated to 110° C. for overnight. The completion of the reaction was monitored by LCMS. Reaction mass was filtered through celite and was washed with ethyl acetate (100 mL). The filtrate was concentrated under vacuum to get crude 5.5 g. The crude was purified by ISCO system (25% EA:Hexane, 40 g silica gel column) to afford (1S,4S)-tert-butyl 5-(5-(benzyloxy)pyridin-2-yl)-2,5-diazabicyclo[2.2.1]heptane-2-carboxylate (0.8 g, 2.097 mmol, 16.63% yield) as yellow solid.

LCMS: Column-Ascentis Express C18 (50×2.1 mm-2.7 μm), Mphase A: 10 mM Ammonium Acetate in water, Mphase B: CAN, Flow=1 ML/MIN, Time: % A: % B::0.0:100.0:0.0::1.7:0.0:100.0::3.2:0.0:100.0, RT–2.505 min, M(+1)–382.

Step 2: (1S,4S)-2-(5-(benzyloxy)pyridin-2-yl)-2,5-diazabicyclo[2.2.1]heptane

To a solution of (1S,4S)-tert-butyl 5-(5-(benzyloxy)pyridin-2-yl)-2,5-diazabicyclo[2.2.1]heptane-2-carboxylate (0.8 g, 2.097 mmol) in 1,4-Dioxane (5 mL) was added 4 M HCl in Dioxane (5 mL, 20.00 mmol) and stirred at RT for overnight. The completion of the reaction was monitored by LCMS. The reaction mass was concentrated under vacuum to get crude solid. The solid was triturated with ethyl acetate (2×50 mL). To the solid compound 10% sodium bicarbonate solution (50 mL) was added and the product was extracted with ethylacetate (3×50 mL), the combined organic layer was dried over sodium sulphate, filtered and concentrated under vacuum to get (1S,4S)-2-(5-(benzyloxy)pyridin-2-yl)-2,5-diazabicyclo[2.2.1]heptane (0.5 g, 1.066 mmol, 50.8% yield) as brown solid.

LCMS: Column-Ascentis Express C$_8$ (50×2.1 mm-2.7 μm), Mphase A: 2% ACN—98% H20-10 mM NH4C00H, Mphase B: 98% ACN—2% H20-10 mM NH4C00H, Flow=1 ML/MIN, Time: % B::0.0:0.0::1.7:100.0::4.0:100.0, RT–1.726 min, M (+1)–282.

Step 3: (R)-3-((1S,4S)-5-(5-(benzyloxy)pyridin-2-yl)-2,5-diazabicyclo[2.2.1]heptan-2-yl)-1-(4-fluorobenzyl)pyrrolidin-2-one

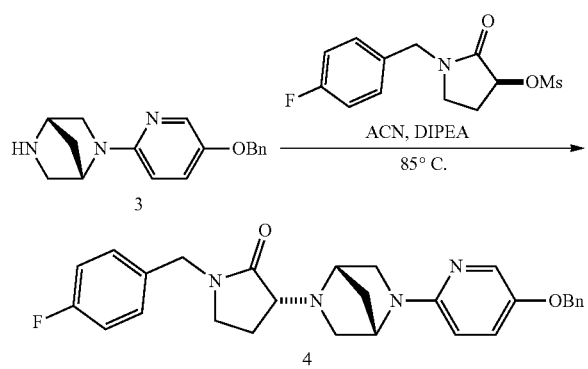

To a solution of (1S,4S)-2-(5-(benzyloxy)pyridin-2-yl)-2,5-diazabicyclo[2.2.1]heptane (0.075 g, 0.267 mmol) in Acetonitrile (3 mL) was added DIPEA (0.140 mL, 0.800 mmol) and (S)-1-(4-fluorobenzyl)-2-oxopyrrolidin-3-yl methanesulfonate (0.115 g, 0.400 mmol) then heated to 85° C. for overnight. The reaction mass was concentrated under reduced pressure and partitioned between sodium bicarbonate (10%) solution (50 mL) and ethylacetate (50 mL), the organic layer was dried over sodium sulfate and concentrated under vacuum to get (R)-3-((1S,4S)-5-(5-(benzyloxy)pyridin-2-yl)-2,5-diazabicyclo[2.2.1]heptan-2-yl)-1-(4-fluorobenzyl)pyrrolidin-2-one (0.18 g, 0.194 mmol, 72.9% yield) as brown gummy.

LCMS: % B: O min-2%:1.0 min-98%:1.6 min-98%, Mobile phase B: Acetonitrile, Mobile phase A:0.1% TFA in water, Method:C:\MassLynx, RT–1.21 min, M(+1)–473.

Scheme 5:

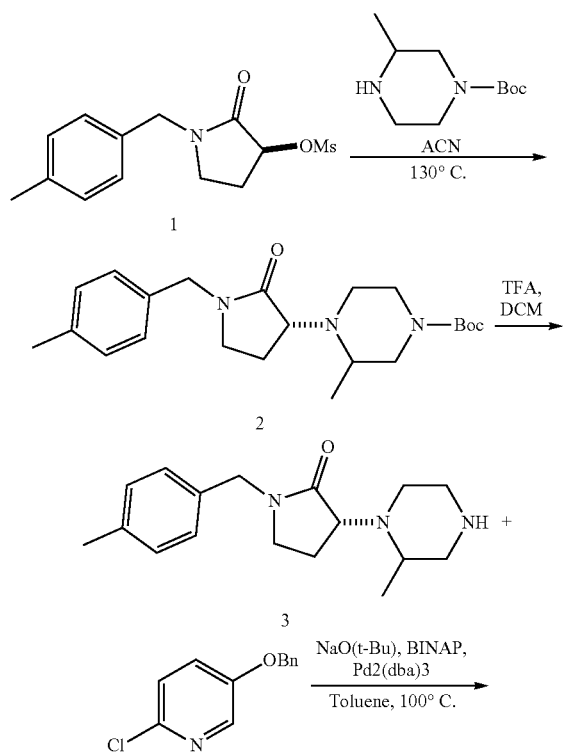

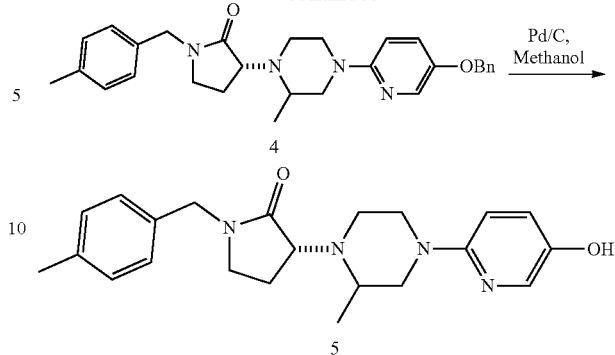

Step 1: tert-butyl 3-methyl-4-((R)-1-(4-methylbenzyl)-2-oxopyrrolidin-3-yl)piperazine-1-carboxylate

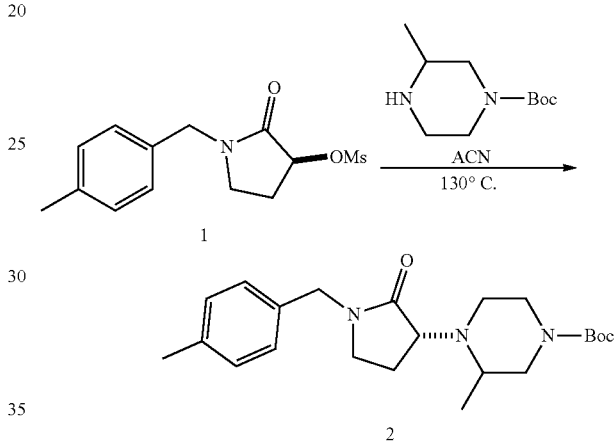

To a solution of tert-butyl 3-methylpiperazine-1-carboxylate (0.530 g, 2.65 mmol) in Acetonitrile (30 mL) added (S)-1-(4-methylbenzyl)-2-oxopyrrolidin-3-yl methanesulfonate (1.5 g, 5.29 mmol) and raised the temperature to 130° C. for 2 h. The reaction mixture was diluted with water (30 mL) and extracted with ethyl acetate (2×50 mL). The combined organic layer was dried over sodiumsulphate and concentrated under reduced pressure. The crude was purified over C18, 40 g Reverse phase Combiflash eluted with 80% Acetonitrile+20% 10 mm Ammonium acetate mixture to get crude tert-butyl 3-methyl-4-((R)-1-(4-methylbenzyl)-2-oxopyrrolidin-3-yl)piperazine-1-carboxylate (950 mg, 2.255 mmol, 85% yield) as off white solid.

LCMS: RT: 2.368 min ACN/H$_2$O with HCOONH$_4$, Ascentis Express C18 (50×2.1 mm-2.7 µm), gradient=1.7 min, wavelength=220 nm; MS (ES): m/z 388. M+H.

Step 2: 1-(4-methylbenzyl)-3-(2-methylpiperazin-1-yl)pyrrolidin-2-one, TFA

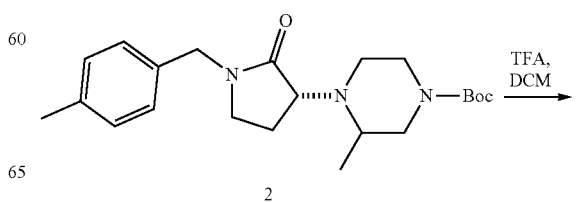

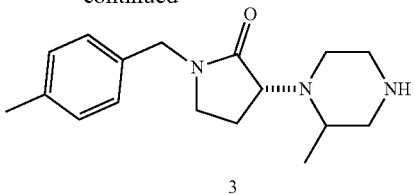

3

To a stirred solution of tert-butyl 3-methyl-4-(1-(4-methylbenzyl)-2-oxopyrrolidin-3-yl)piperazine-1-carboxylate (1 g, 2.58 mmol) in DCM (25 mL) was added TFA (1.988 mL, 25.8 mmol) at RT. The reaction mixture was stirred at RT for 2 h. The completion of the reaction was monitored by LCMS. The reaction mixture was evaporated under reduced pressure and washed with diethyl ether (20 mL) and the solid was dried under reduced pressure to get 1-(4-methylbenzyl)-3-(2-methylpiperazin-1-yl)pyrrolidin-2-one, TFA (856 mg, 1.919 mmol, 74.4% yield).

LCMS: ACN/H$_2$O with HCOONH$_4$, Ascentis Express C18 (50×2.1 mm-2.7 μm), gradient–1.7 min, wavelength–220 nm, RT–1.75 min, M (+1)–288.

Step 3

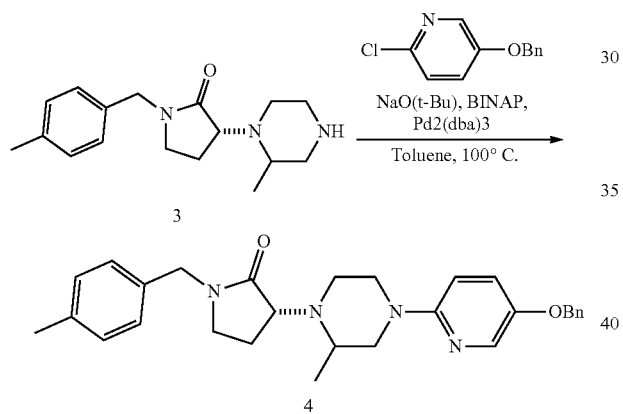

To a stirred solution of 5-(benzyloxy)-2-chloropyridine (650 mg, 2.96 mmol) was added 1-(4-methylbenzyl)-3-(2-methylpiperazin-1-yl)pyrrolidin-2-one (850 mg, 0.696 mmol), BINAP (43.3 mg, 0.070 mmol) and SODIUM TERT-BUTOXIDE (201 mg, 2.088 mmol). The reaction mixture was purged with nitrogen for 10 minutes then was added Pd$_2$(dba)$_3$ (51.0 mg, 0.056 mmol). The reaction mixture was stirred at 110° C. for 18 h. The completion of the reaction was monitored by LCMS. The reaction mixture was diluted with saturated ammonium chloride solution and extracted with ethyl acetate (100 mL). The organic layer was dried over Na2SO4, filtered and evaporated under reduced pressure to get crude 1.5 g. The crude was purified over C18 (24 gms, Rreverse phase column, silicycle) eluted with 40% Acetonitrile in 10 mm ammonium acetate to get 3-(4-(5-(benzyloxy)pyridin-2-yl)-2-methylpiperazin-1-yl)-1-(4-methylbenzyl)pyrrolidin-2-one (650 mg, 0.994 mmol, 33.6% yield) as pale yellow liquid with 72% purity by LCMS.

LCMS: Column-Ascentis Express C18 (50×2.1 mm-2.7 μm), Mphase A: 10 mM NH4C00H IN WATER:ACN(98:02), Mphase B: 10 mM NH4C00H IN WATER:ACN(02:98), Flow=1 ML/MIN, Time: % B::0.0:0.0::1.7:100.0::3.0:100.0, 3.2:0.0, RT–2.489 min, M(+1)–471.

Scheme 6:

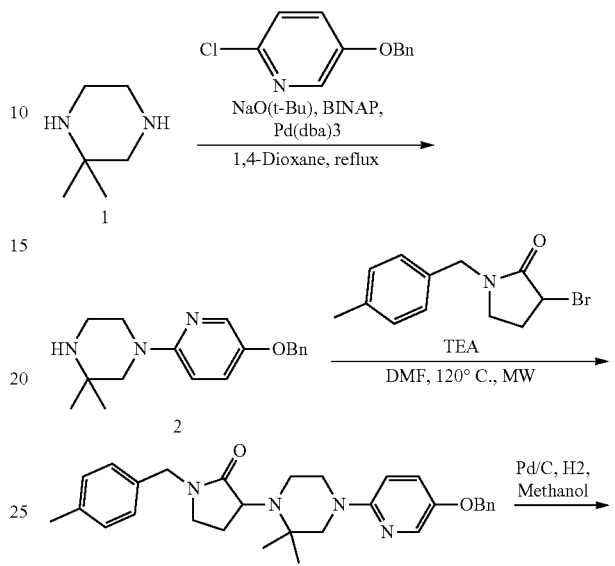

Step 1: 1-(5-(benzyloxy)pyridin-2-yl)-3,3-dimethyl-piperazine

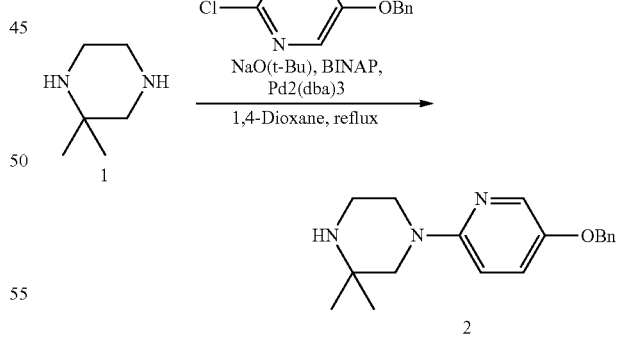

To a solution of 5-(benzyloxy)-2-chloropyridine (1.731 g, 7.88 mmol) in 1,4-Dioxane (20 mL) was added 2,2-dimethylpiperazine (1 g, 8.76 mmol), BINAP (0.545 g, 0.876 mmol), SODIUM TERT-BUTOXIDE (2.104 g, 21.89 mmol). The reaction mixture was purged with Nitrogen for 15 minutes and was added Pd$_2$(dba)$_3$ (0.642 g, 0.701 mmol). The reaction mixture was refluxed for 5 h under nitrogen. The completion of the reaction was monitored by LCMS. The reaction mixture was diluted with water 50 mL and the product was extracted with ethyl acetate (3*50 mL). The combined organic layer was washed with brine solution (100 mL), dried over Na2SO4 and evaporated under reduced pressure to get crude residue 3 g. The crude was purified over 120 g C18 Redisep reverse phase column eluted with 40% Acetonitrile+60% 10 mm ammonium acetate to get 1-(5-(benzyloxy)pyridin-2-yl)-3,3-dimethylpiperazine (1.3 g, 4.33 mmol, 49.4% yield).

LCMS: ACN/H$_2$O with HCOONH$_4$, Ascentis Express C18 (50×2.1 mm-2.7 μm), gradient=1.7 min, wavelength=220 nm, RT–1.94 min, M(+1)–298.

Step 2: (R)-3-(4-(5-(benzyloxy)pyridin-2-yl)-2,2-dimethylpiperazin-1-yl)-1-(4-methylbenzyl)pyrrolidin-2-one

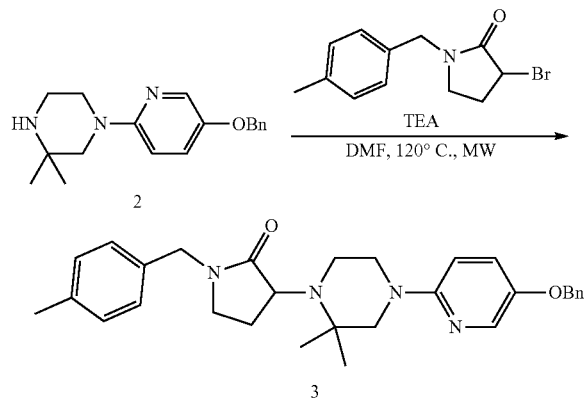

To a solution of 3-bromo-1-(4-methylbenzyl)pyrrolidin-2-one (135 mg, 0.504 mmol) in DMF (2 mL) was added 1-(5-(benzyloxy)pyridin-2-yl)-3,3-dimethylpiperazine (100 mg, 0.336 mmol) and TEA (0.047 mL, 0.336 mmol) at RT. The reaction mixture was heated at 120° C. for 1.5 h in CEM microwave. The completion of the reaction was monitored by LCMS. The reaction mixture was added water (25 mL) and the product was extracted with ethyl acetate (3*15 mL), the combined organic layer was dried over Na$_2$SO$_4$, filtered and evaporated under reduced pressure to get crude residue 0.3 g. The crude was subjected to Reverse phase purification C18, 24 gms silica gel column eluted with 80% Acetonitrile+20% 10 mm TFA to get (R)-3-(4-(5-(benzyloxy)pyridin-2-yl)-2,2-dimethylpiperazin-1-yl)-1-(4-methylbenzyl)pyrrolidin-2-one (25 mg, 0.046 mmol, 13.81% yield).

LCMS: ACN/H$_2$O with HCOONH$_4$, Ascentis Express C18 (50×2.1 mm-2.7 μm), gradient=1.7 min, wavelength=220 nm, RT–2.562 min, M(+1)–485.

General Intermediates

Example 1 (Racemate): 1-(4-chloro-3-fluorophenyl)-3-(4-(5-hydroxypyrimidin-2-yl)piperazin-1-yl)pyrrolidin-2-one

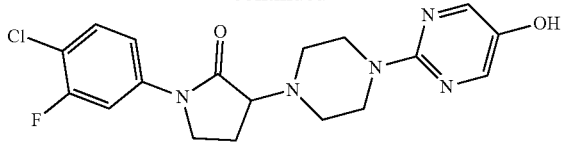

To a stirred solution of 1-(4-chloro-3-fluorophenyl)-3-(4-(5-methoxypyrimidin-2-yl) piperazin-1-yl) pyrrolidin-2-one (60 mg, 0.148 mmol) in DCM (8 mL) at −78° C. was slowly added BBr3 in DCM (5 mL, 5.00 mmol). The reaction mixture was stirred at RT for 12 h. The completion of the reaction was monitored through LCMS. The reaction mixture was cooled to 0° C. and quenched with saturated NaHCO$_3$ solution (25 mL). The product was extracted with DCM (2*25 mL), the combined organic layer was dried over anhydrous sodium sulphate, filtered and evaporation under reduced pressure to get crude compound. The crude compound was submitted to SCP. The crude material was purified via preparative LC/MS with the following conditions: Waters Xbridge C18, 19×150 mm, 5 μm; Guard Column: Waters XBridge C18, 19×10 mm, 5 μm; Mobile Phase A: 5:95 Acetonitrile:water with 10 mM NH$_4$OAc; Mobile Phase B: 95:5 Acetonitrile:water with 10 mM NH$_4$OAc; Gradient:5-35% B over 25 minutes, followed by a 10 minute hold at 35% B and 5 minute hold at 100% B; Flow:15 ml/min. Fractions containing the desired product were combined and dried using a Genevac centrifugal evaporator to get 1-(4-chloro-3-fluorophenyl)-3-(4-(5-hydroxypyrimidin-2-yl)piperazin-1-yl)pyrrolidin-2-one (29.1 mg, 0.148 mmol, 50.2% yield) as pale yellow solid. Two analytical LC/MS injections were used to determine the final purity.

Injection 1 conditions: Column: Ascentis Express C18 (50×2.1) mm, 2.7 μm; Mobile Phase A: 5:95 Acetonitrile:water with 10 mM NH4OAc; Mobile Phase B: 95:5 Acetonitrile:water with 10 mM NH4OAc; Temperature: 50° C.; Gradient: 0-100% B over 3 minutes; Flow: 1.1 ml/min.

Injection 2 conditions: Column: Ascentis Express C18 (50×2.1) mm, 2.7 μm; Mobile Phase A: 5:95 Acetonitrile:water with 0.1% TFA; Mobile Phase B: 95:5 Acetonitrile:water with 0.1% TFA; Temperature: 50° C.; Gradient: 0-100% B over 3 minutes; Flow: 1.1 ml/min.

LCMS: A: 95% Water: 5% Acetonitrile; 10 mM NH4OAC, B: 5% Water: 95% Acetonitrile; 10 mM NH4OAC, Flow: 1.1 ml/min, Temp: 50° C., Column: Ascentis Express C18 (50×2.1) mm, 2.7 μm, Time (min): 0-3, % B: 0-100, LCMS RT=1.34 min (M+H, 392).

$^1$H NMR: (400 MHz, METHANOL-d$_4$) □=8.03 (s, 2H), 7.87-7.81 (m, 1H), 7.54-7.39 (m, 2H), 3.90-3.70 (m, 7H), 3.04-2.95 (m, 2H), 2.76-2.68 (m, 2H), 2.39-2.31 (m, 1H), 2.27-2.16 (m, 1H).

Example 2 (P1 & P2)

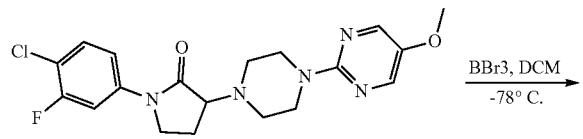

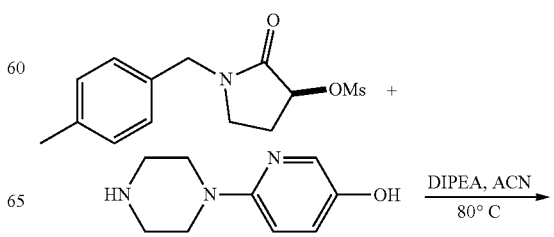

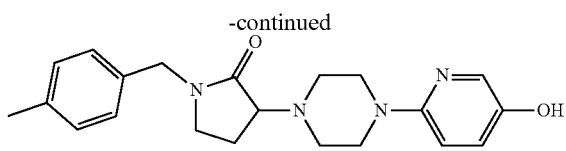

To a stirred solution of (S)-1-(4-methylbenzyl)-2-oxopyrrolidin-3-yl methanesulfonate (0.108 g, 0.382 mmol) in ACN (5 mL) was added 6-(piperazin-1-yl)pyridin-3-ol (0.057 g, 0.318 mmol) and DIPEA (0.139 mL, 0.795 mmol) and heated to 80° C. for 16 h. The completion of the reaction was monitored by LCMS. The reaction mixture was cooled to RT. The reaction mixture was diluted with water (15 mL), and the aqueous layer was separated and extracted with EtOAc (3×25 mL). The combined organic layers were washed with water (15 mL) and brine (15 mL) and dried over $Na_2SO_4$. The mixture was filtered, and the solvent was removed in vacuum to give the crude product. The crude compound was purified by SCP. The crude material was purified via preparative LC/MS with the following conditions: Waters Xbridge C18, 19×150 mm, 5 μm; Guard Column:Waters XBridge C18, 19×10 mm, 5 μm; Mobile Phase A:5:95 Acetonitrile:water with 10 mM NH4OAc; Mobile Phase B: 95:5 Acetonitrile:water with 10 mM NH4OAc; Gradient: 5-30% B over 25 minutes, followed by a 10 minute hold at 30% B and 5 minute hold at 100% B; Flow: 15 ml/min. Fractions containing the desired product were combined and dried using a Genevac centrifugal evaporator to get 2; 3-(4-(5-hydroxypyridin-2-yl)piperazin-1-yl)-1-(4-methylbenzyl)pyrrolidin-2-one (30 mg, 0.0816 mmol, 25.74% yield) as pale yellow solid. Two analytical LC/MS injections were used to determine the final purity.

Injection 1 conditions: Column: Ascentis Express C18 (50×2.1) mm, 2.7 μm; Mobile Phase A: 5:95 Acetonitrile:water with 10 mM NH4OAc; Mobile Phase B: 95:5 Acetonitrile:water with 10 mM NH4OAc; Temperature: 50° C.; Gradient:0-100% B over 3 minutes; Flow: 1.1 ml/min.

Injection 2 conditions: Column: Ascentis Express C18 (50×2.1) mm, 2.7 μm; Mobile Phase A: 5:95 Acetonitrile:water with 0.1% TFA; Mobile Phase B: 95:5 Acetonitrile:water with 0.1% TFA; Temperature: 50° C.; Gradient:0-100% B over 3 minutes; Flow:1.1 ml/min.

The chiral screening of compound 2 shows two peaks, indicates the racemization. The racemic mixture 2 was submitted for SFC for chiral separation. The fractions from SFC were collected and concentrated to get P1; (S)-3-(4-(5-hydroxypyridin-2-yl)piperazin-1-yl)-1-(4-methylbenzyl) pyrrolidin-2-one and P2; (R)-3-(4-(5-hydroxypyridin-2-yl) piperazin-1-yl)-1-(4-methylbenzyl)pyrrolidin-2-one.

The compound was registered as BMT-173283 01-003 (with 57% ee). BMT-173283-01-003 (98564-126-02) with 57% was purified by SFC Chiral screening: Injection Volume: 10, Co-Solvent: 0.3% DEA in Methanol, Column: Chiralcel OD-H (4.6×250) mm, 5 u, Column Temperature: 23.2, Total Flow: 3, CO2 Flow Rate: 1.8, Co-Solvent Flow Rate: 1.2, Co-Solvent %: 40, Back Pressure: 101.

| Peak Info: | | | | |
|---|---|---|---|---|
| Number | Peak Name | RT (min) | Area | Area % |
| 1 | Peak 1 | 3.37 | 431.3981 | 21.027 |
| 2 | Peak 2 | 4.82 | 1620.2377 | 78.973 |

SFC Purification Method:
Analytical SFC Conditions: Column/dimensions: Chiralcel OD-H (250×4.6) mm, 5 u, % CO2: 60%, % Co solvent: 40% (0.25% DEA in Methanol), Total Flow: 3.0 g/min, Back Pressure: 100 bar, Temperature: 25° C., UV: 244.

Preparative SFC Conditions: Column/dimensions: Chiralcel OD-H (250×21) mm, 5 u, % CO2: 60%, % Co solvent: 40% (0.25% DEA in Methanol), Total Flow: 75.0 g/min, Back Pressure: 100 bar, Temperature: 25° C., UV: 244, Peak number: Retention Time::Peak 1: 3.00::Peak 2: 4.00, Solubility: Methanol in 5 ml, Loadability/Inj: 9.00 mg/mL, Total No of injections: 15, Total Time for purification 1.0 hr, Instrument details: Make/Model: Thar SFC-80.

For P1 (Homochiral): (S)-3-(4-(5-hydroxypyridin-2-yl)piperazin-1-yl)-1-(4-methylbenzyl) pyrrolidin-2-one

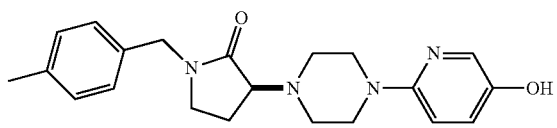 [SMILES: Cc1ccc(CN2CC[C@H](N3CCN(c4ccc(O)cn4)CC3)C2=O)cc1]

LCMS: Column-Ascentis Express C18 (50×2.1 mm-2.7 μm), Mphase A: 0.1% HCOOH in water, Mphase B: CAN, Flow=1 ML/MIN, Time: % A: % B::0.0:100.0:0.0::1.7:0.0:100.0::3.2:0.0:100.0, RT–1.669, M(+1)–367.

Chiral Purity: Injection Volume: 10, Co-Solvent: 0.3% DEA in Methanol, Column: Chiralcel OD-H (4.6×250) mm, 5 u, Column Temperature: 23.7, Total Flow: 3, CO2 Flow Rate: 1.8, Co-Solvent Flow Rate: 1.2, Co-Solvent %:40, Back Pressure: 99, RT–2.9 min.

1H NMR: 400 MHz, MeOD: δ 2.03-2.09 (m, 1H), 2.22 (t, J=7.60 Hz, 1H), 2.32 (s, 3H), 2.78 (t, J=11.20 Hz, 2H), 3.11 (t, J=21.20 Hz, 2H), 3.21-3.27 (m, 2H), 3.42-3.43 (m, 4H), 3.71 (t, J=17.20 Hz, 1H), 4.37 (d, J=14.80 Hz, 1H), 4.49 (d, J=14.40 Hz, 1H), 6.81 (d, J=10.00 Hz, 1H), 7.13-7.19 (m, 5H), 7.73 (d, J=2.80 Hz, 1H).

For P2 (Homochiral): (R)-3-(4-(5-hydroxypyridin-2-yl)piperazin-1-yl)-1-(4-methylbenzyl) pyrrolidin-2-one Chiral Purity: Injection Volume: 10, Co-Solvent: 0.3% DEA in Methanol, Column: Chiralcel OD-H (4.6×250) mm, 5 u, Column Temperature: 23.7, Total Flow: 3, CO2 Flow Rate: 1.8, Co-Solvent Flow Rate: 1.2, Co-Solvent %:40, Back Pressure: 99, RT–4.95 min.

LCMS: Column-Ascentis Express C8 (50×2.1 mm-2.7 μm), Mphase A: 2% ACN—98% H20-10 mM NH4C00H, Mphase B: 98% ACN—2% H20-10 mM NH4C00H, Flow=1 ML/MIN, Time: % A::0.0:0.0::1.5:100.0::3.2:100.0, RT–1.733, M(+1)–367.

1NMR: 400 MHz, MeOD: δ 2.01-2.08 (m, 1H), 2.15-2.20 (m, 1H), 2.32 (s, 3H), 2.67-2.73 (m, 2H), 2.98-3.03 (m, 2H), 3.19-3.26 (m, 2H), 3.38 (t, J=10.40 Hz, 4H), 3.62 (t, J=17.60 Hz, 1H), 4.36 (d, J=14.40 Hz, 1H), 4.49 (d, J=14.40 Hz, 1H), 6.77 (d, J=8.80 Hz, 1H), 7.13-7.73 (m, 5H), 7.73 (d, J=2.80 Hz, 1H).

Example 3 (Racemate): 3-(4-(5-hydroxypyrimidin-2-yl)piperazin-1-yl)-1-(4-methylbenzyl)pyrrolidin-2-one

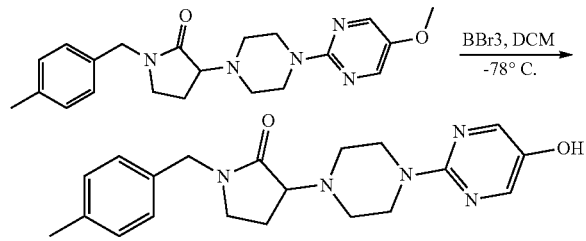

To a stirred solution of 3-(4-(5-methoxypyrimidin-2-yl)piperazin-1-yl)-1-(4-methylbenzyl)pyrrolidin-2-one (60 mg, 0.157 mmol) in DCM (8 mL) at −78° C. was slowly added BBr3 in DCM (5 mL, 5.00 mmol). The reaction mixture was stirred at RT for 12 h. The completion of the reaction was monitored by LCMS. The reaction mixture was cooled to 0° C. and quenched with sat NaHCO3 solution extracted with DCM (2×25 mL), the organic layer was dried over sodium-sulphate and evaporation under reduced pressure to get crude compound 75 mg. The crude compound was submitted to SCP. The crude material was purified via preparative LC/MS with the following conditions: Waters Xbridge C18, 19×150 mm, 5 μm; Guard Column: Waters XBridge C18, 19×10 mm, 5 μm; Mobile Phase A:5:95 Acetonitrile:water with 10 mM NH4OAc; Mobile Phase B: 95:5 Acetonitrile:water with 10 mM NH4OAc; Gradient:5-35% B over 25 minutes, followed by a 10 minute hold at 35% B and 5 minute hold at 100% B; Flow:15 ml/min. Fractions containing the desired product were combined and dried using a Genevac centrifugal evaporator to get 3-(4-(5-hydroxypyrimidin-2-yl)piperazin-1-yl)-1-(4-methylbenzyl)pyrrolidin-2-one (15.1 mg, 0.041 mmol, 26.1% yield) as pale yellow solid. Two analytical LC/MS injections were used to determine the final purity.

Injection 1 conditions: Column: Ascentis Express C18 (50×2.1) mm, 2.7 μm; Mobile Phase A: 5:95 Acetonitrile:water with 10 mM NH4OAc; Mobile Phase B: 95:5 Acetonitrile:water with 10 mM NH4OAc; Temperature: 50° C.; Gradient:0-100% B over 3 minutes; Flow: 1.1 ml/min.

Injection 2 conditions: Column: Ascentis Express C18 (50×2.1) mm, 2.7 μm; Mobile Phase A: 5:95 Acetonitrile:water with 0.1% TFA; Mobile Phase B: 95:5 Acetonitrile:water with 0.1% TFA; Temperature: 50° C.; Gradient:0-100% B over 3 minutes; Flow:1.1 ml/min.

$^1$H NMR: (400 MHz, METHANOL-$d_4$) □=8.03 (s, 2H), 7.17 (d, J=2.0 Hz, 4H), 4.53-4.46 (m, 1H), 4.41-4.33 (m, 1H), 3.74-3.59 (m, 5H), 3.30-3.19 (m, 3H), 2.97-2.88 (m, 4H), 2.68-2.59 (m, 2H), 2.34 (s, 3H), 2.24-2.14 (m, 1H), 2.10-1.98 (m, 1H).

LCMS Method info: A: 95% Water: 5% Acetonitrile; 10 mM NH4OAC, B: 5% Water: 95% Acetonitrile; 10 mM NH4OAC, Flow: 1.1 ml/min, Temp: 50° C., Column: Ascentis Express C18 (50×2.1) mm, 2.7 μm, Time (min): 0-3, % B: 0-100, LCMS RT=1.24 min, M (+1)–368.

Chiral screening: Injection Volume: 10, Co-Solvent:0.3% DEA in Methanol, Column: Lux Cellulose 4 (250×4.6) mm, 5 u, Column Temperature; 27.1, Total Flow:4, CO2 Flow Rate:2.4, Co-Solvent Flow Rate:1.6, Co-Solvent %:40, Back Pressure:99, Chiral RT:5.59 min.

Example 4: 1-(3-fluoro-4-(trifluoromethoxy)phenyl)-3-(4-(5-hydroxypyridin-2-yl)piperazin-1-yl)pyrrolidin-2-one

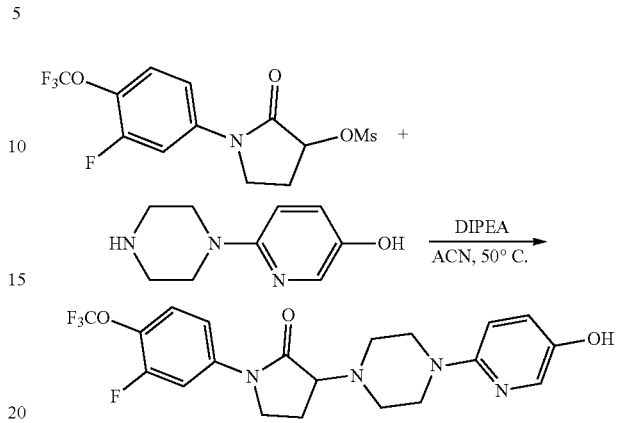

To a solution of 6-(piperazin-1-yl)pyridin-3-ol hydrochloride (20 mg, 0.093 mmol) in Acetonitrile (2 mL) and DIPEA (0.049 mL, 0.278 mmol) heated to 80° C. was added 1-(3-fluoro-4-(trifluoromethoxy)phenyl)-2-oxopyrrolidin-3-yl methanesulfonate (43.1 mg, 0.121 mmol) in Acetonitrile (1 mL) over 1 min. The mixture was then stirred at 80° C. for 16 h. The mixture was allowed to cool to RT and then concentrated. The residue was purified by SCP. The crude material was purified via preparative LC/MS with the following conditions: Waters Xbridge C18, 19×150 mm, 5 μm; Guard Column:Waters XBridge C18, 19×10 mm, 5 μm; Mobile Phase A:5:95 Acetonitrile:water with 10 mM NH4OAc; Mobile Phase B: 95:5 Acetonitrile:water with 10 mM NH4OAc; Gradient:10-45% B over 25 minutes, followed by a 10 minute hold at 45% B and 5 minute hold at 100% B; Flow:15 ml/min. Fractions containing the desired product were combined and dried using a Genevac centrifugal evaporator to get 1-(3-fluoro-4-(trifluoromethoxy)phenyl)-3-(4-(5-hydroxypyridin-2-yl)piperazin-1-yl)pyrrolidin-2-one (1.5 mg, 3.34 μmol, 3.60% yield) as pale yellow solid. Two analytical LC/MS injections were used to determine the final purity.

Injection 1 conditions: Column: Ascentis Express C18 (50×2.1) mm, 2.7 μm; Mobile Phase A: 5:95 Acetonitrile:water with 10 mM NH4OAc; Mobile Phase B: 95:5 Acetonitrile:water with 10 mM NH4OAc; Temperature: 50° C.; Gradient:0-100% B over 3 minutes; Flow: 1.1 ml/min.

Injection 2 conditions: Column: Ascentis Express C18 (50×2.1) mm, 2.7 μm; Mobile Phase A: 5:95 Acetonitrile:water with 0.1% TFA; Mobile Phase B: 95:5 Acetonitrile:water with 0.1% TFA; Temperature: 50° C.; Gradient:0-100% B over 3 minutes; Flow:1.1 ml/min.

$^1$H NMR: (400 MHz, DMSO-$d_6$) □ ppm 8.87-9.06 (m, 1H) 7.90-7.99 (m, 1H) 7.71-7.78 (m, 1H) 7.53-7.64 (m, 2H) 6.98-7.13 (m, 2H) 6.67-6.76 (m, 1H) 3.64-3.87 (m, 3H) 2.89-2.99 (m, 2H) 2.57-2.71 (m, 2H) 2.18-2.37 (m, 1H) 2.00-2.13 (m, 1H).

LCMS: Method info: A: 95% Water: 5% Acetonitrile; 10 mM NH4OAC, B: 5% Water: 95% Acetonitrile; 10 mM NH4OAC, Flow: 1.1 ml/min, Temp: 50° C., Column: Ascentis Express C18 (50×2.1) mm, 2.7 μm, Time (min): 0-3, % B: 0-100, RT–1.49 min, M(+1)–441.

Example 5

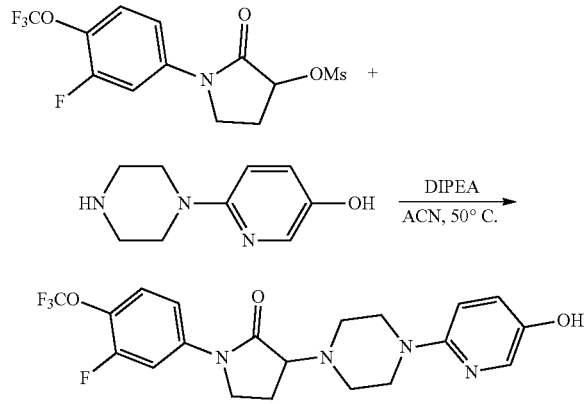

To a solution of 6-(piperazin-1-yl)pyridin-3-ol hydrochloride (20 mg, 0.093 mmol) in Acetonitrile (2 mL) and DIPEA (0.049 mL, 0.278 mmol) heated to 80° C. was added 1-(3-fluoro-4-(trifluoromethoxy)phenyl)-2-oxopyrrolidin-3-yl methanesulfonate (25 mg, 0.070 mmol) in ACN (1 mL) over 1 minute. The reaction mixture was stirred at 80° C. for 12 h. The completion of the reaction was monitored by LCMS. The reaction mixture was cooled to RT and evaporated under reduced pressure to get crude compound which was submitted to SCP. The crude material was purified via preparative LC/MS with the following conditions: Waters Xbridge C18, 19×150 mm, 5 μm; Guard Column:Waters XBridge C18, 19×10 mm, 5 μm; Mobile Phase A:5:95 Acetonitrile:water with 10 mM NH$_4$OAc; Mobile Phase B: 95:5 Acetonitrile:water with 10 mM NH$_4$OAc; Gradient:10-45% B over 25 minutes, followed by a 10 minute hold at 45% B and 5 minute hold at 100% B; Flow:15 ml/min. Fractions containing the desired product were combined and dried using a Genevac centrifugal evaporator to get 1-(3-fluoro-4-(trifluoromethoxy)phenyl)-3-(4-(5-hydroxypyridin-2-yl)piperazin-1-yl)pyrrolidin-2-one (4.7 mg, 10.25 μmol, 11.05% yield) as pale yellow solid. Two analytical LC/MS injections were used to determine the final purity.

Injection 1 conditions: Column: Ascentis Express C18 (50×2.1) mm, 2.7 μm; Mobile Phase A: 5:95 Acetonitrile:water with 10 mM NH4OAc; Mobile Phase B: 95:5 Acetonitrile:water with 10 mM NH4OAc; Temperature: 50° C.; Gradient:0-100% B over 3 minutes; Flow: 1.1 ml/min.

Injection 2 conditions: Column: Ascentis Express C18 (50×2.1) mm, 2.7 μm; Mobile Phase A: 5:95 Acetonitrile:water with 0.1% TFA; Mobile Phase B: 95:5 Acetonitrile:water with 0.1% TFA; Temperature: 50° C.; Gradient:0-100% B over 3 minutes; Flow:1.1 ml/min.

LCMS: Method info: A: 95% Water: 5% Acetonitrile; 10 mM NH4OAC, B: 5% Water:95% Acetonitrile; 10 mM NH4OAC, Flow: 1.1 ml/min, Temp: 50° C., Column: Ascentis Express C18 (50×2.1) mm, 2.7 μm, Time (min): 0-3, % B: 0-100, RT–1.484 min, M(+1)–441.

1H NMR: 400 MHz, DMSO-d6: δ 8.98 (br s, 1H), 7.93-7.69 (m, 2H), 7.73-7.74 (m, 1H), 7.59 (s, 2H), 6.95-7.20 (m, 1H), 6.71-6.95 (m, 1H), 3.71-3.81 (m, 3H), 3.32-3.37 (m, 4H), 2.89-2.94 (m, 2H), 2.60-2.73 (m, 2H), 2.24-2.45 (m, 2H).

Example 6 (P1 & P2)

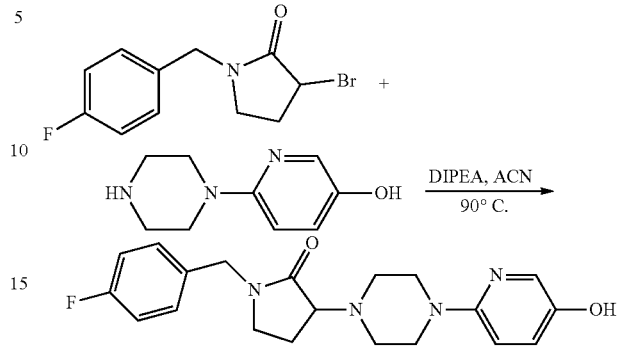

To a stirred solution of 3-bromo-1-(4-fluorobenzyl)pyrrolidin-2-one (0.042 g, 0.153 mmol), 6-(piperazin-1-yl)pyridin-3-ol, HCl (0.03 g, 0.139 mmol) and DIPEA (0.024 mL, 0.139 mmol) in Acetonitrile (5 mL) was heated at 90° C. for 18 h. The completion of the reaction was monitored by LCMS. The reaction mixture was cooled to RT. The reaction mixture was diluted with water (15 mL) and the aqueous layer was separated and extracted with EtOAc (3×25 mL). The combined organic layers were washed with water (15 mL) and brine (15 mL) and dried over Na2SO4. The mixture was filtered, and the solvent was removed in vacuum to give the crude product. The crude was submitted to SCP. The crude material was purified via preparative LC/MS with the following conditions: Waters Xbridge C18, 19×150 mm, 5 μm; Guard Column:Waters XBridge C18, 19×10 mm, 5 μm; Mobile Phase A:5:95 Acetonitrile:water with 10 mM NH$_4$OAc; Mobile Phase B: 95:5 Acetonitrile:water with 10 mM NH$_4$OAc; Gradient:10-30% B over 25 minutes, followed by a 10 minute hold at 30% B and 5 minute hold at 100% B; Flow:15 ml/min. Fractions containing the desired product were combined and dried using a Genevac centrifugal evaporator to get (+/−)1-(4-fluorobenzyl)-3-(4-(5-hydroxypyridin-2-yl)piperazin-1-yl)pyrrolidin-2-one (45.1 mg, 0.122 mmol, 88% yield) as pale yellow solid. Two analytical LC/MS injections were used to determine the final purity.

Injection 1 conditions: Column: Ascentis Express C18 (50×2.1) mm, 2.7 μm; Mobile Phase A: 5:95 Acetonitrile:water with 10 mM NH4OAc; Mobile Phase B: 95:5 Acetonitrile:water with 10 mM NH4OAc; Temperature: 50° C.; Gradient:0-100% B over 3 minutes; Flow: 1.1 ml/min.

Injection 2 conditions: Column: Ascentis Express C18 (50×2.1) mm, 2.7 μm; Mobile Phase A: 5:95 Acetonitrile:water with 0.1% TFA; Mobile Phase B: 95:5 Acetonitrile:water with 0.1% TFA; Temperature: 50° C.; Gradient:0-100% B over 3 minutes; Flow:1.1 ml/min.

The Racemic compound was separated by Chiral SFC. SFC Purification Method:

Analytical SFC Conditions: Column/dimensions: Chiralcel OD-H (250×4.6) mm, 5 u, % CO2: 60%, % Co solvent: 40% (0.25% DEA in Methanol), Total Flow: 3.0 g/min, Back Pressure: 100 bar, Temperature: 25° C., UV: 243.

Preparative SFC Conditions: Column/dimensions: Chiralcel OD-H (250×21) mm, 5 u, % CO2: 60%, % Co solvent: 40% (0.25% DEA in Methanol), Total Flow: 70.0 g/min, Back Pressure: 100 bar, Temperature: 25° C., UV: 243, Peak number: Retention Time::Peak 1: 3.00::Peak 2: 4.00, Solubility: Methanol+THF (1:1) in 5 ml, Loadability/Inj: 8.00 mg/mL, Total No of injections: 15, Total Time for purification 1.0 hr, Instrument details: Make/Model: Thar SFC-80 Chiral Purification resulted in 1-(4-fluorobenzyl)-3-(4-(5-hydroxypyridin-2-yl)piperazin-1-yl)pyrrolidin-2-one (17 mg, 0.046 mmol, 33.0% yield) and 1-(4-fluorobenzyl)-3-(4-(5-hydroxypyridin-2-yl)piperazin-1-yl)pyrrolidin-2-one (14 mg, 0.038 mmol, 27.2% yield).

For P1 (Homochiral): 1-(4-fluorobenzyl)-3-(4-(5-hydroxypyridin-2-yl)piperazin-1-yl)pyrrolidin-2-one

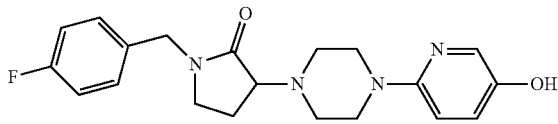 [SMILES: O=C1C(N2CCN(c3ccc(O)cn3)CC2)CCN1Cc1ccc(F)cc1]

LCMS: Column-Ascentis Express C18 (50×2.1 mm-2.7 μm), Mphase A: 10 mM NH4C00H IN WATER:ACN(98: 02), Mphase B: 10 mM NH4C00H IN WATER:ACN(02: 98), Flow=1 ML/MIN, Time: % B::0.0:0.0::1.7:100.0::3.0: 100.0::3.2:0.0, RT-2.182 min, M(+1)-371.

Chiral purity: Injection Volume: 10, Co-Solvent: 0.3% DEA in Methanol, Column: Chiralcel OD-H (4.6×250) mm, 5 u, Column Temperature: 23.4, Total Flow: 3, CO2 Flow Rate: 1.8, Co-Solvent Flow Rate: 1.2, Co-Solvent %:40, Back Pressure: 100, RT-2.57 min.

1H NMR: 400 MHz, MeOD: δ 2.05 (t, J=15.20 Hz, 1H), 2.15-2.20 (m, 1H), 2.67-2.71 (m, 2H), 2.97-3.00 (m, 2H), 3.23-3.28 (m, 2H), 3.42-3.43 (m, 2H), 3.60 (t, J=17.60 Hz, 1H), 4.40 (d, J=14.40 Hz, 1H), 4.51 (d, J=14.80 Hz, 1H), 6.76 (d, J=8.80 Hz, 1H), 7.06-7.10 (m, 2H), 7.12-7.15 (m, 1H), 7.28-7.32 (m, 2H), 7.73-7.74 (m, 1H).

For P2 (Homochiral): 1-(4-fluorobenzyl)-3-(4-(5-hydroxypyridin-2-yl)piperazin-1-yl)pyrrolidin-2-one

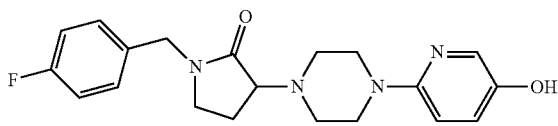 [SMILES: O=C1C(N2CCN(c3ccc(O)cn3)CC2)CCN1Cc1ccc(F)cc1]

LCMS: Column-Ascentis Express C18 (50×2.1 mm-2.7 μm), Mphase A: 10 mM NH4C00H IN WATER:ACN(98: 02), Mphase B: 10 mM NH4C00H IN WATER:ACN(02: 98), Flow=1 ML/MIN, Time: % B::0.0:0.0::1.7:100.0::3.0: 100.0::3.2:0.0, RT-2.188 min, M(+1)-371.

Chiral purity: Injection Volume: 10, Co-Solvent: 0.3% DEA in Methanol, Column: Chiralcel OD-H (4.6×250) mm, 5 u, Column Temperature: 23.4, Total Flow: 3, CO2 Flow Rate: 1.8, Co-Solvent Flow Rate: 1.2, Co-Solvent %:40, Back Pressure: 100, RT-4.11 min.

1H NMR: 400 MHz, MeOD: δ 2.02-2.11 (m, 1H), 2.16-2.20 (m, 1H), 2.65-2.71 (m, 2H), 2.96-3.02 (m, 2H), 3.21-3.28 (m, 2H), 3.30-3.38 (m, 4H), 3.60 (t, J=17.60 Hz, 1H), 4.43 (d, J=-8.40 Hz, 1H), 4.51 (d, J=14.80 Hz, 1H), 6.76 (d, J=8.80 Hz, 1H), 7.06-7.10 (m, 2H), 7.12-7.15 (m, 1H), 7.28-7.32 (m, 2H), 7.74 (d, J=2.80 Hz, 1H).

Example 7 (P1 & P2)

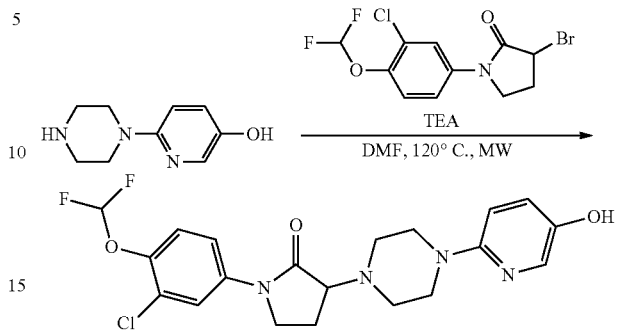

To a solution of 6-(piperazin-1-yl)pyridin-3-ol (250 mg, 1.395 mmol) in Acetonitrile (10 mL) was added Triethyl amine (706 mg, 6.97 mmol) and 3-bromo-1-(3-chloro-4-(difluoromethoxy)phenyl)pyrrolidin-2-one (475 mg, 1.395 mmol) at RT. The reaction mixture was stirred at 90° C. for 1.5 h in CEM Microwave. The completion of the reaction was monitored by LCMS. The reaction mixture was diluted with sat. ammonium chloride solution (50 mL) and the product was extracted with ethyl acetate (50 mL). The organic layer was dried over $Na_2SO_4$ and evaporated under reduced pressure to get crude residue 0.9 g Crude Purity: 51%. The crude was purified through Reverse phase HPLC to get (+/−)1-(3-chloro-4-(difluoromethoxy)phenyl)-3-(4-(5-hydroxypyridin-2-yl)piperazin-1-yl)pyrrolidin-2-one (100 mg, 0.227 mmol, 16.33% yield).

HPLC Method Information: Column: SUNFIRE C18 250×30 10 u, Mobile Phase A: 10 mM NH4OAC IN WATER, Mobile Phase B: CAN Solubility: CAN+THF, Flow: 30 ml/min Loadability: 50 mg, T/% B: 0/30, 10/60 No. Of Injections: 16, Total Purification Time: 8 min.

LCMS (TFA): RT0.67 min; {Mobile phase A:0.1% TFA in water, Mobile phase B: Acetonitrile} Acquity BEH C18 (2.1×50 mm) 1.7 u, gradient=2.25 min, wavelength=220 nm; MS (ES): m/z 439 M+H.

The Racemic mixture was subjected to SFC purification to give Isomer-P1, isomer P2.

Preparative SFC Conditions: Column/dimensions: Lux-cellulose-2(250×21.5) mm, 5 u, % CO2: 60%, % Co solvent: 40% (0.25% DEA in Methanol), Total Flow: 70.0 g/min, Back Pressure: 100 bar, Temperature: 25° C., UV: 247, Peak number: Retention Time::Peak 1: 4.30::Peak 2: 5.90, Solubility: Methanol in 30.0 ml.

For P1 (Homochiral): 1-(3-chloro-4-(difluoromethoxy)phenyl)-3-(4-(5-hydroxypyridin-2-yl)piperazin-1-yl)pyrrolidin-2-one

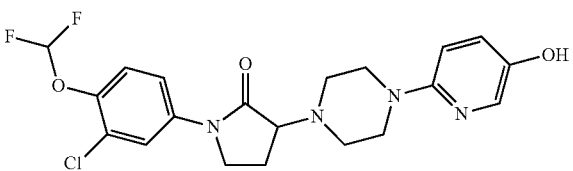 [SMILES: O=C1C(N2CCN(c3ccc(O)cn3)CC2)CCN1c1ccc(OC(F)F)c(Cl)c1]

HPLC: 95/5 to 5/95 $H_2O/CH_3CN$/0.05% TFA, flow=1 mL/min, gradient=15 min, Sunfire $C_{18}$ 4.6×150 mm:

RT=5.59 min; Purity @220 nm: 94.033%; @254 nm: 94.16%. Xbridge Phenyl 3.5 um, 4.6×150 mm: RT=6.55 min; Purity @220 nm: 89.82%; @254 nm:92.52%.

LCMS: Column-Ascentis Express C18 (50×2.1 mm-2.7 μm), Mphase A: 10 mM NH4C00H IN WATER:ACN(98:02), Mphase B: 10 mM NH4C00H IN WATER:ACN(02:98), Flow=1 ML/MIN, Time: % B::0.0:0.0::1.7:100.0::3.0:100.0::3.2:0.0, RT−2.072 min, M(+1)−439.

SFC: CO2 3.0_Colvent_100.met; Flow:—total flow 3, CO2 flow rate 2.1, Co-solvent (0.3% DEA in Methanol) 0.9; Column:—Chiralpak AD H (250×4.6) mm 5μ; RT 3.17 min, Purity@ 217 nm:100%.

1H NMR: 400 MHz, MeOD: δ 2.18-2.24 (m, 1H), 2.31-2.35 (m, 1H), 2.73-2.78 (m, 2H), 3.02-3.07 (m, 2H), 3.31-3.41 (m, 4H), 3.72-3.85 (m, 3H), 6.65-7.02 (m, 2H), 7.13-7.16 (m, 1H), 7.32 (d, J=9.20 Hz, 1H), 7.57-7.60 (m, 1H), 7.74 (d, J=3.20 Hz, 1H), 7.89 (d, J=75.60 Hz, 1H).

For P2 (Homochiral): (1-(3-chloro-4-(difluoromethoxy)phenyl)-3-(4-(5-hydroxypyridin-2-yl)piperazin-1-yl)pyrrolidin-2-one

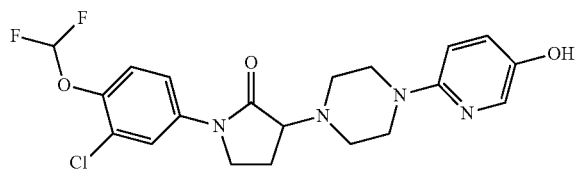 [SMILES: O=C1C(N2CCN(c3ccc(O)cn3)CC2)CCN1c1ccc(OC(F)F)c(Cl)c1]

HPLC: 95/5 to 5/95 H2O/CH3CN/0.05% TFA, flow=1 mL/min, gradient=15 min, Sunfire C18 4.6×150 mm: RT=5.6 min; Purity @220 nm: 93.02%; @254 nm: 93.29%. Xbridge Phenyl 3.5 um, 4.6×150 mm: RT=6.536 min; Purity @220 nm: 91.18%; @254 nm:93.24%.

LCMS: Column-Ascentis Express C18 (50×2.1 mm-2.7 μm), Mphase A: 10 mM NH4C00H IN WATER:ACN(98:02), Mphase B: 10 mM NH4C00H IN WATER:ACN(02:98), Flow=1 ML/MIN, Time: % B::0.0:0.0::1.7:100.0::3.0:100.0::3.2:0.0, RT 2.068 min, M(+1)−439.

SFC: CO2 3.0_Colvent_100.met; Flow:—total flow 3, CO2 flow rate 2.1, Co-solvent (0.3% DEA in Methanol) 0.9; Column:—Chiralpak AD H (250×4.6) mm 5μ; RT 4 min; Purity@ 217 nm:98.86%.

1H NMR: 400 MHz, MeOD: δ 2.16-2.26 (m, 1H), 2.32-2.38 (m, 1H), 2.73-2.78 (m, 2H), 3.03-3.07 (m, 2H), 3.38-3.41 (m, 4H), 3.72-3.84 (m, 3H), 6.65-7.02 (m, 2H), 7.13-7.16 (m, 1H), 7.32 (d, J=9.20 Hz, 1H), 7.57-7.60 (m, 1H), 7.74 (d, J=3.20 Hz, 1H), 7.89 (d, J=75.60 Hz, 1H).

Example 8 (P1 & P2)

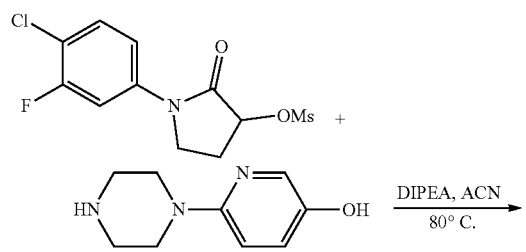

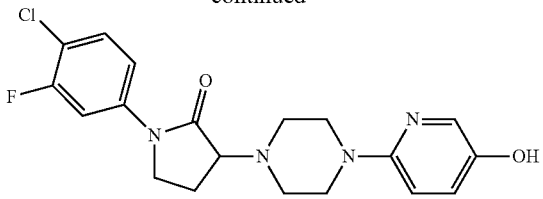

Procedure: DIPEA (0.039 mL, 0.223 mmol) was added to a stirred solution of 6-(piperazin-1-yl)pyridin-3-ol (0.04 g, 0.223 mmol) in Acetonitrile (5 mL) at RT and heated to 50° C. after 5 min 1-(4-chloro-3-fluorophenyl)-2-oxopyrrolidin-3-yl methanesulfonate (0.124 g, 0.402 mmol) was dissolved in Acetonitrile (5 mL). The reaction mixture was heated at 85° C. for 18 h. The completion of the reaction was monitored by LCMS. The reaction mixture was evaporated to dryness, and was submitted to SCP for purification. The chiral screening of 8 shows two major peaks, indicates the racemization. The racemic mixture 8; 1-(4-chloro-3-fluorophenyl)-3-(4-(5-hydroxypyridin-2-yl)piperazin-1-yl)pyrrolidin-2-one (20 mg, 0.051 mmol, 22.8% yield) was separated by SFC obtained P1; 1-(4-chloro-3-fluorophenyl)-3-(4-(5-hydroxypyridin-2-yl)piperazin-1-yl)pyrrolidin-2-one and P2; 1-(4-chloro-3-fluorophenyl)-3-(4-(5-hydroxypyridin-2-yl)piperazin-1-yl)pyrrolidin-2-one.

Chiral screening For 8: Injection Volume: 10, Co-Solvent: 0.3% DEA in Methanol, Column: Chiralcel OD-H (4.6×250) mm, 5 u, Column Temperature: 26, Total Flow: 4, CO2 Flow Rate: 2.4, Co-Solvent Flow Rate: 1.6, Co-Solvent %: 40, Back Pressure: 129.

| Peak Info | | | | |
|---|---|---|---|---|
| Number | Peak Name | RT (min) | Area | Area % |
| 1 | Peak 1 | 1.52 | 224.6273 | 3.2263 |
| 2 | Peak 2 | 2.16 | 28.7287 | 0.4126 |
| 3 | Peak 3 | 3.02 | 3801.0048 | 54.5936 |
| 4 | Peak 4 | 6.49 | 2908.0087 | 41.7675 |

SFC Purification Method

Analytical SFC Conditions: Column/dimensions: Chiralcel OD-H (250×4.6) mm, 5 u, % CO2: 60%,% Co solvent: 40% (0.25% DEA in Methanol), Total Flow: 4.0 g/min, Back Pressure: 100 bar, Temperature: 25° C., UV: 247.

Preparative SFC Conditions: Column/dimensions: Chiralcel OD-H (250×21) mm, 5 u, % CO2: 60%, % Co solvent: 40% (0.25% DEA in Methanol), Total Flow: 70.0 g/min, Back Pressure: 100 bar, Temperature: 25° C., UV: 247.

For P1 (Homochiral):

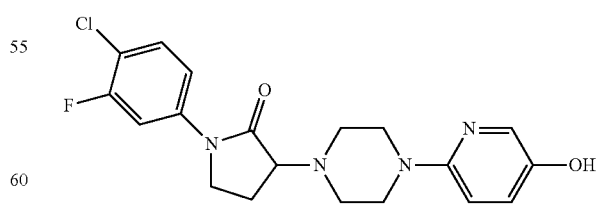

1H NMR: (400 MHz, METHANOL-d4) δ=7.85 (dd, J=2.5, 12.0 Hz, 1H), 7.76 (d, J=2.5 Hz, 1H), 7.53-7.40 (m, 2H), 7.20-7.10 (m, 1H), 6.79 (d, J=9.0 Hz, 1H), 3.94-3.71 (m, 3H), 3.53-3.39 (m, 4H), 3.20-3.00 (m, 3H), 2.78 (s, 2H), 2.27-2.16 (m, 2H).

LCMS: Column-Ascentis Express C18 (50×2.1 mm-2.7 μm), Mphase A: 10 mM NH4C00H IN WATER:ACN(98:02), Mphase B: 10 mM NH4C00H IN WATER:ACN(02:98), Flow=1 ML/MIN, Time: % B::0.0:0.0::1.7:100.0::3.0:100.0::3.2 0.0, RT-2.18 min, M (+1)-391.

Chiral purity: Injection Volume: 5, Co-Solvent: 0.3% DEA in Methanol, Column: chiralpak-ODH (4.6*250) mm5 u, Column Temperature: 22.6, CO2 Flow Rate: 2.4, Co-Solvent Flow Rate: 1.6, Co-Solvent:40, Total Flow: 4, Back Pressure: 97, RT-3.15 min.

For P2 (Homochiral):

LCMS: Column-Ascentis Express C18 (50×2.1 mm-2.7 μm), Mphase A: 10 mM NH4C00H IN WATER:ACN(98:02), Mphase B: 10 mM NH4C00H IN WATER:ACN(02:98), Flow=1 ML/MIN, Time: % B::0.0:0.0::1.7:100.0::3.0:100.0::3.2:0.0, RT-2.21 min, M(+1)-391.

$^1$H NMR: (400 MHz, METHANOL-d$_4$) □=7.85 (dd, J=2.5, 12.0 Hz, 1H), 7.76 (d, J=2.5 Hz, 1H), 7.53-7.40 (m, 2H), 7.20-7.10 (m, 1H), 6.79 (d, J=9.0 Hz, 1H), 3.94-3.71 (m, 3H), 3.53-3.39 (m, 4H), 3.20-3.00 (m, 3H), 2.78 (s, 2H), 2.27-2.16 (m, 2H).

Chiral purity: Injection Volume: 5, Co-Solvent: 0.3% DEA in Methanol, Column: chiralpak-ODH (4.6*250) mm5 u, Column Temperature: 22.1, CO2 Flow Rate: 2.4, Co-Solvent Flow Rate: 1.6, Co-Solvent:40, Total Flow: 4, Back Pressure: 101, RT-6.6 min.

Example 9 (P1 & P2)

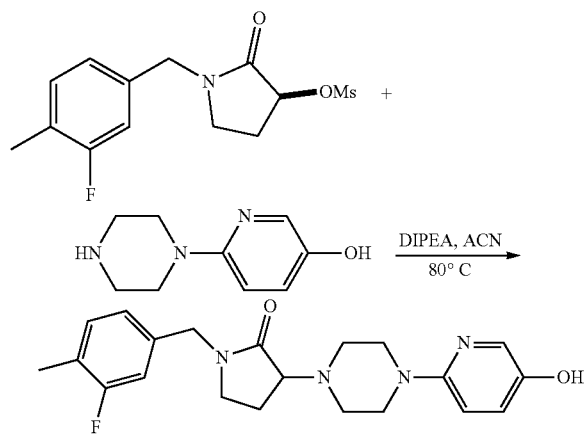

To a solution of 6-(piperazin-1-yl)pyridin-3-ol (40 mg, 0.185 mmol) in Acetonitrile (2 mL) and DIPEA (0.097 mL, 0.556 mmol) heated to 80° C. was added (S)-1-(3-fluoro-4-methylbenzyl)-2-oxopyrrolidin-3-yl methanesulfonate (84 mg, 0.278 mmol)) in Acetonitrile (1 mL) over 1 min. The mixture was then stirred at 80° C. for 16 h. The reaction mixture was allowed to cool to RT and then concentrated. The residue was purified by SCP. The crude material was purified via preparative LC/MS with the following conditions: Waters Xbridge C18, 19×150 mm, 5 μm; Guard Column: Waters XBridge C18, 19×10 mm, 5 μm; Mobile Phase A:5:95 Acetonitrile:water with 10 mM NH4OAc; Mobile Phase B: 95:5 Acetonitrile:water with 10 mM NH4OAc; Gradient:5-35% B over 25 minutes, followed by a 10 minute hold at 35% B and 5 minute hold at 100% B; Flow:15 ml/min. Fractions containing the desired product were combined and dried using a Genevac centrifugal evaporator to get (+/-)1-(3-fluoro-4-methylbenzyl)-3-(4-(5-hydroxypyridin-2-yl)piperazin-1-yl)pyrrolidin-2-one (20 mg, 0.052 mmol, 27.8% yield) as pale yellow solid. Two analytical LC/MS injections were used to determine the final purity.

Injection 1 conditions: Column: Ascentis Express C18 (50×2.1) mm, 2.7 μm; Mobile Phase A: 5:95 Acetonitrile:water with 10 mM NH4OAc; Mobile Phase B: 95:5 Acetonitrile:water with 10 mM NH4OAc; Temperature: 50° C.; Gradient:0-100% B over 3 minutes; Flow: 1.1 ml/min.

Injection 2 conditions: Column: Ascentis Express C18 (50×2.1) mm, 2.7 μm; Mobile Phase A: 5:95 Acetonitrile:water with 0.1% TFA; Mobile Phase B: 95:5 Acetonitrile:water with 0.1% TFA; Temperature: 50° C.; Gradient:0-100% B over 3 minutes; Flow:1.1 ml/min.

SFC Purification Method:

Analytical SFC Conditions: Column/dimensions: Chiralcel OD-H (250×4.6) mm, 5 u, % CO2: 60%, % Co solvent: 40% (0.25% DEA in Methanol), Total Flow: 3.0 g/min, Back Pressure: 100 bar, Temperature: 25° C., UV: 245.

Preparative SFC Conditions: Column/dimensions: Chiralcel OD-H (250×21) mm, 5 u, % CO2: 60%, % Co solvent: 40% (0.25% DEA in Methanol), Total Flow: 60.0 g/min, Back Pressure: 100 bar, Temperature: 25° C., UV: 245, Peak number: Retention Time, Peak 1: 3.00::Peak 2: 4.00, Solubility: Methanol in 10.0 ml, Loadability/Inj: 5.00 mg/mL, Total No of injections:10, Total Time for purification 1.0 hr, Instrument details: Make/Model: Thar SFC-80.

For P1 (Homochiral):

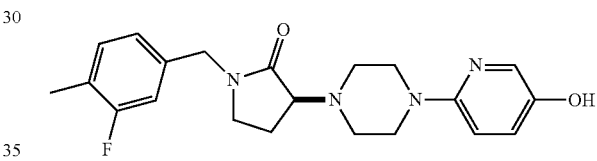

LCMS: Column-Kinetex XB-C18 (75×3 mm-2.6 μm), Mphase A: 10 mM NH4C00H IN WATER:ACN(98:02), Mphase B: 10 mM NH4C00H IN WATER:ACN(02:98), Time: % B: Flow::0:20:1::4:100:1::4.6:100:1.5::4.7 20 1.5, RT-1.653 min, M(+1)-385.

$^1$H NMR: (400 MHz, DMSO-d$_6$) □=9.06-8.88 (m, 1H), 7.79-7.68 (m, 1H), 7.33-7.19 (m, 1H), 7.10-7.03 (m, 1H), 7.00-6.90 (m, 2H), 6.76-6.65 (m, 1H), 4.43-4.24 (m, 2H), 3.52-3.40 (m, 1H), 3.29-3.23 (m, 4H), 3.20-3.01 (m, 2H), 2.95-2.84 (m, 2H), 2.22 (d, J=1.5 Hz, 3H), 2.15-2.02 (m, 1H), 1.99-1.81 (m, 1H).

Chiral Purity: Injection Volume: 10, Co-Solvent:0.3% DEA in Methanol, Column: Chiralcel OD-H (250×4.6) mm, 5 u, Column Temperature; 27.1, Total Flow:4, CO2 Flow Rate:2.4, Co-Solvent Flow Rate:1.6, Co-Solvent %:40, Back Pressure:99, RT-4.94 min.

For P2 (Homochiral):

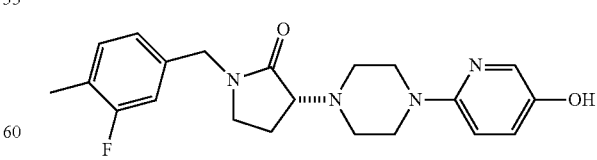

LCMS: Column-Kinetex XB-C18 (75×3 mm-2.6 μm), Mphase A: 10 mM NH4C00H IN WATER:ACN(98:02), Mphase B: 10 mM NH4C00H IN WATER:ACN(02:98), Time: % B: Flow::0:20:1::4:100:1::4.6:100:1.5::4.7 20 1.5, RT-1.656 min, M(+1)-385.

$^1$H NMR: (400 MHz, DMSO-d6) δ=9.02-8.90 (m, 1H), 7.80-7.67 (m, 1H), 7.34-7.23 (m, 1H), 7.11-7.03 (m, 1H), 7.00-6.90 (m, 1H), 6.76-6.63 (m, 1H), 4.44-4.24 (m, 2H), 3.55-3.44 (m, 1H), 3.30-3.22 (m, 4H), 3.20-3.10 (m, 2H), 2.96-2.87 (m, 2H), 2.60-2.53 (m, 2H), 2.22 (d, J=1.0 Hz, 3H), 2.16-2.03 (m, 1H), 2.00-1.83 (m, 1H).

Chiral Purity: Injection Volume; 10, Co-Solvent: 0.3% DEA in Methanol, Column: Chiralcel OD-H (4.6×250) mm, 5 u, Column Temperature: 23.5, Total Flow: 3, CO2 Flow Rate: 1.8, Co-Solvent Flow Rate:1.2, Co-Solvent %: 40, Back Pressure; 100, RT–5.42 min.

Example 10 (Homochiral)

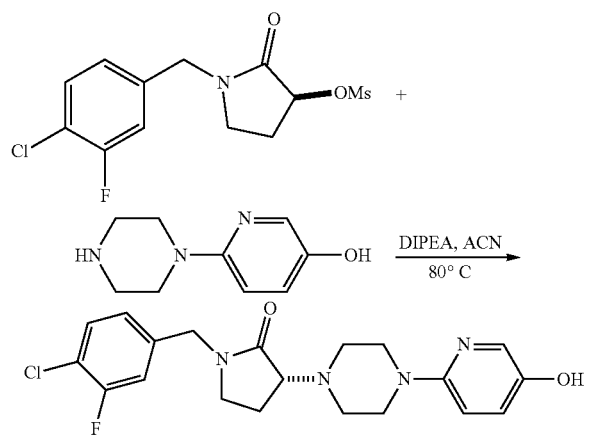

To a solution of 6-(piperazin-1-yl)pyridin-3-ol (0.111 g, 0.622 mmol) in 1.0 mL of CH$_3$CN and DIPEA (0.271 mL, 1.554 mmol) at 80° C. was added a solution of (S)-1-(4-chloro-3-fluorobenzyl)-2-oxopyrrolidin-3-yl methanesulfonate (0.2 g, 0.622 mmol) in 0.5 mL of CH$_3$CN over 1.5 h. The mixture was then stirred at 80° C. for 16 h. The completion of the reaction was monitored by LCMS. The reaction mixture was cool to RT and was concentrated to get crude 0.3 g. The crude residue was purified by SCP. The crude material was purified via preparative LC/MS with the following conditions: Waters Xbridge C18, 19×150 mm, 5 μm; Guard Column:Waters XBridge C18, 19×10 mm, 5 μm; Mobile Phase A:5:95 Acetonitrile:water with 10 mM NH4OAc; Mobile Phase B: 95:5 Acetonitrile:water with 10 mM NH4OAc; Gradient:5-35% B over 25 minutes, followed by a 10 minute hold at 35% B and 5 minute hold at 100% B; Flow:15 ml/min. Fractions containing the desired product were combined and dried using a Genevac centrifugal evaporator to get (R)-1-(4-chloro-3-fluorobenzyl)-3-(4-(5-hydroxypyridin-2-yl)piperazin-1-yl)pyrrolidin-2-one (45 mg, 0.111 mmol, 16.63% yield). Two analytical LC/MS injections were used to determine the final purity.

Injection 1 conditions: Column:Ascentis Express C18 (50×2.1) mm, 2.7 μm; Mobile Phase A: 5:95 Acetonitrile:water with 10 mM NH4OAc; Mobile Phase B: 95:5 Acetonitrile:water with 10 mM NH4OAc; Temperature: 50° C.; Gradient:0-100% B over 3 minutes; Flow: 1.1 ml/min.

Injection 2 conditions: Column: Ascentis Express C18 (50×2.1) mm, 2.7 μm; Mobile Phase A: 5:95 Acetonitrile:water with 0.1% TFA; Mobile Phase B: 95:5 Acetonitrile:water with 0.1% TFA; Temperature: 50° C.; Gradient:0-100% B over 3 minutes; Flow:1.1 ml/min.

Chiral Screening: Injection Volume: 10, Co-Solvent: 0.3% DEA in Methanol, Column: Chiralcel OD-H (4.6×250) mm, 5 u, Column Temperature: 24.3, Total Flow: 3, CO2 Flow Rate: 1.95, Co-Solvent Flow Rate: 1.05, Co-Solvent %: 35, Back Pressure: 101, RT–6.12 min.

1H NMR: 400 MHz, DMSO-d6: δ 7.73 (s, 1H), 7.56 (t, J=–8.00 Hz, 1H), 7.26 (d, J=12.00 Hz, 1H), 7.06 (t, J=36.00 Hz, 2H), 6.69-6.71 (m, 4H), 4.38 (d, J=4.00 Hz, 2H), 3.47 (t, J=20.00 Hz, 1H), 3.31-3.28 (m, 5H), 3.27-3.19 (m, 2H), 2.90 (t, J=24.00 Hz, 2H), 2.53 (t, J=24.00 Hz, 2H), 2.29-2.01 (m, 1H), 1.95-1.89 (m, 1H).

LCMS: A: 95% Water: 5% Acetonitrile; 10 mM NH4OAC, B: 5% Water:95% Acetonitrile; 10 mM NH4OAC, Flow: 1.1 ml/min, Temp:50° C., Column: Ascentis Express C18 (50×2.1) mm, 2.7 μm, Time (min): 0-3, % B: 0-100, RT–2.27 min, M(+1)–405.

Example 11 (P1 & P2)

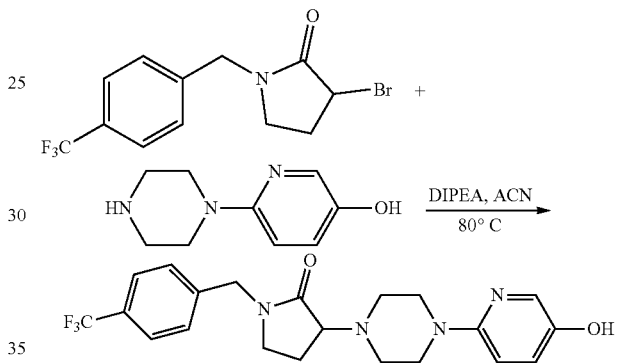

To a stirred solution of 6-(piperazin-1-yl)pyridin-3-ol hydrochloride (70 mg, 0.325 mmol) in dry DMF (1.5 mL) was added DIPEA (0.170 mL, 0.974 mmol) and 3-bromo-1-(4-(trifluoromethyl)benzyl)pyrrolidin-2-one (209 mg, 0.649 mmol). The reaction mixture was heated under MW at 120° C. for 90 min. Completion of the reaction was monitored through LCMS. The reaction mixture as such was submitted to SCP. The crude material was purified via preparative LC/MS with the following conditions: Waters Xbridge C18, 19×150 mm, 5 μm; Guard Column: Waters XBridge C18, 19×10 mm, 5 μm; Mobile Phase A:5:95 Acetonitrile:water with 10 mM NH4OAc; Mobile Phase B: 95:5 Acetonitrile:water with 10 mM NH4OAc; Gradient:5-35% B over 25 minutes, followed by a 10 minute hold at 35% B and 5 minute hold at 100% B; Flow:15 ml/min. Fractions containing the desired product were combined and dried using a Genevac centrifugal evaporator to get (60 mg, 0.142 mmol, 4.39% yield) as pale yellow solid. Two analytical LC/MS injections were used to determine the final purity.

Injection 1 conditions: Column: Ascentis Express C18 (50×2.1) mm, 2.7 μm; Mobile Phase A: 5:95 Acetonitrile:water with 10 mM NH4OAc; Mobile Phase B: 95:5 Acetonitrile:water with 10 mM NH4OAc; Temperature: 50° C.; Gradient:0-100% B over 3 minutes; Flow: 1.1 ml/min.

Injection 2 conditions: Column: Ascentis Express C18 (50×2.1) mm, 2.7 μm; Mobile Phase A: 5:95 Acetonitrile:water with 0.1% TFA; Mobile Phase B: 95:5 Acetonitrile:water with 0.1% TFA; Temperature: 50° C.; Gradient:0-100% B over 3 minutes; Flow:1.1 ml/min.

SFC Purification Method:

Analytical SFC Conditions: Column/dimensions: chiralcel OD-H (250×4.6) mm, 5 u, % CO2: 60%, % Co solvent: 40% (0.25% DEA in Methanol), Total Flow: 3.0 g/min, Back Pressure: 100 bar, Temperature: 24° C., UV: 210.

Preparative SFC Conditions: Column/dimensions: chiralcel OD-H (250×21.5) mm, 5 u, % CO2: 60%, % Co solvent: 40% (0.25% DEA in Methanol), Total Flow: 60.0 g/min, Back Pressure: 100 bar, Temperature: 25° C., UV: 210, Peak number: Retention Time::Peak 1: 2.50::Peak 2: 4.20, Solubility: Methanol in 6.0 ml, Loadability/Inj: 2.5 mg/mL, Total No of injections:12, Total Time for purification 1.0 hrs, Instrument details: Make/Model: Thar SFC-80.

For P1 (Homochiral): 3-(4-(5-hydroxypyridin-2-yl)piperazin-1-yl)-1-(4-(trifluoromethyl)benzyl)pyrrolidin-2-one

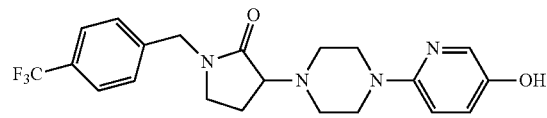 [SMILES: O=C1C(N2CCN(c3ccc(O)cn3)CC2)CCN1Cc1ccc(C(F)(F)F)cc1]

LCMS: Method info: Column-Ascentis Express C8 (50× 2.1 mm-2.7 μm), Mphase A: 2% ACN—98% H20-10 mM NH4C00H, Mphase B: 98% ACN—2% H20-10 mM NH4C00H, Flow=1 ML/MIN, Time: % B::0.0:0.0::1.7: 100.0::4.0:100.0, RT–1.798 min, M(+1)–421.

$^1$H NMR: (400 MHz, DMSO-$d_6$) δ=9.10-8.88 (m, 1H), 7.74 (s, 3H), 7.50-7.41 (m, 2H), 7.10-7.00 (m, 1H), 6.76-6.65 (m, 1H), 4.58-4.36 (m, 2H), 3.64-3.44 (m, 2H), 3.25-3.08 (m, 4H), 2.99-2.87 (m, 3H), 2.55 (br. s., 4H), 2.20-2.05 (m, 1H), 2.01-1.80 (m, 1H).

Chiral purity: Injection Volume: 10, Co-Solvent: 0.3% DEA in Methanol, Column: Chiralcel OD-H (4.6×250) mm, 5 u, Column Temperature: 25.9, Total Flow: 3, CO2 Flow Rate: 1.8, Co-Solvent Flow Rate: 1.2, Co-Solvent %: 40, Back Pressure: 44, RT–3.05 min.

For P2 (Homochiral): 3-(4-(5-hydroxypyridin-2-yl)piperazin-1-yl)-1-(4-(trifluoromethyl)benzyl)pyrrolidin-2-one

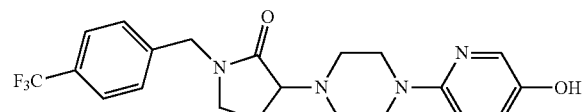

LCMS: Method info: Column-Ascentis Express C8 (50× 2.1 mm-2.7 μm), Mphase A: 2% ACN—98% H20-10 mM NH4C00H, Mphase B: 98% ACN—2% H20-10 mM NH4C00H, Flow=1 ML/MIN, Time: % B::0.0:0.0::1.7: 100.0::4.0:100.0, RT–1.793 min, M(+1)–421.

$^1$H NMR: (400 MHz, DMSO-$d_6$) δ=9.04-8.92 (m, 1H), 7.74 (br. s., 3H), 7.51-7.42 (m, 2H), 7.10-7.02 (m, 1H), 6.76-6.66 (m, 1H), 4.57-4.38 (m, 2H), 3.54-3.44 (m, 1H), 3.26-3.13 (m, 3H), 2.97-2.86 (m, 2H), 2.63-2.54 (m, 5H), 2.18-2.07 (m, 1H), 2.01-1.92 (m, 1H).

Chiral purity: Injection Volume: 10, Co-Solvent: 0.3% DEA in Methanol, Column: Chiralcel OD-H (4.6×250) mm, 5 u, Column Temperature: 25.8, Total Flow: 3, CO2 Flow Rate: 1.8, Co-Solvent Flow Rate: 1.2, Co-Solvent: 40, Back Pressure: 52, RT–3.94 min.

Example 12 (Homochiral)

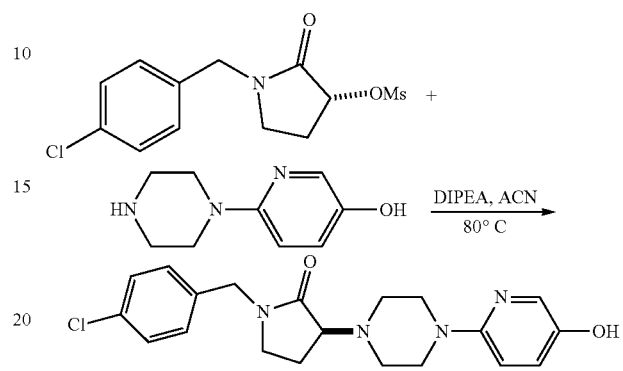

To a solution of 6-(piperazin-1-yl)pyridin-3-ol (20 mg, 0.112 mmol) in Acetonitrile (2 mL) and DIPEA (0.058 mL, 0.335 mmol) heated to 80° C. was added ((S)-1-(4-chlorobenzyl)-2-oxopyrrolidin-3-yl methanesulfonate (50.8 mg, 0.167 mmol) in Acetonitrile (1 mL) over 1 min. The mixture was then stirred at 80° C. for 16 h. The mixture was cool to RT. Then concentrated to get crude compound. The crude was purified by SCP. The crude material was purified via preparative LC/MS with the following conditions: Waters Xbridge C18, 19×150 mm, 5 μm; Guard Column: Waters XBridge C18, 19×10 mm, 5 μm; Mobile Phase A:5:95 Acetonitrile:water with 0.1% TFA; Mobile Phase B: 95:5 Acetonitrile:water with 0.1% TFA; Gradient:5-25% B over 25 minutes, followed by a 10 minute hold at 25% B and 5 minute hold at 100% B; Flow:15 ml/min. Fractions containing the desired product were combined and dried using a Genevac centrifugal evaporator to get (R)-1-(4-chlorobenzyl)-3-(4-(5-hydroxypyridin-2-yl)piperazin-1-yl)pyrrolidin-2-one (26 mg, 0.064 mmol, 57.2% yield) as pale yellow solid. Two analytical LC/MS injections were used to determine the final purity.

Injection 1 conditions: Column: Ascentis Express C18 (50×2.1) mm, 2.7 μm; Mobile Phase A: 5:95 Acetonitrile:water with 10 mM NH4OAc; Mobile Phase B: 95:5 Acetonitrile:water with 10 mM NH4OAc; Temperature: 50° C.; Gradient:0-100% B over 3 minutes; Flow: 1.1 ml/min.

Injection 2 conditions: Column: Ascentis Express C18 (50×2.1) mm, 2.7 μm; Mobile Phase A: 5:95 Acetonitrile:water with 0.1% TFA; Mobile Phase B: 95:5 Acetonitrile:water with 0.1% TFA; Temperature: 50° C.; Gradient:0-100% B over 3 minutes; Flow:1.1 ml/min.

$^1$H NMR: (400 MHz, METHANOL-$d_4$) □=7.70-7.69 (m, 1H), 7.47-7.44 (m, 1H), 7.41-7.38 (m, 2H), 7.33-7.29 (m, 2H), 7.12-7.09 (m, 1H), 4.59-4.45 (m, 2H), 4.25-4.19 (m, 1H), 3.74-3.60 (m, 6H), 3.44-3.35 (m, 3H), 3.29-3.23 (m, 2H), 2.50-2.42 (m, 1H), 2.27-2.18 (m, 1H).

LCMS: A: 95% Water: 5% Acetonitrile; 10 mM NH4OAC, B: 5% Water:95% Acetonitrile; 10 mM NH4OAC, Flow: 1.1 ml/min, Temp: 50° C., Column: Ascentis Express C18 (50×2.1) mm, 2.7 μm, Time (min): 0-3, % B: 0-100, RT–1.33 min, M(+1)–387.

Chiral screening: Injection Volume: 10, Co-Solvent: 0.3% DEA in Methanol, Column: Chiralpak AS H 4 (250×4.6) mm, 5 u, Column Temperature: 26.7, Total Flow:3, CO2

Example 13 P1 (Homochiral): 1-(4-(difluoromethoxy)-3-fluorophenyl)-3-(4-(5-hydroxypyridin-2-yl)piperazin-1-yl)pyrrolidin-2-one

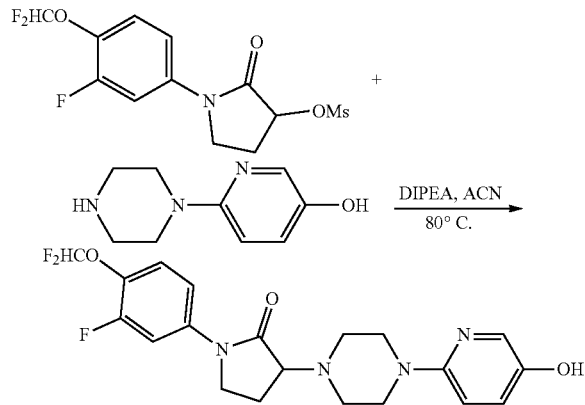

To a suspension of 6-(piperazin-1-yl)pyridin-3-ol (39.6 mg, 0.221 mmol) in Acetonitrile (10 mL) was added DIPEA (0.116 ml, 0.663 mmol) and heated the reaction mass to 50° C. for 10 minutes. At this temperature was added 1-(4-(difluoromethoxy)-3-fluorophenyl)-2-oxopyrrolidin-3-yl methanesulfonate (75 mg, 0.221 mmol) in Acetonitrile (1 mL) and stirred the reaction mass at 80° C. for 18 h. The mixture was cool to RT. Then concentrated to get crude compound. The crude was purified by SCP. The crude material was purified via preparative LC/MS with the following conditions: Waters Xbridge C18, 19×150 mm, 5 μm; Guard Column: Waters XBridge C18, 19×10 mm, 5 μm; Mobile Phase A:5:95 Acetonitrile:water with 0.1% TFA; Mobile Phase B: 95:5 Acetonitrile:water with 0.1% TFA; Gradient:5-25% B over 25 minutes, followed by a 10 minute hold at 25% B and 5 minute hold at 100% B; Flow:15 ml/min. Fractions containing the desired product were combined and dried using a Genevac centrifugal evaporator to get 1-(4-(difluoromethoxy)-3-fluorophenyl)-3-(4-(5-hydroxypyridin-2-yl)piperazin-1-yl)pyrrolidin-2-one (8.5 mg, 0.020 mmol, 9.01% yield) as pale yellow solid. Two analytical LC/MS injections were used to determine the final purity.

Injection 1 conditions: Column: Ascentis Express C18 (50×2.1) mm, 2.7 μm; Mobile Phase A: 5:95 Acetonitrile:water with 10 mM NH4OAc; Mobile Phase B: 95:5 Acetonitrile:water with 10 mM NH4OAc; Temperature: 50° C.; Gradient:0-100% B over 3 minutes; Flow: 1.1 ml/min.

Injection 2 conditions: Column: Ascentis Express C18 (50×2.1) mm, 2.7 μm; Mobile Phase A: 5:95 Acetonitrile:water with 0.1% TFA; Mobile Phase B: 95:5 Acetonitrile:water with 0.1% TFA; Temperature: 50° C.; Gradient:0-100% B over 3 minutes; Flow:1.1 ml/min.

LCMS: A: 95% Water: 5% Acetonitrile; 10 mM NH4OAC, B: 5% Water:95%, Acetonitrile; 10 mM NH4OAC, Flow: 1.1 ml/min, Temp:50° C., Column: Ascentis Express C18 (50×2.1) mm, 2.7 μm, Time (min): 0-3, % B: 0-100, RT–1.331 min M(+1)–423.

$^1$H NMR: (400 MHz, METHANOL-d$_4$) □=7.85 (dd, J=2.5, 13.1 Hz, 1H), 7.77 (d, J=2.5 Hz, 1H), 7.45-7.40 (m, 1H), 7.37-7.30 (m, 1H), 7.17 (dd, J=3.0, 9.0 Hz, 1H), 7.03-6.64 (m, 2H), 3.91-3.74 (m, 3H), 3.42 (t, J=5.0 Hz, 4H), 3.07 (td, J=5.1, 10.8 Hz, 2H), 2.82-2.74 (m, 2H), 2.42-2.32 (m, 1H), 2.29-2.16 (m, 1H).

Chiral screening: Injection Volume: 5, Co-Solvent: 0.3% DEA in Methanol, Column: Lux cellulose-2(4.6*250) mm5 u, Column Temperature: 21.2, CO2 Flow Rate: 2.4, Co-Solvent Flow Rate: 1.6, Co-Solvent: 40, Total Flow: 4, Back pressure: 98, RT–3.86 min.

Example 13 P2 (Homochiral): 1-(4-(difluoromethoxy)-3-fluorophenyl)-3-(4-(5-hydroxypyridin-2-yl)piperazin-1-yl)pyrrolidin-2-one

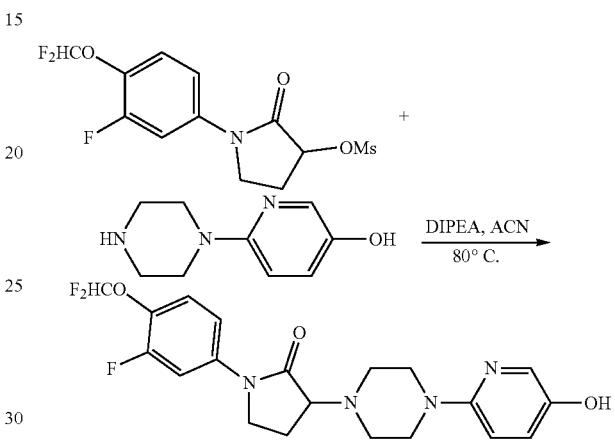

To a suspension of 6-(piperazin-1-yl)pyridin-3-ol (39.6 mg, 0.221 mmol) in

Acetonitrile (10 mL) was added DIPEA (0.116 ml, 0.663 mmol) and heated the reaction mass to 50° C. for 10 minutes. At this temperature was added 1-(4-(difluoromethoxy)-3-fluorophenyl)-2-oxopyrrolidin-3-yl methanesulfonate (75 mg, 0.221 mmol) in Acetonitrile (1 mL) and stirred the reaction mass at 80° C. for 18 h. The completion of the reaction was monitored by LCMS. The mixture was cool to RT. Then concentrated to get crude compound. The crude was purified by SCP. The crude material was purified via preparative LC/MS with the following conditions: Waters Xbridge C18, 19×150 mm, 5 μm; Guard Column: Waters XBridge C18, 19×10 mm, 5 μm; Mobile Phase A:5:95 Acetonitrile:water with 0.1% TFA; Mobile Phase B: 95:5 Acetonitrile:water with 0.1% TFA; Gradient:5-25% B over 25 minutes, followed by a 10 minute hold at 25% B and 5 minute hold at 100% B; Flow:15 ml/min. Fractions containing the desired product were combined and dried using a Genevac centrifugal evaporator to get 1-(4-(difluoromethoxy)-3-fluorophenyl)-3-(4-(5-hydroxypyridin-2-yl)piperazin-1-yl)pyrrolidin-2-one (21 mg, 0.049 mmol, 22.27% yield) as pale yellow solid. Two analytical LC/MS injections were used to determine the final purity.

Injection 1 conditions: Column: Ascentis Express C18 (50×2.1) mm, 2.7 μm; Mobile Phase A: 5:95 Acetonitrile:water with 10 mM NH4OAc; Mobile Phase B: 95:5 Acetonitrile:water with 10 mM NH4OAc; Temperature: 50° C.; Gradient:0-100% B over 3 minutes; Flow: 1.1 ml/min.

Injection 2 conditions: Column: Ascentis Express C18 (50×2.1) mm, 2.7 μm; Mobile Phase A: 5:95 Acetonitrile:water with 0.1% TFA; Mobile Phase B: 95:5 Acetonitrile:water with 0.1% TFA; Temperature: 50° C.; Gradient:0-100% B over 3 minutes; Flow:1.1 ml/min.

LCMS: A: 95% Water: 5% Acetonitrile; 10 mM NH4OAC, B: 5% Water:95%, Acetonitrile; 10 mM NH4OAC, Flow: 1.1 ml/min, Temp:50° C., Column: Ascentis Express C18 (50×2.1) mm, 2.7 µm, Time (min): 0-3, % B: 0-100, RT–1.332 min M(+1)–423.

¹H NMR: (400 MHz, METHANOL-d₄) □=7.85 (dd, J=2.5, 12.5 Hz, 1H), 7.76 (d, J=3.0 Hz, 1H), 7.45-7.40 (m, 1H), 7.36-7.31 (m, 1H), 7.19-7.15 (m, 1H), 7.02-6.64 (m, 2H), 3.89-3.74 (m, 3H), 3.44-3.40 (m, 4H), 3.07 (td, J=5.3, 10.9 Hz, 2H), 2.78 (td, J=5.1, 10.8 Hz, 2H), 2.41-2.33 (m, 1H), 2.29-2.18 (m, 1H).

Chiral screening: Injection Volume: 5, Co-Solvent: 0.3% DEA in Methanol, Column: Lux cellulose-2(4.6*250) mm5 u, Column Temperature: 21.2, CO2 Flow Rate: 2.4, Co-Solvent Flow Rate: 1.6, Co-Solvent: 40, Total Flow: 4, Back pressure: 98, RT–3.17 min.

Example 14 (P1 & P2)

Example 14 P1 (Homochiral)

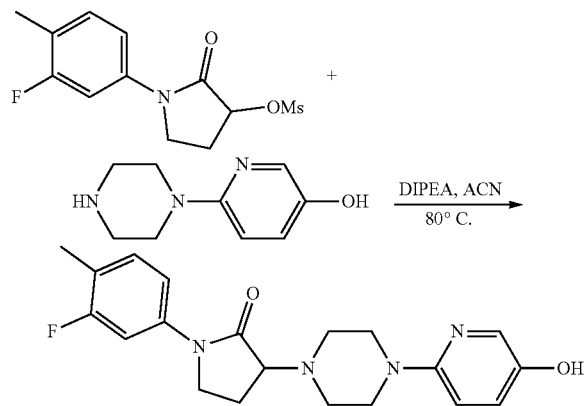

To a stirred solution of 6-(piperazin-1-yl)pyridin-3-ol (0.04 g, 0.223 mmol) in Acetonitrile (6 mL) was added DIPEA (0.117 mL, 0.670 mmol) at RT. The reaction mixture was heated to 50° C. and was added 1-(3-fluoro-4-methylphenyl)-2-oxopyrrolidin-3-yl methanesulfonate (0.115 g, 0.402 mmol) in Acetonitrile (2 mL) slowly drop wise. The reaction mixture was heated to 80° C. for 18 h. The completion of the reaction was monitored by LCMS. The mixture was to RT. Then concentrated to get crude compound. The crude was purified by SCP. The crude material was purified via preparative LC/MS with the following conditions: Waters Xbridge C18, 19×150 mm, 5 µm; Guard Column:Waters XBridge C18, 19×10 mm, 5 µm; Mobile Phase A:5:95 Acetonitrile:water with 10 mM NH4OAc; Mobile Phase B: 95:5 Acetonitrile:water with 10 mM NH4OAc; Gradient:10-35% B over 25 minutes, followed by a 10 minute hold at 35% B and 5 minute hold at 100% B; Flow:15 ml/min. Fractions containing the desired product were combined and dried using a Genevac centrifugal evaporator to get 1-(3-fluoro-4-methylphenyl)-3-(4-(5-hydroxypyridin-2-yl)piperazin-1-yl)pyrrolidin-2-one (16.5 mg 0.0445 mmol, 19.95%) as pale yellow solid. Two analytical LC/MS injections were used to determine the final purity.

Injection 1 conditions: Column: Ascentis Express C18 (50×2.1) mm, 2.7 µm; Mobile Phase A: 5:95 Acetonitrile: water with 10 mM NH4OAc; Mobile Phase B: 95:5 Acetonitrile:water with 10 mM NH4OAc; Temperature: 50° C.; Gradient:0-100% B over 3 minutes; Flow: 1.1 ml/min.

Injection 2 conditions: Column: Ascentis Express C18 (50×2.1) mm, 2.7 µm; Mobile Phase A: 5:95 Acetonitrile: water with 0.1% TFA; Mobile Phase B: 95:5 Acetonitrile: water with 0.1% TFA; Temperature: 50° C.; Gradient:0-100% B over 3 minutes; Flow:1.1 ml/min.

¹H NMR: (400 MHz, METHANOL-d₄) □=7.76 (d, J=3.0 Hz, 1H), 7.57 (d, J=12.0 Hz, 1H), 7.32-7.23 (m, 1H), 7.16 (dd, J=3.0, 9.0 Hz, 1H), 6.80 (d, J=9.0 Hz, 1H), 4.60 (s, 1H), 3.88-3.71 (m, 2H), 3.51 (s, 1H), 3.42 (t, J=5.0 Hz, 1H), 3.16 (d, J=1.5 Hz, 1H), 3.10- 3.00 (m, 1H), 2.77 (dd, J=5.5, 10.5 Hz, 1H), 2.32-2.20 (m, 1H).

LCMS: A: 95% Water: 5% Acetonitrile; 10 mM NH4OAC, B: 5% Water:95%, cetonitrile; 10 mM NH4OAC, Flow: 1.1 ml/min, Temp:50° C., Column: Ascentis Express C18 (50×2.1) mm, 2.7 µm, Time (min): 0-3, % B: 0-100, RT–1.32 min, M(+1)–371.

Chiral screening: Injection Volume: 5, Co-Solvent: 0.3% DEA in Methanol, Column: Lux cellulose-4 (4.6×250) mm 5 u, Column Temperature: 18.8, CO2 Flow Rate: 2.4, Co-Solvent Rate: 1.6, Co-Solvent %: 40, Total Flow: 4, Back Pressure:102, RT–4.09 min, 97.6% ee.

Example 14 P2 (Homochiral)

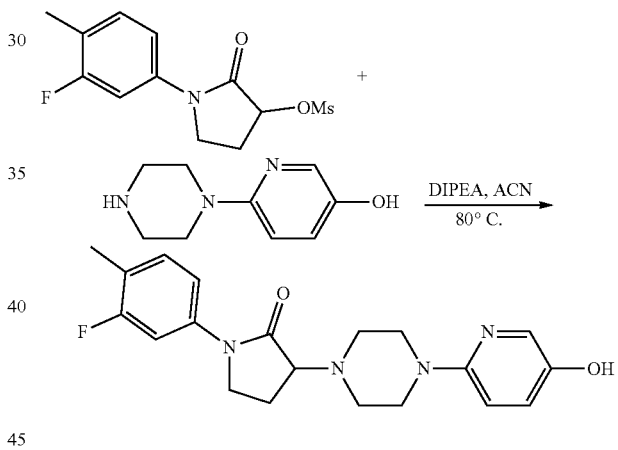

To a stirred solution of 6-(piperazin-1-yl)pyridin-3-ol (0.04 g, 0.223 mmol) in Acetonitrile (6 mL) was added DIPEA (0.117 mL, 0.670 mmol) at RT. The reaction mixture was heated to 50° C. and was added 1-(3-fluoro-4-methylphenyl)-2-oxopyrrolidin-3-yl methanesulfonate (0.115 g, 0.402 mmol) in Acetonitrile (2 mL) slowly drop wise. The reaction mixture was heated to 80° C. for 18 h. The completion of the reaction was monitored by LCMS. The mixture was allowed to cool to RT. Then concentrated to get crude compound. The crude was purified by SCP. The crude material was purified via preparative LC/MS with the following conditions: Waters Xbridge C18, 19×150 mm, 5 µm; Guard Column: Waters XBridge C18, 19×10 mm, 5 µm; Mobile Phase A:5:95 Acetonitrile:water with 0.1% TFA; Mobile Phase B: 95:5 Acetonitrile:water with 0.1% TFA; Gradient:5-25% B over 25 minutes, followed by a 10 minute hold at 25% B and 5 minute hold at 100% B; Flow:15 ml/min. Fractions containing the desired product were combined and dried using a Genevac centrifugal evaporator to get 1-(3-fluoro-4-methylphenyl)-3-(4-(5-hydroxypyridin-2-yl)piperazin-1-yl)pyrrolidin-2-one (13 mg, 0.035 mmol, 15.10% yield).

¹H NMR: (400 MHz, METHANOL-d₄) □=7.76 (d, J=2.5 Hz, 1H), 7.63-7.50 (m, 1H), 7.33-7.23 (m, 2H), 7.16 (dd, J=3.0, 9.0 Hz, 1H), 6.80 (d, J=9.0 Hz, 1H), 4.60 (s, 1H), 3.89-3.69 (m, 3H), 3.50 (d, J=1.5 Hz, 1H), 3.42 (t, J=5.3 Hz, 2H), 3.19-3.14 (m, 1H), 3.06 (dd, J=5.3, 11.3 Hz, 2H), 2.83-2.67 (m, 2H), 2.36 (br. S., 1H), 2.28-2.11 (m, 2H).

LCMS: A: 95% Water: 5% Acetonitrile; 10 mM NH4OAC, B: 5% Water:95%, Acetonitrile; 10 mM NH4OAC, Flow: 1.1 ml/min, Temp:50° C., Column: Ascentis Express C18 (50×2.1) mm, 2.7 μm, Time (min): 0-3, % B: 0-100, LCMS RT–1.32 min, M(+1)–371.

Chiral screening: Injection Volume: 5, Co-Solvent:0.3% DEA in Methanol, Column: Lux cellulose-4 (4.6×250) mm 5 u, Column Temperature: 21.6, CO2 Flow Rate: 2.4, Co-Solvent Flow Rate: 1.6, Co-Solvent %: 40, Total Flow: 4, Back Pressure: 97, RT–4.73 min.

Example 15 (Homochiral)

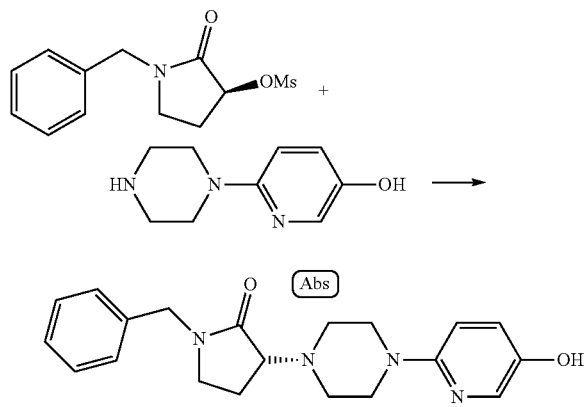

To a stirred solution of 6-(piperazin-1-yl)pyridin-3-ol (0.015 g, 0.084 mmol) in DMF (3 mL) was added TEA (0.035 mL, 0.251 mmol) and (S)-1-benzyl-2-oxopyrrolidin-3-yl methanesulfonate (0.045 g, 0.167 mmol) at RT. The reaction mixture was stirred at 120° C. for 2 h in microwave. Major desired product mass by LCMS. The reaction mixture as such was submitted to SCP. The crude compound was purified by SCP to obtain (R)-1-benzyl-3-(4-(5-hydroxypyridin-2-yl) piperazin-1-yl) pyrrolidin-2-one (2 mg, 5.39 μma 6.44% yield) as pale yellow solid.

LCMS: A: 95% Water: 5% Acetonitrile; 10 mM NH4OAC, B: 5% Water:95% Acetonitrile; 10 mM NH4OAC, Flow: 1.1 ml/min, Temp:50° C., Column: Ascentis Express C18 (50×2.1) mm, 2.7 μm, Time (min): 0-3, % B: 0-100, RT–1.161 min, M(+1)–353.

Chiral screening: Injection Volume: 5, Co-Solvent: 0.3% DEA in Methanol, Column: chiralcel-ASH (250*4.6)5 u, Column Temperature: 24.6, CO2 Flow Rate: 2.4, Co-Solvent Flow Rate: 1.6, Co-Solvent: 40, Total Flow: 4, Back Pressure: 103, RT–2.3 min.

1H NMR: 400 MHz, DMSO-d6: δ 2.08 (s, 2H), 2.92 (bs, 2H), 3.18-3.22 (m, 6H), 3.37-3.42 (m, 2H), 4.34-4.46 (m, 3H), 6.75 (s, 1H), 6.96 (s, 1H), 7.07-7.09 (m, 1H), 7.22-7.25 (m, 2H), 7.28-7.31 (m, 1H), 7.35-7.39 (m, 2H), 7.75 (d, J=2.80 Hz, 1H).

Example 16 (P1, P2, P3 & P4): 3-(4-(5-hydroxypyridin-2-yl)-2-methylpiperazin-1-yl)-1-(4-methylbenzyl)pyrrolidin-2-one

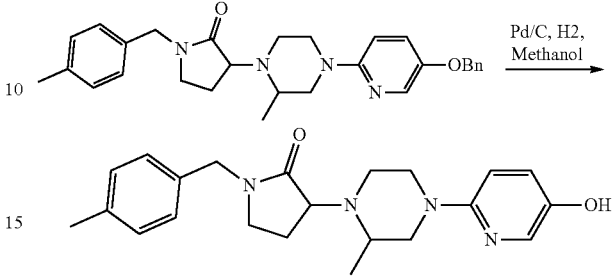

To a solution of 3-(4-(5-(benzyloxy)pyridin-2-yl)-2-methylpiperazin-1-yl)-1-(4-methylbenzyl)pyrrolidin-2-one (650 mg, 1.381 mmol) in Methanol (20 mL) was added Pd/C (147 mg, 1.381 mmol) at RT. The reaction mixture was stirred under hydrogen pressure for 18 h. The reaction mixture was filtered through celite and was washed with methanol (100 mL), filtrate was dried over Na₂SO₄ and evaporated under reduced pressure to get crude residue. The crude was purified over C18 Reverse phase silicycle column eluted with 50% Acetonitrile+10 mm Ammonium acetate to give pure fractions, which on evaporation gave 3-(4-(5-hydroxypyridin-2-yl)-2-methylpiperazin-1-yl)-1-(4-methylbenzyl)pyrrolidin-2-one (420 mg, 0.993 mmol, 71.9% yield) as pale yellow solid.

LCMS: RT: 1.93 min ACN/H₂O with HCOONH₄, Ascentis Express C18 (50×2.1 mm-2.7 μm), gradient=1.7 min, wavelength=220 nm; MS (ES): m/z 381. M+H.

SFC: CO2 3.0_Colvent_100.met; Flow:—total flow 3, CO2 flow rate 2.1, Co-solvent (0.3% DEA in Methanol) 0.9; Column:—Chiralpak AD H (250×4.6) mm 5 u; RT 3.9 min; Purity@ 217 nm:32%, RT 4.7 min; Purity@ 217 nm:16%, RT 6 min; Purity@ 217 nm:16%, RT 10 min; Purity@ 217 nm:33%.

Preparative SFC Conditions: Column/dimensions: Chiralcel OD-H (250×21) mm, 5 u, % CO2: 75%, % Co solvent: 25% (0.25% DEA in Methanol), Total Flow: 60.0 g/min Back Pressure: 100 bar, Temperature: 25° C., UV: 245, Peak number: Retention Time::Peak 1: 3.90::Peak 2: 4.70::Peak 3: 6.00::Peak 4: 10.00, Solubility: 60 ml in Methanol, Loadability/Inj: 5.0 mg/mL, Total No of injections:120 Total Time for purification 15.0 hrs. Instrument details: Make/Model: Thar SFC-80.

For P1 (Homochiral)

3-(4-(5-hydroxypyridin-2-yl)-2-methylpiperazin-1-yl)-1-(4-methylbenzyl)pyrrolidin-2-one

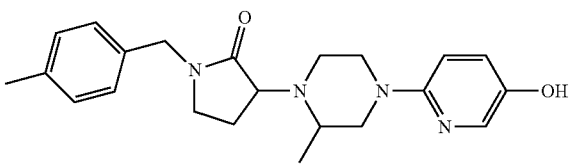 [SMILES: Cc1ccc(CN2CCC(N3CCN(c4ccc(O)cn4)CC3C)C2=O)cc1]

LCMS: Column-Ascentis Express C₈ (50×2.1 mm-2.7 μm), Mphase A: 2% ACN—98% H20-10 mM NH4C00H, Mphase B: 98% ACN—2% H20-10 mM NH4C00H, Flow=1 ML/MIN, Time: % B::0.0:0.0::1.7:100.0::4.0:100.0, RT–1.774 min, M(+1)–381.

$^1$H NMR: (400 MHz, METHANOL-$d_4$) δ ppm 7.75 (dd, J=3.01, 0.50 Hz, 1H) 7.13-7.21 (m, 5H) 6.77 (dd, J=9.04, 0.44 Hz, 1H) 4.55 (s, 1H) 4.42 (s, 1H) 4.13 (t, J=9.00 Hz, 1H) 3.77-3.88 (m, 2H) 3.36-3.39 (m, 2H) 3.24-3.30 (m, 2H) 3.02 (d, J=0.25 Hz, 1H) 2.95 (td, J=11.66, 3.17 Hz, 1H) 2.88 (d, J=0.69 Hz, 1H) 2.58-2.73 (m, 4H) 2.34 (s, 3H) 2.07-2.19 (m, 1H) 1.95-2.05 (m, 3H) 1.18-1.24 (m, 3H).

Chiral purity: Injection Volume: 10, Co-Solvent: 0.3% DEA in Methanol, Column: Chiralcel OD-H (4.6×250) mm, 5 u, Column Temperature: 26, Total Flow: 3, CO2 Flow Rate: 2.25, Co-Solvent Flow Rate: 0.75, Co-Solvent: 25, Back Pressure: 99, RT–5.3 min.

For P2 (Homochiral)

3-(4-(5-hydroxypyridin-2-yl)-2-methylpiperazin-1-yl)-1-(4-methylbenzyl)pyrrolidin-2-one

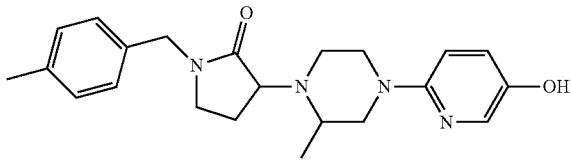

LCMS: Column-Ascentis Express $C_8$ (50×2.1 mm-2.7 μm), Mphase A: 2% ACN—98% H20-10 mM NH4C00H, Mphase B: 98% ACN—2% H20-10 mM NH4C00H, Flow=1 ML/MIN, Time: % B::0.0:0.0::1.7:100.0::4.0:100.0, RT–1.751 min, M(+1)–381.

$^1$H NMR: (400 MHz, METHANOL-$d_4$) d ppm 7.75 (dd, J=2.98, 0.53 Hz, 1H) 7.13-7.20 (m, 7H) 6.77 (dd, J=9.04, 0.50 Hz, 1H) 4.49 (d, J=14.56 Hz, 1H) 4.30-4.35 (m, 1H) 4.05 (dd, J=9.60, 7.72 Hz, 1H) 3.74-3.86 (m, 3H) 3.36-3.45 (m, 3H) 3.21-3.31 (m, 2H) 2.99-3.03 (m, 2H) 2.89-2.99 (m, 3H) 2.88 (d, J=0.63 Hz, 2H) 2.57-2.70 (m, 3H) 2.23-2.35 (m, 3H) 1.94-2.08 (m, 3H) 1.24 (s, 3H).

Chiral purity: Injection Volume: 10, Co-Solvent: 0.3% DEA in Methanol, Column: Chiralcel OD-H (4.6×250) mm, 5 u, Column Temperature: 25.9, Total Flow: 3, CO2 Flow Rate: 2.25, Co-Solvent Flow Rate: 0.75, Co-Solvent %: 25, Back Pressure: 103, RT–6.4 min.

For P3 (Homochiral)

3-(4-(5-hydroxypyridin-2-yl)-2-methylpiperazin-1-yl)-1-(4-methylbenzyl)pyrrolidin-2-one

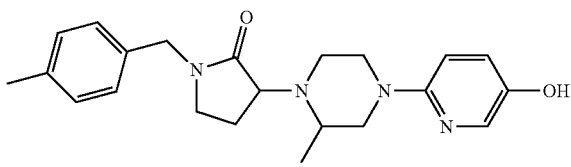 [SMILES: Cc1ccc(CN2CCC(N3CCN(c4ccc(O)cn4)CC3(C)C)C2=O)cc1]

LCMS: Column-Ascentis Express $C_8$ (50×2.1 mm-2.7 μm), Mphase A: 2% ACN—98% H20-10 mM NH4C00H, Mphase B: 98% ACN—2% H20-10 mM NH4C00H, Flow=1 ML/MIN, Time: % B::0.0:0.0::1.7:100.0::4.0:100.0, RT–1.774 min, M(+1)–381.

$^1$H NMR: (400 MHz, METHANOL-$d_4$) d ppm 7.75 (dd, J=3.01, 0.44 Hz, 1H) 7.14-7.22 (m, 5H) 6.75-6.80 (m, 1H) 4.50-4.56 (m, 1H) 4.38-4.44 (m, 1H) 4.13 (t, J=9.00 Hz, 1H) 3.78-3.88 (m, 2H) 3.36-3.38 (m, 2H) 3.24-3.30 (m, 2H) 3.02 (d, J=0.31 Hz, 1H) 2.95 (td, J=11.64, 3.20 Hz, 1H) 2.88 (d, J=0.63 Hz, 1H) 2.59-2.74 (m, 6H) 2.34 (s, 4H) 2.08-2.19 (m, 1H) 1.94-2.06 (m, 4H) 1.19-1.24 (m, 3H).

Chiral purity: Injection Volume: 10, Co-Solvent: 0.3% DEA in Methanol, Column: Chiralcel OD-H (4.6×250) mm, 5 u, Column Temperature: 25.9, Total Flow: 3, CO2 Flow Rate: 2.25, Co-Solvent Flow Rate: 0.75, Co-Solvent: 25, Back Pressure: 100, RT–7.6 min.

For P4 (Homochiral)

3-(4-(5-hydroxypyridin-2-yl)-2-methylpiperazin-1-yl)-1-(4-methylbenzyl)pyrrolidin-2-one

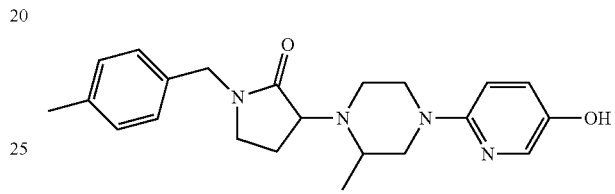

LCMS: Column-Ascentis Express $C_8$ (50×2.1 mm-2.7 μm), Mphase A: 2% ACN—98% H20-10 mM NH4C00H, Mphase B: 98% ACN—2% H20-10 mM NH4C00H, Flow=1 ML/MIN, Time: % B::0.0:0.0::1.7:100.0::4.0:100.0, RT–1.750 min, M(+1)–381.

$^1$H NMR: (400 MHz, METHANOL-$d_4$) d ppm 7.75 (dd, J=3.01, 0.50 Hz, 1H) 7.13-7.20 (m, 5H) 6.77 (d, J=8.66 Hz, 1H) 4.49 (d, J=14.56 Hz, 1H) 4.29-4.35 (m, 1H) 4.05 (dd, J=9.60, 7.72 Hz, 1H) 3.75-3.86 (m, 2H) 3.37-3.44 (m, 4H) 3.21-3.31 (m, 1H) 2.87-3.02 (m, 1H) 2.57-2.69 (m, 1H) 2.34 (s, 2H) 2.22-2.31 (m, 1H) 1.98-2.07 (m, 1H) 1.93-1.96 (m, 6H) 1.24 (s, 3H).

Chiral purity: Injection Volume: 10, Co-Solvent: 0.3% DEA in Methanol, Column: Chiralcel OD-H (4.6×250) mm, 5 u, Column Temperature: 24.8, Total Flow: 3, CO2 Flow Rate: 2.25, Co-Solvent Flow Rate: 0.75, Co-Solvent: 25, Back Pressure: 100, RT–15.1 min.

Example 17 (Homochiral)

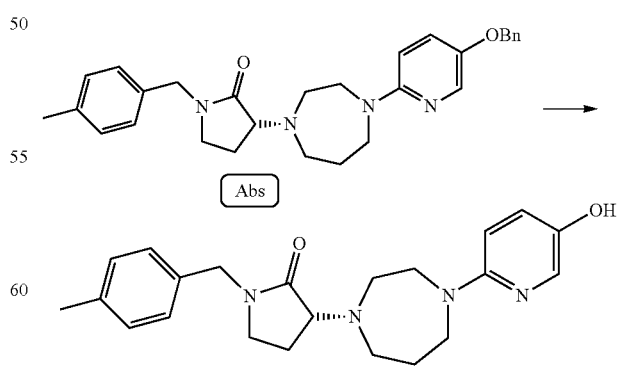

Preparation:

To a stirred solution of (R)-3-(4-(5-(benzyloxy)pyridin-2-yl)-1,4-diazepan-1-yl)-1-(4-methylbenzyl)pyrrolidin-2- one (0.1 g, 0.212 mmol) in Methanol (10 mL) was added Pd/C (0.023 g, 0.212 mmol) at RT. The reaction mixture was connected to a hydrogen bladder through vaccume bend and was stirred at RT for 18 h. Major desired product mass by LCMS. The reaction mixture was filtered through celeite and the filtrate was concentrated to get crude 0.04 g. The crude was submitted to SCP. The crude compound was purified by SCP to obtain (R)-3-(4-(5-hydroxypyridin-2-yl)-1,4-diazepan-1-yl)-1-(4-methylbenzyl)pyrrolidin-2-one (6.5 mg, 0.017 mmol, 7.88% yield) as pale yellow solid.

LCMS: Solvent A: 5% ACN, 95% Water, 10 mM NH4OAC, Solvent B: 95% ACN, 5% Water, 10 mM NH4OAC, Flow Rate: 4 ml/min, Temp: 50° C., Column: Ascentis Express C18 (50×4.6) mm, 2.7 µm, Time (min): 0-4, % B:0-100, RT–1.93 min, M(+1)–381.

Chiral screening: Injection Volume: 3, Co-Solvent: 0.3% DEA in Methanol, Column: Chiralpak AD H (250×4.6) mm 5 u, Column Temperature: 26.4, Total Flow: 4, CO2 Flow Rate: 1.95, Co-Solvent Flow Rate: 1.05, Co-Solvent: 35, Back Pressure: 99, RT–9.73 min.

1H NMR: 400 MHz, DMSO-d6: δ 1.80 (bs, 3H), 2.08 (d, J=6.40 Hz, 1H), 2.29 (s, 3H), 2.68-2.68 (m, 2H), 2.91 (bs, 1H), 3.02-3.10 (m, 2H), 3.11-3.19 (m, 2H), 3.52-3.55 (m, 3H), 3.60 (s, 2H), 4.24-4.35 (m, 2H), 6.47 (d, J=9.20 Hz, 1H), 7.01-7.04 (m, 1H), 7.08-7.16 (m, 4H), 7.68 (d, J=2.80 Hz, 1H), 8.66 (s, 1H).

Example 18 (Homochiral)

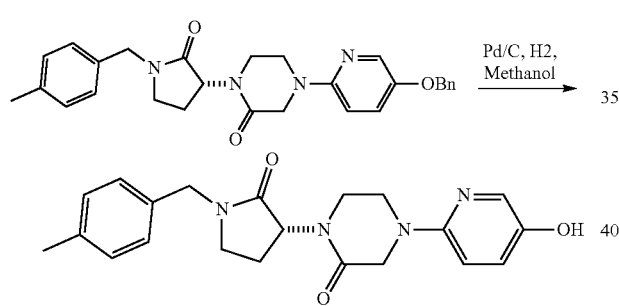

To a solution of (R)-4-(5-(benzyloxy)pyridin-2-yl)-1-(1-(4-methylbenzyl)-2-oxopyrrolidin-3-yl)piperazin-2-one (0.15 g, 0.182 mmol) in MeOH (5 mL) was added Pd/C (0.12 g, 0.113 mmol) and stirred at RT under hydrogen balloon pressure for 12 h. The completion of the reaction was monitored by LCMS. Reaction mass was filtered through celite and concentrated under reduced pressure to get crude 0.12 g. The crude was submitted to SCP. The crude was purified by SCP. The crude material was purified via preparative LC/MS with the following conditions: Waters Xbridge C18, 19×150 mm, 5 µm; Guard Column: Waters XBridge C18, 19×10 mm, 5 µm; Mobile Phase A:5:95 Methanol:water with 10 mM NH4OAc; Mobile Phase B: 95:5 Methanol:water with 10 mM NH4OAc; Gradient:15-60% B over 25 minutes, followed by a 10 minute hold at 60% B and 5 minute hold at 100% B; Flow:15 ml/min. Fractions containing the desired product were combined and dried using a Genevac centrifugal evaporator to get (R)-4-(5-hydroxypyridin-2-yl)-1-(1-(4-methylbenzyl)-2-oxopyrrolidin-3-yl)piperazin-2-one (21 mg, 0.055 mmol, 30.1% yield) as pale yellow solid.

LCMS: Solvent A: 5% ACN, 95% Water, 10 mM NH4OAC, Solvent B: 95% ACN, 5% Water, 10 mM NH4OAC, Flow Rate: 4 ml/min, Temp: 50° C., Column: Ascentis Express C18 (50×4.6) mm, 2.7 µm, Time (min): 0-4, % B:0-100, RT–1.735 min, M(+1)–381.

H-NMR: 400 MHz, DMSO-d6: δ 1.98-2.05 (m, 1H), 2.15-2.22 (m, 1H), 2.29 (s, 3H), 3.19-3.22 (m, 2H), 3.24-3.28 (m, 1H), 3.36-3.43 (m, 1H), 3.65 (t, J=28.00 Hz, 2H), 3.91-4.02 (m, 2H), 4.30 (d, J=14.80 Hz, 1H), 4.41 (d, J=14.80 Hz, 1H), 5.06 (t, J=19.20 Hz, 1H), 6.76 (d, J=8.80 Hz, 1H), 7.10 (dd, J=11.60, Hz, 1H), 7.13-7.17 (m, 4H), 7.76 (d, J=3.20 Hz, 1H), 9.05 (s, 1H).

Chiral Screening: Injection Volume: 3, Co-Solvent: 0.3% DEA in Methanol, Column: Chiralcel OD-H (4.6×250) mm, 5 u, Column Temperature: 25, Total Flow: 3, CO2 Flow Rate: 1.95, Co-Solvent Flow Rate: 1.05, Co-Solvent %: 35, Back Pressure: 99, RT–3.97 min.

Example 19 (Homochiral)

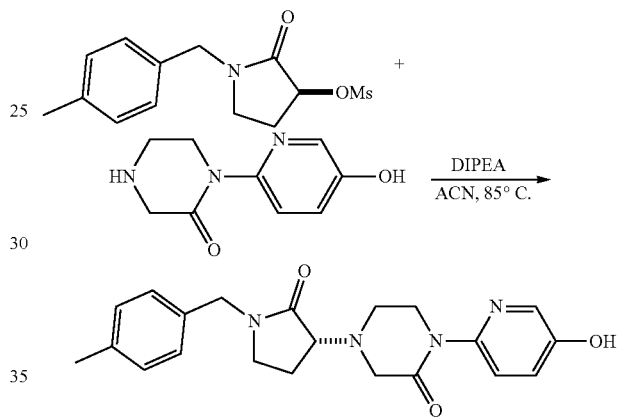

To a solution of 1-(5-hydroxypyridin-2-yl)piperazin-2-one, HCl (0.03 g, 0.131 mmol) in Acetonitrile (5 mL) was added DIPEA (0.068 mL, 0.392 mmol) heated to 60° C. for 30 minutes then was added (S)-1-(4-methylbenzyl)-2-oxopyrrolidin-3-yl methanesulfonate (0.041 g, 0.144 mmol) in Acetonitrile (1 mL) then heated to 85° C. for overnight. Reaction mass was concentrated under reduced pressure then dissolved in 2 mL of DMF was submitted to SCP. The crude material was purified via preparative LC/MS with the following conditions: Waters Xbridge C18, 19×150 mm, 5 µm; Guard Column: Waters XBridge C18, 19×10 mm, 5 µm; Mobile Phase A:5:95 Acetonitrile:water with 10 mM NH4OAc; Mobile Phase B: 95:5 Acetonitrile:water with 10 mM NH4OAc; Gradient:5-30% B over 25 minutes, followed by a 10 minute hold at 30% B and 5 minute hold at 100% B; Flow:15 ml/min. Fractions containing the desired product were combined and dried using a Genevac centrifugal evaporator to get (R)-1-(5-hydroxypyridin-2-yl)-4-(1-(4-methylbenzyl)-2-oxopyrrolidin-3-yl)piperazin-2-one (5 mg, 0.013 mmol, 10.06% yield) as pale yellow solid.

LCMS: Solvent A: 5% ACN, 95% Water, 10 mM NH4OAC, Solvent B: 95% ACN, 5% Water, 10 mM NH4OAC, Flow Rate: 4 ml/min, Temp: 50° C., Column: Ascentis Express C18 (50×4.6) mm, 2.7 µm, Time (min): 0-4, % B:0-100, RT–1.677 min, M(+1)–381.

H-NMR: 1H NMR: 400 MHz, MeOD: δ 2.03-2.09 (m, 1H), 2.25-2.26 (m, 1H), 2.34 (s, 3H), 2.97-3.00 (m, 1H), 3.24-3.30 (m, 2H), 3.34-3.35 (m, 1H), 3.47 (d, J=16.80 Hz, 1H), 3.72-3.81 (m, 2H), 3.85 (t, J=10.80 Hz, 2H), 4.40 (d,

J=14.40 Hz, 1H), 4.51 (d, J=14.80 Hz, 1H), 7.18-7.21 (m, 4H), 7.28 (dd, J=12.00, Hz, 1H), 7.44 (d, J=9.20 Hz, 1H), 8.01-8.02 (m, 1H).

Chiral Screening: Injection Volume: 5, Co-Solvent: 0.3% DEA in Methanol, Column: Lux cellulose-2(4.6×250) mm, 5 u, Column Temperature: 29.1, Total Flow: 4, CO2 Flow Rate: 2.4, Co-Solvent Flow Rate: 1.6, Co-Solvent: 40, Back Pressure: 98, RT–5.76 min.

Example 20 (Homochiral)

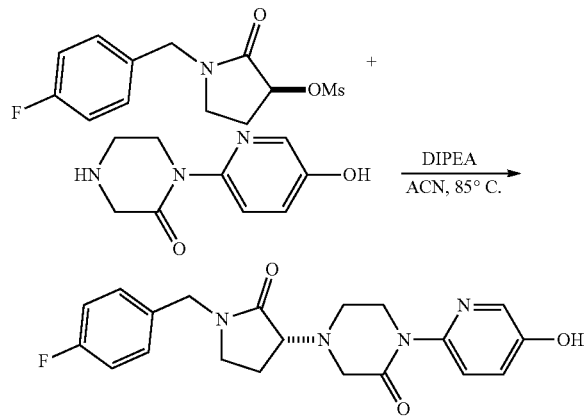

To a solution of 1-(5-hydroxypyridin-2-yl)piperazin-2-one, HCl (0.03 g, 0.131 mmol) in Acetonitrile (5 mL) was added DIPEA (0.068 mL, 0.392 mmol) heated to 60° C. for 30 minutes then was added (S)-1-(4-fluorobenzyl)-2-oxopyrrolidin-3-yl methanesulfonate (0.041 g, 0.144 mmol) in Acetonitrile (1 mL) then heated to 85° C. for overnight. The completion of the reaction was monitored by LCMS. Reaction mass was concentrated under reduced pressure then dissolved in 2 mL of DMF was submitted to SCP. The crude material was purified via preparative LC/MS with the following conditions: Waters Xbridge C18, 19×150 mm, 5 µm; Guard Column:Waters XBridge C18, 19×10 mm, 5 µm; Mobile Phase A:5:95 Acetonitrile:water with 10 mM NH4OAc; Mobile Phase B: 95:5 Acetonitrile:water with 10 mM NH4OAc; Gradient:5-30% B over 25 minutes, followed by a 10 minute hold at 30% B and 5 minute hold at 100% B; Flow:15 ml/min. Fractions containing the desired product were combined and dried using a Genevac centrifugal evaporator to get (R)-4-(1-(4-fluorobenzyl)-2-oxopyrrolidin-3-yl)-1-(5-hydroxypyridin-2-yl)piperazin-2-one (1 mg, 2.55 µmol, 1.952% yield) as pale yellow solid.

LCMS: Solvent A: 5% ACN, 95% Water, 10 mM NH4OAC, Solvent B: 95% ACN, 5% Water, 10 mM NH4OAC, Flow Rate: 4 ml/min, Temp: 50° C., Column: Ascentis Express C18 (50×4.6) mm, 2.7 µm, Time (min): 0-4, % B:0-100, RT–1.551 min, M(+1)–385.

H-NMR: 400 MHz, MeOD: δ 2.04-2.10 (m, 1H), 2.25-2.30 (m, 1H), 2.97-3.02 (m, 1H), 3.26-3.30 (m, 2H), 3.34-3.37 (m, 1H), 3.47 (d, J=16.40 Hz, 1H), 3.72-3.81 (m, 2H), 3.85 (t, J=11.20 Hz, 2H), 4.45 (d, J=14.80 Hz, 1H), 4.53 (d, J=14.40 Hz, 1H), 7.09-7.13 (m, 2H), 7.28 (dd, J=11.60, Hz, 1H), 7.31-7.35 (m, 2H), 7.44 (d, J=9.20 Hz, 1H), 8.02 (d, J=2.80 Hz, 1H).

Chiral screening: Injection Volume: 4, Co-Solvent: 0.3% DEA in Methanol, Column: Lux cellulose-2(4.6×250) mm, 5 u, Column Temperature: 23, Total Flow: 4, CO2 Flow Rate:2.4, Co-Solvent Flow Rate: 1.6, Co-Solvent %:40, Back Pressure: 99, RT–4.64 min.

Example 21 (P1 & P2)

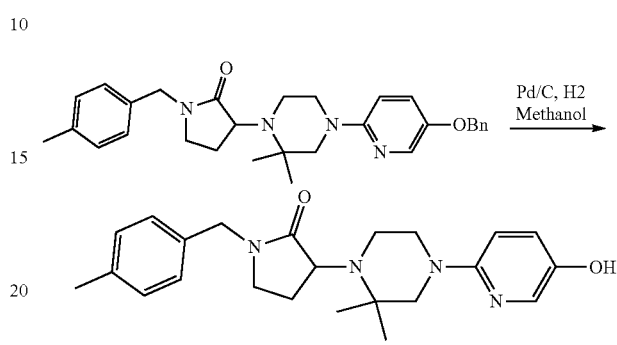

To a solution of 3-(4-(5-(benzyloxy)pyridin-2-yl)-2,2-dimethylpiperazin-1-yl)-1-(4-methylbenzyl)pyrrolidin-2-one (25 mg, 0.052 mmol) in MeOH (10 mL) was added Pd/C (1.098 mg, 10.32 µmol) at RT. The reaction mixture was stirred under Hydrogen bladder pressure for overnight. The completion of the reaction was monitored by LCMS. The reaction mixture was filtered through celite and the filtrate was evaporated under reduced pressure to get crude 30 mg. The crude compound was purified by SCP. The crude material was purified via preparative LC/MS with the following conditions: Waters Xbridge C18, 19×150 mm, 5 µm; Guard Column: Waters XBridge C18, 19×10 mm, 5 µm; Mobile Phase A:5:95 Acetonitrile:water with 10 mM NH4OAc; Mobile Phase B: 95:5 Acetonitrile:water, with 10 mM NH4OAc; Gradient:10-40% B over 25 minutes, followed by a 10 minute hold at 40% B and 5 minute hold at 100% B; Flow:15 ml/min. Fractions containing the desired product were combined and dried using a Genevac centrifugal evaporator to get (+/−)(4-(5-hydroxypyridin-2-yl)-2,2-dimethylpiperazin-1-yl)-1-(4-methylbenzyl)pyrrolidin-2-one (4 mg, 0.0101 mmol, 19.65% yield) as pale yellow solid.

Two analytical LC/MS injections were used to determine the final purity.

Injection 1 conditions: Column: Ascentis Express C18 (50×2.1) mm, 2.7 µm; Mobile Phase A: 5:95 Acetonitrile:water with 10 mM NH4OAc; Mobile Phase B: 95:5 Acetonitrile:water with 10 mM NH4OAc; Temperature: 50° C.; Gradient:0-100% B over 3 minutes; Flow: 1.1 ml/min.

Injection 2 conditions: Column: Ascentis Express C18 (50×2.1) mm, 2.7 µm; Mobile Phase A: 5:95 Acetonitrile:water with 0.1% TFA; Mobile Phase B: 95:5 Acetonitrile:water with 0.1% TFA; Temperature: 50° C.; Gradient:0-100% B over 3 minutes; Flow:1.1 ml/min.

The racemic mixture was separated by SFC.

Preparative SFC Conditions: Column/dimensions: Chiralpak AD-H (250×21) mm, 5 u, % CO2: 60%, % Co solvent: 40% (0.25% DEA in Methanol), Total Flow: 60.0 g/min, Back Pressure: 100 bar, Temperature: 25° C., UV: 220, Peak number: Retention Time::Peak 1: 3.40::Peak 2: 4.40, Solubility: 4 mL in Methanol.

For P1 (Homochiral): (4-(5-hydroxypyridin-2-yl)-2,2-dimethylpiperazin-1-yl)-1-(4-methylbenzyl)pyrrolidin-2-one

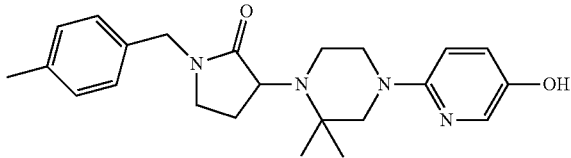 [SMILES: Cc1ccc(CN2CCC(N3CCN(c4ccc(O)cn4)CC3(C)C)C2=O)cc1]

HPLC: 95/5 to 5/95 H₂O/CH₃CN/0.05% TFA, flow=1 mL/min, gradient=15 min, Sunfire C₁₈ 4.6×150 mm: RT=10.32 min; Purity @220 nm: 89.04%; @254 nm: 91.96%. Xbridge Phenyl 3.5 um, 4.6×150 mm: RT=11.57 min; Purity @220 nm: 90.7%; @254 nm:94.77%.

LCMS: Column-Ascentis Express C18 (50×2.1 mm-2.7 μm), Mphase A: 10 mM NH4COOH IN WATER:ACN(98:02), Mphase B: 10 mM NH4COOH IN WATER:ACN(02:98), Flow=1 ML/MIN, Time: % B::0.0:0.0::1.7:100.0::3.0:100.0::3.2:0.0, RT−2.136 min, M(+1)−395.

SFC: CO2 3.0_Colvent_100.met; Flow:—total flow 3, CO2 flow rate 2.1, Co-solvent (0.3% DEA in Methanol) 0.9; Column:—Chiralpak AD H (250×4.6) mm 5μ; RT 4.12; Purity@ 217 nm:100%.

$^1$H NMR: (400 MHz, METHANOL-d₄) □ ppm 7.72 (dd, J=3.01, 0.56 Hz, 1H) 7.12-7.21 (m, 4H) 6.75 (dd, J=9.10, 0.56 Hz, 1H) 4.49-4.55 (m, 1H) 4.36-4.42 (m, 1H) 4.11 (t, J=9.25 Hz, 1H) 3.65-3.71 (m, 1H) 3.51 (dt, J=3.29, 1.62 Hz, 1H) 3.42 (dd, J=11.92, 1.63 Hz, 1H) 3.04-3.27 (m, 3H) 2.86-2.96 (m, 2H) 2.48 (dt, J=11.40, 3.58 Hz, 1H) 2.04-2.15 (m, 3H) 1.29 (s, 3H) 1.17 (s, 3H).

For P2 (Homochiral): 3-(4-(5-hydroxypyridin-2-yl)-2,2-dimethylpiperazin-1-yl)-1-(4-methylbenzyl)pyrolidin-2-one

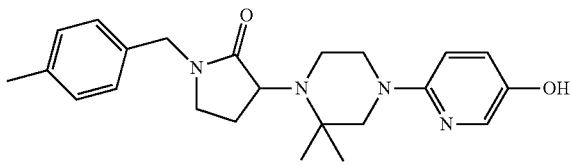

HPLC: 95/5 to 5/95 H₂O/CH₃CN/0.05% TFA, flow=1 mL/min, gradient=15 min, Sunfire C₁₈ 4.6×150 mm: RT=10.32 min; Purity @220 nm: 86.63%; @254 nm: 88.45%. Xbridge Phenyl 3.5 um, 4.6×150 mm: RT=11.566 min; Purity @220 nm: 89.57%; @254 nm:92.52%.

LCMS: Column-Ascentis Express C18 (50×2.1 mm-2.7 μm), Mphase A: 10 mM NH4COOH IN WATER:ACN(98:02), Mphase B: 10 mM NH4COOH IN WATER:ACN(02:98), Flow=1 ML/MIN, Time: % B::0.0:0.0::1.7:100.0::3.0:100.0::3.2:0.0, RT−2.133 min, M(+1)−395.

SFC: CO2 3.0_Colvent_100.met; Flow:—total flow 3, CO2 flow rate 2.1, Co-solvent (0.3% DEA in Methanol) 0.9; Column:—Chiralpak AD H (250×4.6) mm 5μ; RT 6.07; Purity@ 217 nm:100%.

$^1$H NMR: (400 MHz, METHANOL-d₄) δ ppm 7.71 (dd, J=3.04, 0.60 Hz, 1H) 7.11-7.21 (m, 5H) 6.76 (d, J=0.56 Hz, 1H) 4.53 (s, 1H) 4.34-4.42 (m, 1H) 4.11 (t, J=9.19 Hz, 1H) 3.65-3.71 (m, 1H) 3.38-3.51 (m, 1H) 3.18-3.25 (m, 2H) 3.03-3.16 (m, 1H) 2.86-2.96 (m, 2H) 2.47 (dt, J=11.28, 3.55 Hz, 1H) 2.04-2.11 (m, 1H) 1.27-1.33 (m, 3H) 1.16 (s, 3H).

Example 22 (P1 & P2)

Example 22 (P1) (Homochiral): 1-(4-chloro-3-fluorophenyl)-3-(4-(5-hydroxypyridin-2-yl)-1,4-diazepan-1-yl)pyrrolidin-2-one

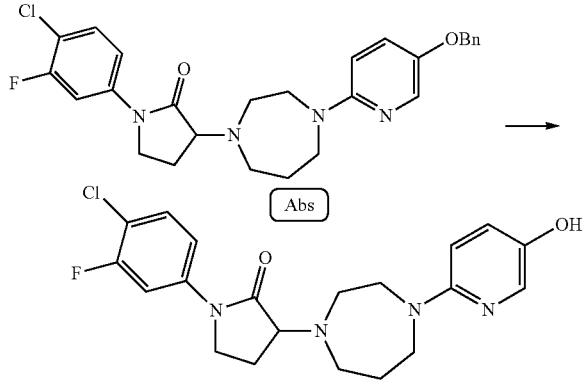

To a stirred solution of 3-(4-(5-(benzyloxy)pyridin-2-yl)-1,4-diazepan-1-yl)-1-(4-chloro-3-fluorophenyl)pyrrolidin-2-one (0.186 g, 0.376 mmol) in Methanol (10 mL) was added Pd/C (0.04 g, 0.376 mmol) at RT. The reaction mixture was connected to a hydrogen bladder through vacuum bend and was stirred at RT for 18 h. Major desired product mass, the reaction mass was filtered through celeite and the filtrate was concentrated to get the crude product 0.15 g. The crude compound was purified by SCP to get 1-(4-chloro-3-fluorophenyl)-3-(4-(5-hydroxypyridin-2-yl)-1,4-diazepan-1-yl)pyrrolidin-2-one (4 mg, 9.39 μmol, 2.497% yield) as pale yellow solid.

LCMS: Solvent A: 5% ACN, 95% Water, 10 mM NH4OAC, Solvent B: 95% ACN, 5% Water, 10 mM NH4OAC, Flow Rate: 4 ml/min, Temp: 50° C., Column: Ascentis Express C18 (50×4.6) mm, 2.7 μm, Time (min): 0-4, % B:0-100, RT−1.474 min, M(+1)−405.

Chiral screening: Injection Volume: 7, Co-Solvent: 0.3% DEA in Methanol, Column: Chiralcel OJ-H (4.6×250) mm, 5 u, Column Temperature: 26.6, Total Flow: 4, CO2 Flow Rate: 2.4, Co-Solvent Flow Rate: 1.6, Co-Solvent: 40, Back Pressure: 99, RT−2.78 min.

1H NMR: 400 MHz, DMSO-d6: δ 2.12-2.16 (m, 2H), 2.31-2.34 (m, 1H), 2.45-2.49 (m, 1H), 3.19-3.22 (m, 1H), 3.35-3.38 (m, 1H), 3.43-3.45 (m, 2H), 3.53-3.64 (m, 3H), 3.80-3.92 (m, 4H), 4.59 (t, J=19.60 Hz, 1H), 6.85 (d, J=9.20 Hz, 1H), 7.30-7.33 (m, 1H), 7.54-7.57 (m, 1H), 7.64-7.69 (m, 2H), 7.86 (dd, J=12.00, Hz, 1H).

Example 22 (P2) (Homochiral): 1-(4-chloro-3-fluorophenyl)-3-(4-(5-hydroxypyridin-2-yl)-1,4-diazepan-1-yl)pyrrolidin-2-one

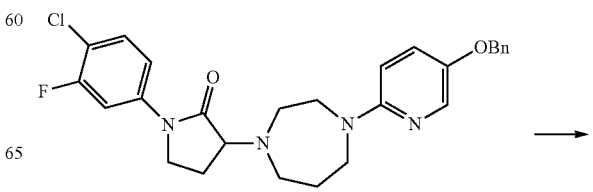

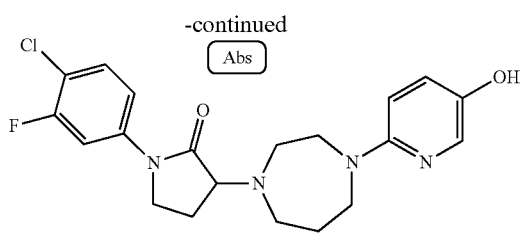

To a stirred solution of 3-(4-(5-(benzyloxy)pyridin-2-yl)-1,4-diazepan-1-yl)-1-(4-chloro-3-fluorophenyl)pyrrolidin-2-one (0.186 g, 0.376 mmol) in Methanol (10 mL) was added Pd/C (0.04 g, 0.376 mmol) at RT. The reaction mixture was connected to a hydrogen bladder through vacuum bend and was stirred at RT for 18 h. Major desired product mass, the reaction mass was filtered through celeite and the filtrate was concentrated to get the crude product. The crude compound was purified by SCP to obtain 1-(4-chloro-3-fluorophenyl)-3-(4-(5-hydroxypyridin-2-yl)-1,4-diazepan-1-yl)pyrrolidin-2-one (10 mg, 0.023 mmol, 6.18% yield) as pale yellow solid.

LCMS: Solvent A: 5% ACN, 95% Water, 10 mM NH4OAC, Solvent B: 95% ACN, 5% Water, 10 mM NH4OAC, Flow Rate: 4 ml/min, Temp: 50° C., Column: Ascentis Express C18 (50×4.6) mm, 2.7 μm, Time (min): 0-4, % B:0-100, RT–1.468 min, M(+)–405.

Chiral screening: Injection Volume: 4, Co-Solvent: 0.3% DEA in Methanol, Column: Chiralcel OJ-H (4.6×250) mm, 5 u, Column Temperature: 26.5, Total Flow: 3, CO2 Flow Rate: 1.95, Co-Solvent Flow Rate: 1.05, Co-Solvent: 35, Back Pressure: 99, RT–6.14 min.

1H NMR: 400 MHz, DMSO-d6: δ 2.12-2.16 (m, 2H), 2.31-2.34 (m, 1H), 2.45-2.49 (m, 1H), 3.19-3.22 (m, 1H), 3.35-3.38 (m, 1H), 3.43-3.45 (m, 2H), 3.53-3.64 (m, 3H), 3.80-3.92 (m, 4H), 4.59 (t, J=19.60 Hz, 1H), 6.85 (d, J=9.20 Hz, 1H), 7.30-7.33 (m, 1H), 7.54-7.57 (m, 1H), 7.64-7.69 (m, 2H), 7.86 (dd, J=12.00, Hz, 1H).

Example 23 (Homochiral)

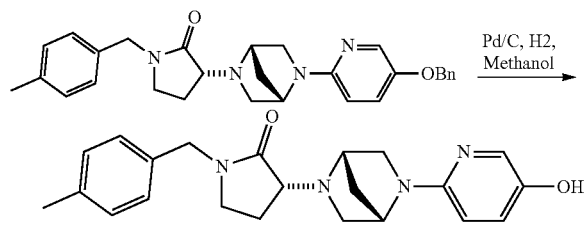

To a solution of (R)-3-((1S,4S)-5-(5-(benzyloxy)pyridin-2-yl)-2,5-diazabicyclo[2.2.1]heptan-2-yl)-1-(4-methylbenzyl)pyrrolidin-2-one (0.18 g, 0.142 mmol) in MeOH (5 mL) was added Pd/C (0.15 g, 0.141 mmol) and stirred at RT under hydrogen balloon pressure for overnight. The completion of the reaction was monitored by LCMS. Reaction mass was filtered through celite and concentrated under reduced pressure to got crude was dissolved in 2 mL of DMF and submitted to SCP. The crude material was purified via preparative LC/MS with the following conditions: Waters Xbridge C18, 19×150 mm, 5 μm; Guard Column: Waters XBridge C18, 19×10 mm, 5 μm; Mobile Phase A:5:95 Acetonitrile:water with 10 mM NH4OAc; Mobile Phase B: 95:5 Acetonitrile:water with 10 mM NH4OAc; Gradient: 10-45% B over 25 minutes, followed by a 10 minute hold at 45% B and 5 minute hold at 100% B; Flow:15 ml/min. Fractions containing the desired product were combined and dried using a Genevac centrifugal evaporator to get (R)-3-((1S,4S)-5-(5-hydroxypyridin-2-yl)-2,5-diazabicyclo[2.2.1]heptan-2-yl)-1-(4-methylbenzyl)pyrrolidin-2-one (4 mg, 9.83 μma 6.92% yield) as pale yellow solid.

LCMS: A: 95% Water: 5% Acetonitrile; 10 mM NH4OAC, B: 5% Water:95%, Acetonitrile; 10 mM NH4OAC, Flow: 1.1 ml/min, Temp:50° C., Column: Ascentis Express C18 (50×2.1) mm, 2.7 μm, Time (min): 0-3, % B: 0-100, RT–1.171 min, M(+1)–379.

H-NMR: 400 MHz, DMSO-d6: δ 1.71-1.81 (m, 3H), 2.07-2.11 (m, 1H), 2.27 (s, 3H), 2.73 (d, J=10.00 Hz, 1H), 3.00-3.17 (m, 4H), 3.22 (d, J=9.60 Hz, 1H), 3.35-3.37 (m, 1H), 3.88 (s, 1H), 4.24 (d, J=14.80 Hz, 1H), 4.30 (d, J=14.80 Hz, 1H), 4.40 (s, 1H), 6.39 (d, J=8.80 Hz, 1H), 7.02 (dd, J=12.00, Hz, 1H), 7.06 (d, J=7.60 Hz, 2H), 7.13 (d, J=8.00 Hz, 2H), 7.67 (d, J=2.80 Hz, 1H), 8.73 (s, 1H).

Chiral screening: Injection Volume: 5, Co-Solvent: 0.3% DEA in Methanol, Column: Whelk-01(R,R) (250×4.6) mm 5 u, Column Temperature: 26.7, Total Flow: 4, CO2 Flow Rate: 2.4, Co-Solvent Flow Rate: 1.6, Co-Solvent: 40, Back Pressure: 101. RT–5.7 min.

Example 24 (Homochiral)

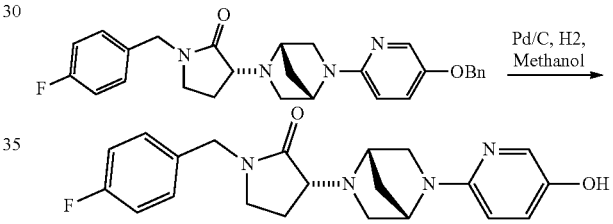

To a solution of (R)-3-((1S,4S)-5-(5-(benzyloxy)pyridin-2-yl)-2,5-diazabicyclo[2.2.1]heptan-2-yl)-1-(4-fluorobenzyl)pyrrolidin-2-one (0.18 g, 0.194 mmol) in MeOH (5 mL) was added Pd/C (0.15 g, 0.141 mmol) and stirred at RT under hydrogen bladder pressure for overnight. The completion of the reaction was monitored by LCMS. Reaction mass was filtered through celite and concentrated under reduced pressure to got crude was dissolved in 2 ml of DMF and submitted to SCP. The crude material was purified via preparative LC/MS with the following conditions: Waters Xbridge C18, 19×150 mm, 5 μm; Guard Column: Waters XBridge C18, 19×10 mm, 5 μm; Mobile Phase A:5:95 Acetonitrile:water with 10 mM NH4OAc; Mobile Phase B: 95:5 Acetonitrile:water with 10 mM NH4OAc; Gradient: 10-35% B over 25 minutes, followed by a 10 minute hold at 35% B and 5 minute hold at 100% B; Flow:15 ml/min. Fractions containing the desired product were combined and dried using a Genevac centrifugal evaporator (R)-1-(4-fluorobenzyl)-3-((1S,4S)-5-(5-hydroxypyridin-2-yl)-2,5-diazabicyclo[2.2.1]heptan-2-yl)pyrrolidin-2-one (11 mg, 0.028 mmol, 14.66% yield) as pale yellow solid.

LCMS: A: 95% Water: 5% Acetonitrile; 10 mM NH4OAC, B: 5% Water:95%, Acetonitrile; 10 mM NH4OAC, Flow: 1.1 ml/min, Temp:50° C., Column: Ascentis Express C18 (50×2.1) mm, 2.7 μm, Time (min): 0-3, % B: 0-100, RT–1.07 min, M(+1)–383.

1H-NMR: 400 MHz, MeOD: δ 1.91-1.98 (m, 3H), 2.27-2.31 (m, 1H), 2.99 (d, J=11.60 Hz, 1H), 3.20-3.30 (m, 3H), 3.34-3.43 (m, 2H), 3.50 (d, J=10.00 Hz, 1H), 4.09 (s, 1H), 4.35 (d, J=14.80 Hz, 1H), 4.45 (d, J=15.20 Hz, 1H), 4.50 (s, 1H), 6.51 (d, J=9.60 Hz, 1H), 7.05-7.09 (m, 2H), 7.15 (dd, J=12.00, Hz, 1H), 7.27-7.30 (m, 2H), 7.68 (d, J=2.80 Hz, 1H).

Chiral screening: Injection Volume: 5, Co-Solvent: 0.3% DEA in Methanol, Column: Lux cellulose-2(4.6×250) mm, 5 u, Column Temperature: 26.8, Total Flow: 4, CO2 Flow Rate: 2.4, Co-Solvent Flow Rate: 1.6, Co-Solvent: 40, Back Pressure: 101, RT–3.75 min.

Example 25 (P1 & P2)

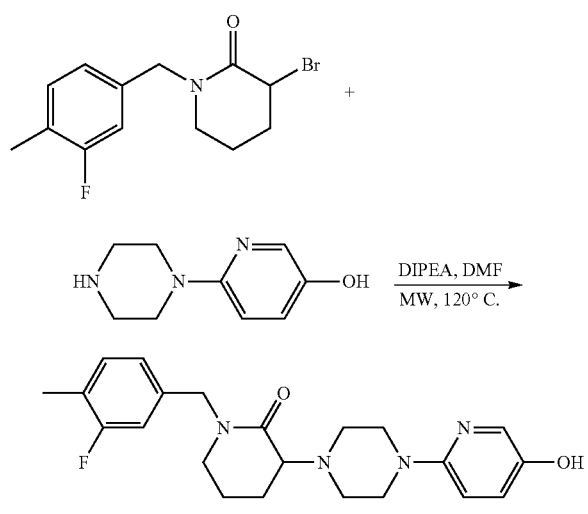

To a stirred solution of 6-(piperazin-1-yl)pyridin-3-ol hydrochloride (70 mg, 0.325 mmol) in dry DMF (1.5 mL) was added DIPEA (0.170 mL, 0.974 mmol) and 3-bromo-1-(3-fluoro-4-methylbenzyl)piperidin-2-one (97 mg, 0.325 mmol) mixture was heated under MW at 120° C. for 90 min. The completion of the reaction was monitored by LCMS. The reaction mixture was concentrated to remove DMF. The crude as such was purified by ISCO. The crude compound was purified by ISCO (40 g silica gel column, eluted with 50% ethyl acetate/Pet ether) to get 25 (a racemic mixture); 1-(3-fluoro-4-methylbenzyl)-3-(4-(5-hydroxypyridin-2-yl)piperazin-1-yl)piperidin-2-one (60 mg, 0.151 mmol, 46.4% yield) as brown gum. The racemic mixture was submitted to Chiral SFC to get P1; 1-(3-fluoro-4-methylbenzyl)-3-(4-(5-hydroxypyridin-2-yl)piperazin-1-yl)piperidin-2-one (11.1 mg, 0.026 mmol, 8.07% yield) and P2; 1-(3-fluoro-4-methylbenzyl)-3-(4-(5-hydroxypyridin-2-yl)piperazin-1-yl)piperidin-2-one (9.6 mg, 0.023 mmol, 7.13% yield).

SFC Purification Method:

Analytical SFC Conditions: Column/dimensions: Luxcellulose-2(250×4.6) mm, 5 u, % CO2: 60%, % Co solvent: 40% (0.25% DEA in Methanol), Total Flow: 4.0 g/min, Back Pressure: 100 bar, Temperature: 25° C., UV: 244.

Preparative SFC Conditions: Column/dimensions: Lux-cellulose-2(250×21.5) mm, 5 u, % CO2: 60%, % Co solvent: 45% (0.25% DEA in Methanol), Total Flow: 75.0 g/min, Back Pressure: 100 bar, Temperature: 25° C., UV: 244, Peak number: Retention Time::Peak 1: 4.20::Peak 2: 6.00, Solubility: 10 ml in Methanol, Loadability/Inj: 6 mg/mL, Total No of injections:6, Total Time for purification 0.50 hrs, Instrument details: Make/Model: Thar SFC-80.

For P1 (Homochiral):

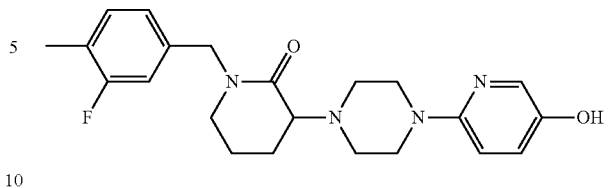

$^1$H NMR: (400 MHz, DMSO-d$_6$) d=8.98-8.92 (m, 1H), 7.75-7.71 (m, 1H), 7.28-7.21 (m, 1H), 7.08-7.04 (m, 1H), 7.01-6.95 (m, 2H), 6.73-6.67 (m, 1H), 4.52-4.40 (m, 3H), 3.29-3.17 (m, 6H), 3.16-3.08 (m, 1H), 2.98-2.90 (m, 2H), 2.70-2.62 (m, 2H), 2.23-2.19 (m, 3H), 1.91-1.75 (m, 4H).

LCMS: Column-Ascentis Express C18 (50×2.1 mm-2.7 μm), Mphase A: 10 mM NH4C00H IN WATER:ACN(98:02), Mphase B: 10 mM NH4C00H IN WATER:ACN(02:98), Flow=1 ML/MIN, Time: % B::0.0:0.0::1.7:100.0::3.0:100.0::3.2:0.0, RT–1.99 min, M(+1)–399.

Chiral purity: Injection Volume: 7, Co-Solvent: 0.3% DEA in Methanol, Column: Lux cellulose-2(4.6×250) mm, 5 u, Column Temperature: 26.4, Total Flow: 4, CO2 Flow Rate: 2.4, Co-Solvent Flow Rate: 1.6, Co-Solvent %: 40, Back Pressure: 100, RT–4.12 min.

For P2 (Homochiral):

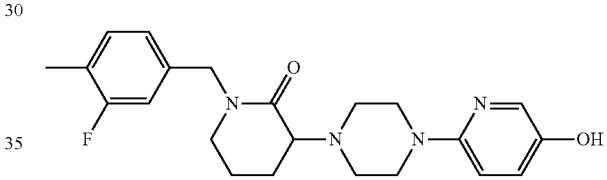

$^1$H NMR: (400 MHz, DMSO-d$_6$) d=9.05-8.90 (m, 1H), 7.73 (d, J=2.5 Hz, 1H), 7.25 (s, 1H), 7.05 (dd, J=9.0, 3.0 Hz, 1H), 7.00-6.95 (m, 2H), 6.70 (d, J=9.0 Hz, 1H), 4.46 (d, J=13.1 Hz, 2H), 3.28-3.08 (m, 7H), 2.94 (d, J=5.0 Hz, 2H), 2.66 (d, J=6.0 Hz, 2H), 2.21 (d, J=1.5 Hz, 3H), 1.86 (br. s., 3H), 1.75-1.65 (m, 1H).

LCMS: Column-Ascentis Express C18 (50×2.1 mm-2.7 μm), Mphase A: 10 mM NH4C00H IN WATER:ACN(98:02), Mphase B: 10 mM NH4C00H IN WATER:ACN(02:98), Flow=1 ML/MIN, Time: % B::0.0:0.0::1.7:100.0::3.0:100.0::3.2:0.0, RT–1.99 min, M(+1)–399.

Chiral purity: Injection Volume: 7, Co-Solvent: 0.3% DEA in Methanol, Column: Lux cellulose-2(4.6×250) mm, 5 u, Column Temperature: 26.3, Total Flow: 4, CO2 Flow Rate: 2.4, Co-Solvent Flow Rate: 1.6, Co-Solvent %: 40, Back Pressure: 94, RT–4.67 min.

Example 26 (Homochiral)

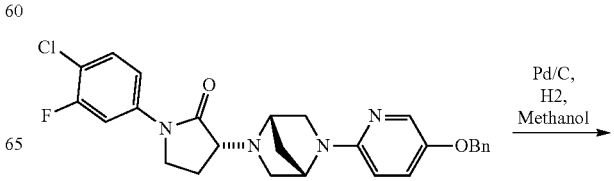

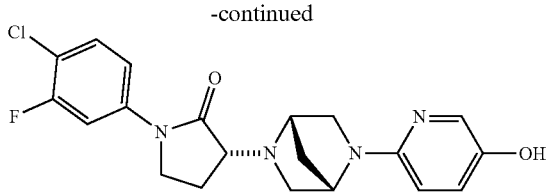

To a solution of 3-((1S,4S)-5-(5-(benzyloxy)pyridin-2-yl)-2,5-diazabicyclo[2.2.1]heptan-2-yl)-1-(4-chloro-3-fluorophenyl)pyrrolidin-2-one (0.18 g, 0.215 mmol) in MeOH (5 mL) was added Pd/C (0.11 g, 0.103 mmol) and stirred at RT under hydrogen bladder pressure for overnight. The completion of the reaction was monitored by LCMS. Reaction mass was filtered through celite and concentrated under reduced pressure to got crude was dissolved in 2 mL of DMF and submitted to SCP. The crude material was purified via preparative LC/MS with the following conditions: Waters Xbridge C18, 19×150 mm, 5 μm; Guard Column:Waters XBridge C18, 19×10 mm, 5 μm; Mobile Phase A:5:95 Acetonitrile:water with 0.1% TFA; Mobile Phase B: 95:5 Acetonitrile:water with 0.1% TFA; Gradient:0-20% B over 25 minutes, followed by a 10 minute hold at 20% B and 5 minute hold at 100% B; Flow:15 ml/min. Fractions containing the desired product were combined and dried using a Genevac centrifugal evaporator to get 1-(4-chloro-3-fluorophenyl)-3-((1S,4S)-5-(5-hydroxypyridin-2-yl)-2,5-diazabicyclo[2.2.1]heptan-2-yl)pyrrolidin-2-one (2 mg, 4.96 μmol, 2.305% yield) as pale yellow solid.

LCMS: A: 95% Water: 5% Acetonitrile; 10 mM NH4OAC, B: 5% Water:95%, Acetonitrile; 10 mM NH4OAC, Flow: 1.1 ml/min, Temp: 50° C., Column: Ascentis Express C18 (50×2.1) mm, 2.7 μm, Time (min): 0-3, % B: 0-100, RT-1.302 min, M (+1)-403.

1H NMR: 400 MHz, MeOD: δ 2.12-2.26 (m, 4H), 2.61 (t, J=12.00 Hz, 1H), 3.51-3.54 (m, 1H), 3.72 (bs, 3H), 3.80-3.93 (m, 3H), 4.17 (bs, 1H), 6.86 (d, J=9.20 Hz, 1H), 7.38-7.51 (m, 3H), 7.55 (s, 1H), 7.78-7.81 (m, 1H).

Chiral screening: Injection Volume: 7, Co-Solvent: 0.3% DEA in Methanol, Column: Lux cellulose-4 (250×4.6) mm, 5 u, Column Temperature: 26, Total Flow: 4, CO2 Flow Rate: 2.4, Co-Solvent Flow Rate: 1.6, Co-Solvent: 40, Back Pressure: 98, RT-4.43 min.

Example 27 (Homochiral)

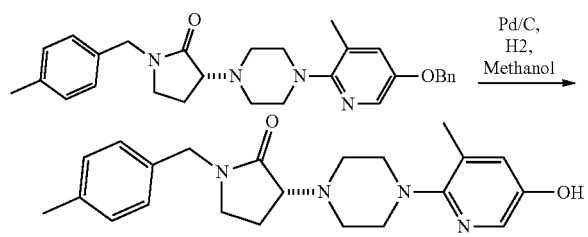

To a solution of (R)-3-(4-(5-(benzyloxy)-3-methylpyridin-2-yl)piperazin-1-yl)-1-(4-methylbenzyl)pyrrolidin-2-one (0.15 g, 0.169 mmol) in MeOH (5 mL) was added Pd/C (0.1 g, 0.094 mmol) and stirred at RT under hydrogen bladder pressure for overnight. The completion of the reaction was monitored by LCMS. Reaction mass was filtered through celite and concentrated under reduced pressure to get crude was dissolved in 2 mL of DMF and submitted to SCP. The crude material was purified via preparative LC/MS with the following conditions: Waters Xbridge C18, 19×150 mm, 5 μm; Guard Column: Waters XBridge C18, 19×10 mm, 5 μm; Mobile Phase A:5:95 Acetonitrile:water with 10 mM NH4OAc; Mobile Phase B: 95:5 Acetonitrile:water with 10 mM NH4OAc; Gradient:10-45% B over 25 minutes, followed by a 10 minute hold at 45% B and 5 minute hold at 100% B; Flow:15 ml/min. Fractions containing the desired product were combined and dried using a Genevac centrifugal evaporator to get (R)-3-(4-(5-hydroxy-3-methyl-pyridin-2-yl)piperazin-1-yl)-1-(4-methylbenzyl)pyrrolidin-2-one (6 mg, 0.015 mmol, 9.15% yield) as pale yellow solid.

LCMS: Solvent A: 5 ACN, 95% Water, 10 mM NH4OAC, Solvent B: 95% ACN, 5% Water, 10 mM NH4OAC, Flow Rate: 4 ml/min, Temp: 50° C., Column:Ascentis Express C18 (50×4.6) mm, 2.7 μm, Time (min): 0-4, % B:0-100, RT-2.112 min, M(+1)-381.

1H NMR: 400 MHz, DMSO-d6: δ 2.08 (s, 3H), 2.21 (s, 1H), 2.31 (s, 3H), 2.35-2.41 (m, 2H), 3.26-3.32 (m, 8H), 4.36-4.49 (m, 4H), 6.98-7.11 (m, 1H), 7.16-7.23 (m, 4H), 7.72 (d, J=2.80 Hz, 1H).

Chiral screening: Injection Volume: 5, Co-Solvent: 0.3% DEA in Methanol, Column: Lux cellulose-4 (250×4.6) mm, 5 u, Column Temperature: 26.9, Total Flow: 4, CO2 Flow Rate: 2.4, Co-Solvent Flow Rate: 1.6, Co-Solvent: 40, Back Pressure: 100, RT-4.58 min.

Example 28 2: 6-(4-(1-(3-fluoro-4-methylphenyl)-2-oxopyrrolidin-3-yl)piperazin-1-yl)pyridin-3-yl dihydrogen phosphate

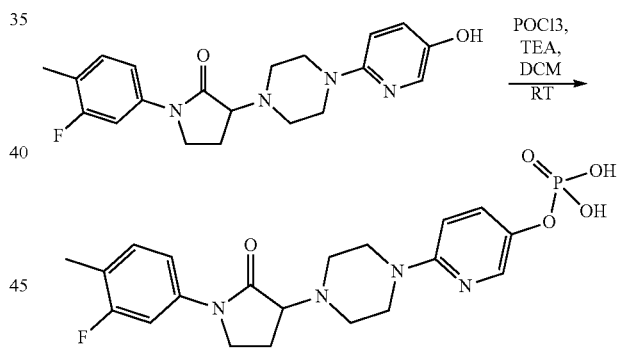

To a solution of 1-(3-fluoro-4-methylphenyl)-3-(4-(5-hydroxypyridin-2-yl)piperazin-1-yl)pyrrolidin-2-one (55 mg, 0.148 mmol) in 1.0 mL of dry DCM and TRIETHYLAMINE (0.145 mL, 1.039 mmol) at −20° C. was added POCl3 (0.069 mL, 0.742 mmol). The reaction mixture was stirred at RT for 3 h. The reaction mixture was added water 2 mL. The reaction mixture was stirred at RT for 18 h. The completion of the reaction was monitored by LCMS. The reaction mixture was concentrated to get crude residue 0.1 g. The crude was purified by reverse phase Prep-HPLC. After completion of purification the fractions were lyophilized to get 6-(4-(1-(3-fluoro-4-methylphenyl)-2-oxopyrrolidin-3-yl)piperazin-1-yl)pyridin-3-yl dihydrogen phosphate (23.56 mg, 0.051 mmol, 34.5% yield) as off white solid.

HPLC: COLUMN:CHIRAL PAK ADH (250×4.6 mm), 5 micron, MOBILE PHASE: 0.2% DEA n-HEXANE:ETHANOL:80:20, RT-26.88 min.

LCMS: Column-Ascentis Express C8 (50×2.1 mm-2.7 μm), Mphase A: 10 mM NH4COOH IN WATER:ACN(98:02), Mphase B: 10 mM NH4COOH IN WATER:ACN(02:98), RT–0.8 min, M(+1)–451.

$^1$H NMR: (400 MHz, DMSO-$d_6$) d ppm 1.99-2.13 (m, 4H) 2.21 (d, J=1.51 Hz, 2H) 2.31-2.37 (m, 4H) 2.57-2.71 (m, 2H) 2.88-3.01 (m, 2H) 3.61-3.81 (m, 3H) 6.74 (d, J=8.53 Hz, 1H) 7.04-7.20 (m, 1H) 7.25-7.44 (m, 3H) 7.63 (dd, J=12.80, 2.26 Hz, 1H) 7.91 (br. s., 1H).

Biological Methods

Radioligand Binding Assay.

Binding experiments to determine binding to NR2B-subtype NMDA receptors were performed on forebrains of 8-10 weeks old male Sprague Dawley rats (Harlan, Netherlands) using $^3$H Ro 25-6981 (Mutel V; Buchy D; Klingelschmidt A; Messer J; Bleuel Z; Kemp J A; Richards J G. *Journal of Neurochemistry*, 1998, 70(5):2147-2155. Rats were decapitated without anesthesia using a Guillotine (approved by animal ethics committee) and the harvested brains were snap-frozen and stored at −80° C. for 3-6 months for membrane preparation.

For membrane preparation, rat forebrains were thawed on ice for 20 minutes in homogenization buffer composed of 50 mM $KH_2PO_4$ (pH adjusted to 7.4 with KOH), 1 mM EDTA, 0.005% Triton X 100 and protease inhibitor cocktail (Sigma Aldrich). Thawed brains were homogenized using a Dounce homogenizer and centrifuged at 48000×g for 20 min. The pellet was resuspended in cold buffer and homogenized again using a Dounce homogenizer. Subsequently, the homogenate was aliquoted, snap-frozen and stored at −80° C. for not more than 3-4 months.

To perform the competition binding assay, thawed membrane homogenate was added to each well of a 96-well plate (20 μg/well). The experimental compounds were serially diluted in 100% DMSO and added to each row of the assay plate to achieve desired compound concentrations, keeping the DMSO concentration in the assay plate at 1.33% of the final reaction volume. Next, $^3$H Ro 25-6981 (4 nM) was added to the assay plate. After incubation for 1 hr at room temperature, the membrane bound radioligand was harvested on to GF/B filter plates (treated with 0.5% PEI for 1 hr at room temperature). The filter plates were dried at 50° C. for 20 mins, incubated with microscint 20 for 10 minutes and finally, the counts were read on TopCount (Perkin Elmer). Non-specific binding was determined using MK-0657 (the preparation of this compound is described as example 1 in WO 2004 108705 (40 μM). CPM values were converted to % inhibition and the concentration response curves were plotted using custom made software. Each experiment was repeated at least twice to obtain the final binding $K_i$ values for experimental compounds. Using this assay, the compound of example 14, P-1 shows a binding Ki of 4 nM.

Ex Vivo Occupancy Assay.

This assay demonstrates that the compound of example 1 occupies brain-resident NR2B-subtype receptors in animals after dosing. 7-9 weeks old male CD-1 mice were dosed intravenously in a vehicle consisting of 10% dimethylacetamide, 40% PEG-400, 30% hydroxypropyl betacyclodextrin, and 30% water with experimental compounds and the forebrains were harvested 15 minutes post-dosing by decapitation. The brain samples were immediately snap-frozen and stored at −80° C. On the following day, the dosed brain samples were thawed on ice for 15-20 minutes followed by homogenization using Polytron for 10 seconds in cold homogenization buffer composed of 50 mM $KH_2PO_4$ (pH adjusted to 7.4 with KOH), 1 mM EDTA, 0.005% Triton X 100 and protease inhibitor cocktail (Sigma Aldrich). The crude homogenates were further homogenized using a Dounce homogenizer and the homogenized membrane aliquots from all animals were flash-frozen and stored at −80° C. until further use. The whole homogenization process was performed on ice.

For determining occupancy, the membrane homogenates were first thawed on ice and then needle-homogenized using a 25 gauge needle. The homogenized membrane (6.4 mg/ml) was added to a 96-well plate followed by addition of $^3$H Ro 25-6981 (6 nM). The reaction mixture was incubated for 5 minutes on a shaker at 4° C. and then harvested onto GF/B filter plates (treated with 0.5% PEI for 1 hr at room temperature). The filter plates were dried at 50° C. for 20 mins, incubated with microscint 20 for 10 minutes and read on TopCount (Perkin Elmer). Each dose or compound group consisted of 4-5 animals. The control group of animals was dosed with vehicle alone. Membrane from each animal was added in triplicates to the assay plate. Non-specific binding was determined using 10 μM Ro 25-6981 added to the wells containing membrane homogenates from vehicle-dosed animals. Specific counts/minute was converted to % occupancy at each dose of a compound for each animal using the following equation:

$$\% \text{ Occupancy (animal } A) = 100 - \left( \frac{\text{specific } CPM \text{ of animal A}}{\text{Average } CPM \text{ from control group}} \times 100 \right)$$

Using this procedure, the compound of example 14, P1 shows 86% NR2B receptor occupancy after a 3 mg/Kg i.v. dose. Drug levels were determined by mass spectroscopy in the usual manner. Drug levels in the blood plasma were 1018 nM in at this dose, and drug levels in the homogenized brain tissue were 1342 nM.

hERG Electrophysiology Assay.

The experimental compounds were assessed for hERG activity on HEK 293 cells stably expressing hERG channels using patch clamp technique. Coverslips plated with hERG expressing cells were placed in the experimental chamber and were perfused with a solution composed of (in mM): 140 NaCl, 4 KCl, 1.8 $CaCl_2$, 1 $MgCl_2$, 10 Glucose, 10 HEPES (pH 7.4, NaOH) at room temperature. Borosilicate patch pipettes had tip resistances of 2-4 Mohms when filled with an internal solution containing: 130 KCl, 1 $MgCl_2$, 1 $CaCl_2$, 10 EGTA, 10 HEPES, 5 ATP-$K_2$ (pH 7.2, KOH). The cells were clamped at −80 mV in whole cell configuration using an Axopatch 200B (Axon instruments, Union City, Calif.) patch clamp amplifier controlled by pClamp (Axon instruments) software. Upon formation of a gigaseal, the following voltage protocol was repeatedly (0.05 Hz) applied to record tail currents: depolarization step from −80 mV to +20 mV for 2 seconds followed by a hyperpolarization step to −65 mV (3 seconds) to elicit tail currents and then, back to the holding potential. Compounds were applied after stabilization of tail current. First, tail currents were recorded in presence of extracellular solution alone (control) and subsequently, in extracellular solution containing increasing compound concentrations. Each compound concentration was applied for 2-5 minutes. The percentage inhibition at each concentration was calculated as reduction in peak tail current with respect to the peak tail current recorded in the presence of control solution. Data analysis was performed in custom made software. The percent inhibitions at different concentrations were plotted to obtain a concentration response curve, which was subsequently fitted with a four parameter equation to calculate the hERG $IC_{50}$ value. Using this procedure, the compound of example 14, P-1 is a poor inhibitor of the hERG channel, with an $IC_{50}=8.9$ µM.

Mouse Forced Swim Test (mFST).

Forced Swim Test (FST) is an animal model used to assess antidepressant compounds in preclinical studies. The FST was performed similar to the method of Porsolt et al. with modifications (Porsolt R D, Bertin A, Jalfre M. Behavioral despair in mice: a primary screening test for antidepressants. Arch Int Pharmacodyn Ther 1977; 229:327-36). In this paradigm, mice are forced to swim in an inescapable cylinder filled with water. Under these conditions, mice will initially try to escape and eventually develop immobility behavior; this behavior is interpreted as a passive stress-coping strategy or depression-like behavior. Swim tanks were positioned inside a box made of plastic. Each tank was separated from each other by opaque plastic sheets to the height of cylinders. Three mice were subjected to test at a time. Swim sessions were conducted for 6 min by placing mice in individual glass cylinders (46 cm height×20 cm diameter) containing water (20-cm deep, maintained at 24-25° C.). At this water level, the mouse tail does not touch the bottom of the container. The mouse was judged to be immobile whenever it remained floating passively without struggling in the water and only making those movements necessary to keep its nose/head above the water and to keep it afloat. The duration of immobility was evaluated during the total 6 min of the test and expressed as duration (sec) of immobility. Each mouse was tested only once. At the end of each session, mice were dried with a dry cloth and returned to their home cage placed on a thermal blanket to prevent hypothermia. Water was replaced after each trial. All testing sessions were recorded with a video camera (Sony Handicam, Model: DCR-HC38E; PAL) and scoring was done using the Forced Swim Scan, Version 2.0 software (Clever Systems Inc., Reston, Va., USA; see Hayashi E, Shimamura M, Kuratani K, Kinoshita M, Hara H. Automated experimental system capturing three behavioral components during murine forced swim test. Life Sci. 2011 Feb. 28; 88(9-10):411-7 and Yuan P, Tragon T, Xia M, Leclair C A, Skoumbourdis A P, Zheng W, Thomas C J, Huang R, Austin C P, Chen G, Guitart X. Phosphodiesterase 4 inhibitors enhance sexual pleasure-seeking activity in rodents. Pharmacol Biochem Behav. 2011; 98(3):349-55). For NCE testing: Test compound was administered in mice 15 min before swim session by i.v. route and immobility time was recorded for next 6 min. At the end of FST, the mouse were euthanized by rapid decapitation method and plasma and brain samples were collected and stored under −80° C. till further analysis. In the mouse forced swim assay, the compound of example 1 was dosed intravenously in a vehicle of 30% hydroxypropyl betacyclodextrin/70% citrate buffer pH 4 at a 5 mL/Kg dosing volume. The compound of example 14, P-1 demonstrated a statistically significant decrease in immobility time at 3 mg/Kg under these conditions. Drug levels were 314 nM in the plasma and 410 nM in the brain at this dose. The NR2B receptor occupancy was determined as reported above and was determined to be 67%.

It will be evident to one skilled in the art that the present disclosure is not limited to the foregoing disclosure and that it can be embodied in other specific forms without departing from the essential attributes thereof. It is therefore desired that the instant disclosure be considered in all respects as illustrative and not restrictive, reference being made to the appended claims, rather than to the foregoing disclosure, and all changes which come within the meaning and range of equivalency of the claims are therefore intended to be embraced therein.

We claim:
1. A compound of the formula I

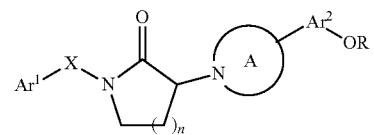

where:
Ar$^1$ is phenyl and is substituted with 0-3 substituents selected from cyano, halo, alkyl, haloalkyl, and haloalkoxy;
Ar$^2$ is pyridinyl or pyrimdinyl, and is substituted with 1 OR substituent and with 0-2 halo or alkyl substituents;
R is hydrogen or a prodrug moiety selected from the group consisting of alkyl esters, amino acid esters, alkoxy esters, phosphonic acids, phosphonic alkyl esters, alkoxyphosphononate acid, alkoxyphosphonate alkyl esters, alkyl carabamates, amino acid carbamates, alkyl phosporamidates, aryl phosphoramidates, and sulfamates;
X is a bond or $C_1$-$C_3$ alkylene;
n is 1 or 2;
ring A is piperazinyl, homopiperazinyl, or 2,5-diazabicyclo[2.2.1]heptanes, piperazin-2-one and is substituted with 0-4 substituents selected from halo, alkyl, hydroxy, or alkoxy;
or a pharmaceutically acceptable salt thereof.

2. A compound of claim 1 where n is 1 and ring A is piperazinyl substituted with 0-2 alkyl substituents.

3. A compound of claim 1 where Ar$^1$ is phenyl substituted with 0-3 substituents selected from cyano, halo, alkyl, haloalkyl, and haloalkoxy.

4. A compound of claim 1 where Ar$^2$ is selected from

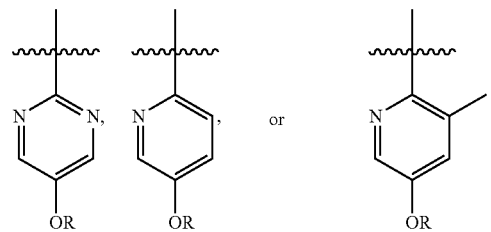

and R is selected from hydrogen, amino acid esters, phosphonic acids, alkoxyphosphononate acid, alkyl carabamates, amino acid carbamates, alkyl phosporamidates, aryl phosphoramidates, and sulfamates.

5. A compound of claim 1 where X is methylene.
6. A compound of claim 1 where R is hydrogen.
7. A compound of claim 1 where R is P(=O)(OH)$_2$.
8. A compound of claim 1 selected from the group consisting of
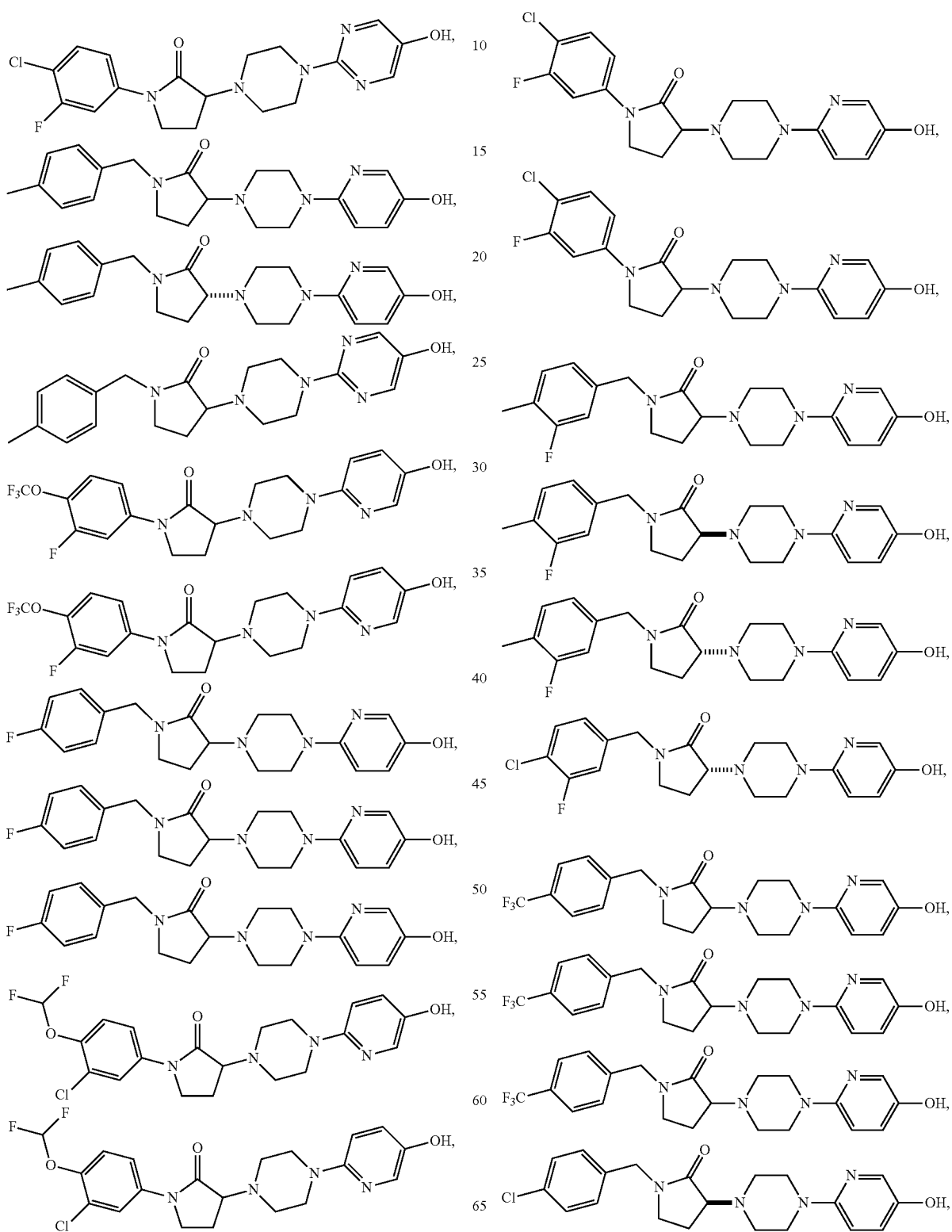

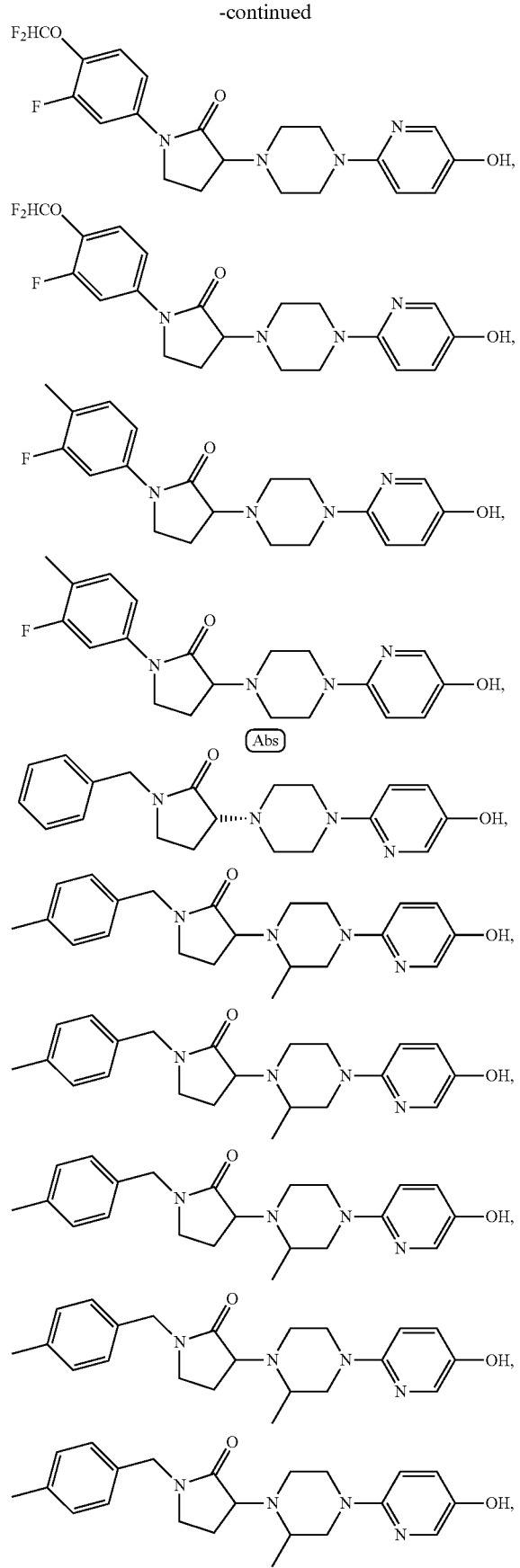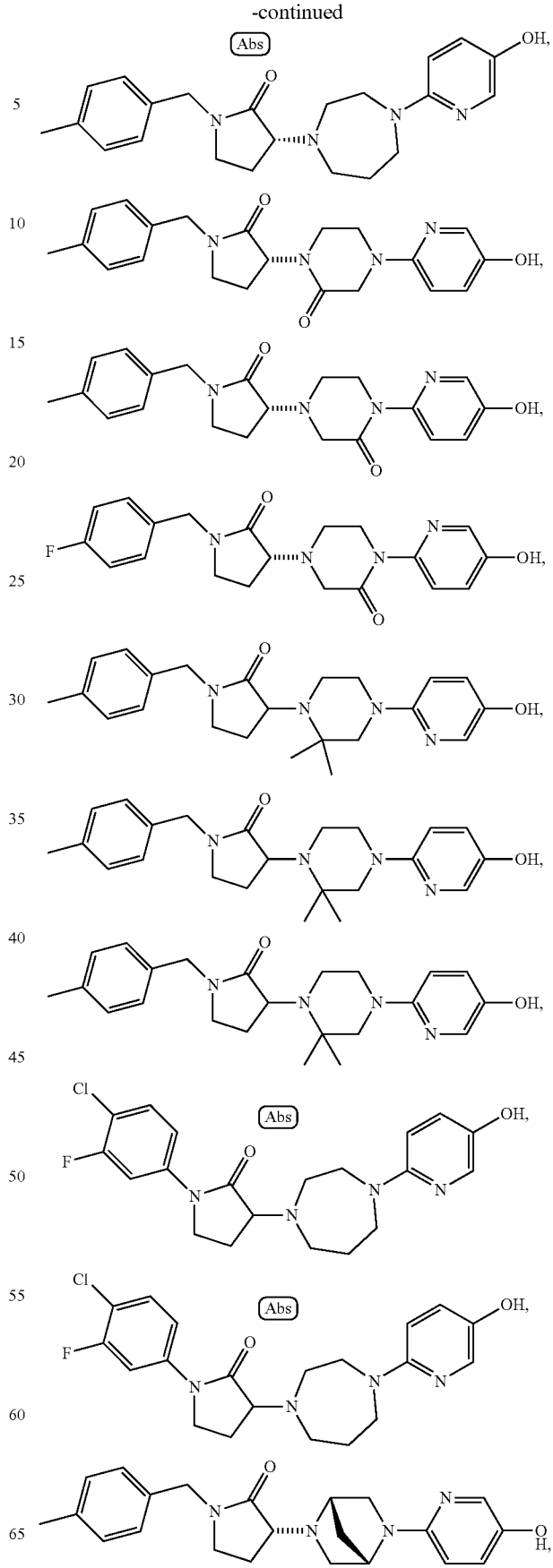

-continued

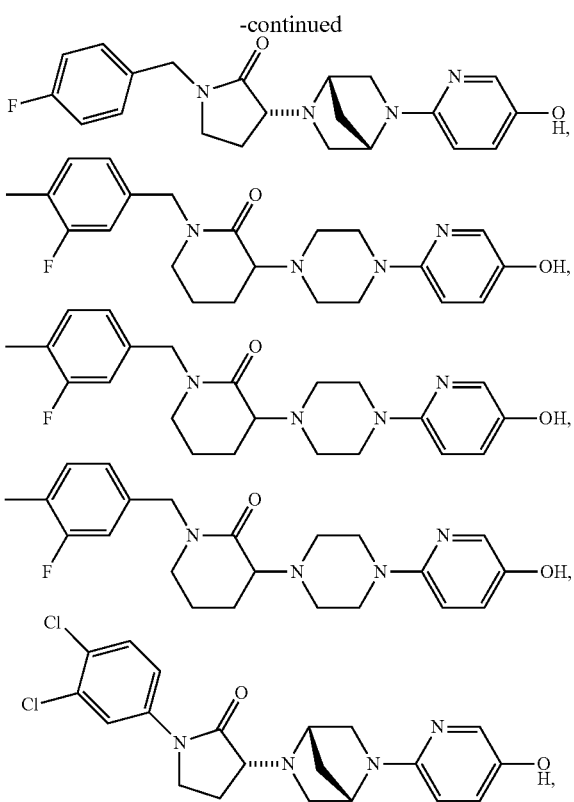

or a pharmaceutically acceptable salt thereof.

9. A pharmaceutical composition comprising a compound of claim 1 or a pharmaceutically acceptable salt thereof and a pharmaceutically acceptable carrier.

10. A method for the treatment of depression, Alzheimer's disease, neuropathic pain, or Parkinson's disease, which comprises administering to a patient a therapeutically affective amount of a compound of claim 1.

11. The method of claim 10 directed to the treatment of depression.

12. The method of claim 10 directed to the treatment of Alzheimer's disease.

13. The method of claim 10 directed to the treatment of neuropathic pain.

* * * * *

UNITED STATES PATENT AND TRADEMARK OFFICE
CERTIFICATE OF CORRECTION

PATENT NO. : 10,344,020 B2
APPLICATION NO. : 15/767386
DATED : July 9, 2019
INVENTOR(S) : Islam et al.

It is certified that error appears in the above-identified patent and that said Letters Patent is hereby corrected as shown below:

In the Claims

In Claim 1, Column 64, Line 30, delete "pyrimdinyl," and insert -- pyrimidinyl, --, therefor.

In Claim 1, Column 64, Line 35, delete "alkoxyphosphononate" and insert -- alkoxyphosphonate --, therefor.

In Claim 1, Column 64, Line 36, delete "carabamates," and insert -- carbamates, --, therefor.

In Claim 1, Column 64, Line 37, delete "phosporamidates," and insert -- phosphoramidates, --, therefor.

In Claim 4, Column 64, Line 65, delete "alkoxyphosphononate" and insert -- alkoxyphosphonate --, therefor.

In Claim 4, Column 64, Line 65, delete "carabamates," and insert -- carbamates, --, therefor.

In Claim 4, Column 64, Line 66, delete "phosporamidates," and insert -- phosphoramidates, --, therefor.

In Claim 8, Column 69, Line 24-30 (Approx.), delete "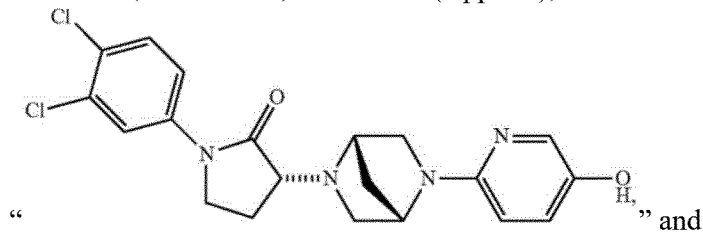" and

Signed and Sealed this
Fifteenth Day of March, 2022

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,344,020 B2 insert -- 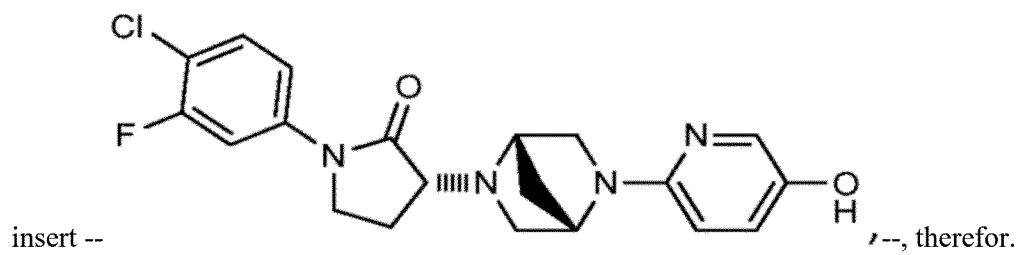 --, therefor.